(12) United States Patent
Tao et al.

(10) Patent No.: US 8,765,426 B2
(45) Date of Patent: Jul. 1, 2014

(54) PANTOTHENIC ACID BIOSYNTHESIS IN ZYMOMONAS

(75) Inventors: Luan Tao, Wallingford, PA (US); Jean-Francois Tomb, Wilmington, DE (US); Paul V. Viitanen, West Chester, PA (US)

(73) Assignee: E I du Pont de Nemours and Company, Wilmington, DE (US)

( * ) Notice: Subject to any disclaimer, the term of this patent is extended or adjusted under 35 U.S.C. 154(b) by 130 days.

(21) Appl. No.: 13/433,343

(22) Filed: Mar. 29, 2012

(65) Prior Publication Data

US 2013/0078694 A1 Mar. 28, 2013

Related U.S. Application Data

(60) Provisional application No. 61/472,664, filed on Apr. 7, 2011.

(51) Int. Cl.
| | |
|---|---|
| *C12P 1/00* | (2006.01) |
| *C12P 13/02* | (2006.01) |
| *C12P 17/04* | (2006.01) |
| *C12P 13/06* | (2006.01) |
| *C12N 15/52* | (2006.01) |
| *C12N 9/90* | (2006.01) |

(52) U.S. Cl.
USPC ........ 435/161; 435/476; 435/252.3; 536/23.2

(58) Field of Classification Search
None
See application file for complete search history.

(56) References Cited

U.S. PATENT DOCUMENTS

| | | | |
|---|---|---|---|
| 5,514,583 A | 5/1996 | Picataggio et al. | |
| 5,712,133 A | 1/1998 | Picataggio et al. | |
| 6,171,845 B1 | 1/2001 | Elischweski et al. | |
| 7,223,575 B2 | 5/2007 | Zhang et al. | |
| 7,629,156 B2 | 12/2009 | Viitanen et al. | |
| 7,741,084 B2 | 6/2010 | Viitanen et al. | |
| 7,741,119 B2 | 6/2010 | Viitanen et al. | |
| 7,897,396 B2 | 3/2011 | Caimi et al. | |
| 7,932,063 B2 | 4/2011 | Dunson et al. | |
| 7,998,722 B2 | 8/2011 | Viitanen et al. | |
| 2005/0089973 A1 | 4/2005 | Yocum et al. | |
| 2005/0221466 A1 | 10/2005 | Liao et al. | |
| 2009/0031453 A1 | 1/2009 | Jessen et al. | |

FOREIGN PATENT DOCUMENTS

| | | |
|---|---|---|
| WO | W09528476 A1 | 10/1995 |
| WO | W003006664 A2 | 1/2003 |
| WO | W02010075241 A1 | 7/2010 |

OTHER PUBLICATIONS

Feldmann et al, Pentose Metabolism in Zymomonas Mobilis Wild-Type and Recombinant Strains (1992) Appl Microbiol Biotechnol 38: 354-361.
Kanehisa et al, KEGG: Kyoto Encyclopedia of Genes and Genomes (2000) Nucleic Acids Research vol. 28 No. 1, 27-30.
Kanehisa et al, (2002) Nucleic Acids Res 30, 42-46.
Kanehisa et al, (2006) Nucleic Acids Res 34, D354-357.
Nipkow et al (1984) Appl Microbiol Biotechnol 19, 237-240.
Ramjee et al (1997) Biochem J 323, 661-669.
Seo et al (2005) Nat Biotechnol 23, 63-68 Seo_etal_2005_Nat_Biotechnol.pdf.
Zhang et al (1995) Science 267, 240-243.

*Primary Examiner* — Kagnew H Gebreyesus

(57) ABSTRACT

*Zymomonas* is unable to synthesize pantothenic acid and requires this essential vitamin in growth medium. *Zymomonas* strains transformed with an operon for expression of 2-dehydropantoate reductase and aspartate 1-decarboxylase were able to grow in medium lacking pantothenic acid. These strains may be used for ethanol production without pantothenic acid supplementation in seed culture and fermentation media.

17 Claims, 10 Drawing Sheets

---------xxxxxxxxKxHxxxxxxxxxxYxG-Sxxxxxxxxxx
xxxxxxxVxxxxxxxxGxRxxTYxxxx----xxxxxxxxxxGxxxxxxxxxxxxxxxxxxxxxxxxx
xxxxxxxxxxxxxxxxx--------xxxxxxxxxx---------xx
xxxx------------

B

SEQ ID NO:18 xxxxxxxKxHxxxxxxxxxYxGSxxxxxxxxxxxxxxxxxxxxxxxxxGxRxxTYxxxxxxxxxxxxxN
Gxxxxxxxxxlxxxxxxxxxxxxxxxxxxxxxxxxxxxxx

C

SEQ ID NO:7

MIRTMLQGKLHRVKVTHADLHYEGSCAIDQDFLDAAGILENEA
IDIWNVTNGKRFSTYAIAAERGSRIISVNGAAAHCASVG

```
-----xxxxxxGxGxxGxxxxxLxxxx----xxxxxxxx----xxxxxxxxxxxxxxxxxxxxxxxxx------
xxxxxxxxKxxxxxxxxxxxxxxxxxxxxxN-------------Gxxxxxxxx----xxxx--------
xxxxxxxxxxxxxxxxxxxxx--xxxxxxxx------xxxxxxxxxxx-------------------------
xxxxxxxxxxxxxxxxxxKxxxNxxxxxxxxxxx---xxxxxxxxxxxxxExxxxxxxxxx----------
xxxxxxxxxxxxxxxxxx---xxxSxxxxDxxxxx--xxExxxxxxx---xxxxxxxxxx
```

B

SEQ ID NO:19

```
xxxxxxGxGxxGxxxxxLxxxxxxxxxxxxxxxxxxxxxxxxxxxxxxxxxxxKxxxxxxxxxxxxxx
xxxxxxxxxxxNGxxxxxxxxxxxxxxxxxxxxxxxxxxxxxxxxxxxxxxxxxxxxxxxxxxxxxxx
xxxxKxxxNxxxxNxxxxxxxxxxxxxxxxxxxxxxxxxxxExxxxxxxxxxxxxxxxxxxxxxxxxxxxxxSxxxDxxx
xxxxExxxxxxxxxxxxxxxxxxx
```

C

SEQ ID NO:4

MKITVLGCGAIGQLWLTALCKQGHEVQGWLRVPQPYCSVNLVETDGSIFNESLTANDPD
FLATSDLLLVTLKAWQVSDAVKSLASTLPVTTPILLIHNGMGTIEELQNIQQPLLMGTTTHA
ARRDGNVIIHVANGITHIGPARQQDGDYSYLADILQTVLPDVAWHNNIRAELWRKLAVNC
VINPLTAIWNCPNGELRHHPQEIMQICEEVAAVIEREGHHTSAEDLRDYVMQVIDATAENIS
SMLQDIRALRHTEIDYINGFLLRRARAHGIAVPENTRLFEMVKRKESEYERIGTGLPRPW

D

SEQ ID NO:4

MKITVLGCGAIGQLWLTALCKQGHEVQGWLRVPQPYCSVNLVETDGSIFNESLTANDPDF
LATSDLLLVTLKAWQVSDAVKSLASTLPVTTPILLIHNGMGTIEELQNIQQPLLMGTTTHAA
RRDGNVIIHVANGITHIGPARQQDGDYSYLADILQTVLPDVAWHNNIRAELWRKLAVNCVI
NPLTAIWNCPNGELRHHPQEIMQICEEVAAVIEREGHHTSAEDLRDYVMQVIDATAENISS
MLQDIRALRHTEIDYINGFLLRRARAHGIAVPENTRLFEMVKRKESEYERIGTGLPPRPW

PANTOTHENIC ACID BIOSYNTHESIS IN ZYMOMONAS

This application claims the benefit of U.S. Provisional Application 61/472,664, filed Apr. 7, 2011, and is incorporated by reference in its entirety.

STATEMENT OF GOVERNMENT RIGHTS

This invention was made with United States government support under Contract No. DE-FC36-07GO17056 awarded by the Department of Energy. The government has certain rights in this invention.

FIELD OF THE INVENTION

The invention relates to the fields of microbiology and genetic engineering. More specifically, *Zymomonas* was engineered for expression of enzymes to provide a pathway for pantothenate biosynthesis.

BACKGROUND OF THE INVENTION

Production of ethanol by microorganisms provides an alternative energy source to fossil fuels and is therefore an important area of current research. The bacteria *Zymomonas* naturally produces ethanol, and has been genetically engineered for improved ethanol production. Improvements include elimination of competing pathways, utilization of xylose, and better performance in medium containing biomass hydrolysate (for example: U.S. Pat. No. 7,741,119, U.S. Pat. No. 5,514,583, U.S. Pat. No. 5,712,133, WO 95/28476, Feldmann et al. (1992) Appl. Microbiol. Biotechnol. 38: 354-361, Zhang et al. (1995) Science 267:240-243, and US 2009-0203099 A1). The hydrolysate produced from lignocellulosic and cellulosic biomass can provide an abundantly available, low cost source of carbon substrates for biocatalyst fermentation to produce desired products. Biomass hydrolysate typically includes xylose, as well as inhibitors of fermentation.

For economical fermentative production, it is desired that a biocatalyst does not require addition of any costly nutrients to growth and production media. In particular, it is desired that no vitamin supplements be required for seed or production biocatalyst cultures. *Zymomonas* requires supplementation of pantothenic acid (PA; also pantothenate, vitamin $B_5$, 3-[(2,4-dihydroxy-3,3-dimethylbutanoyl)amino]propanoic acid) in growth medium, being unable to synthesize this nutrient (Seo et al. (2005) Nat. Biotechnol. 23:63-68; Nipkow et al. (1984) Appl. Microbiol. Biotechnol. 19:237-240 and references therein). PA is an important cellular component as it is required for the synthesis of coenzyme-A (CoA), a compound with many important cellular functions. For many animals it is an essential nutrient, while many plants express enzymes for the synthesis of PA.

*E. coli* is able to synthesize PA and the biosynthetic pathway is known. *E. coli* genes encoding enzymes of the pathway have been identified. Increased production of pantothenate has been achieved by overexpressing genes in the biosynthetic pathway of microorganisms that naturally produce pantothenate. Disclosed in WO 2003006664 is increasing expression of coding regions in a *Bacillus* that naturally produces D-pantothenic acid, such as ybbT, ywkA, yjmC, ytsJ, mdh, cysK, iolJ, pdhD, yuiE, dhas, adk, yusH, yqhJ, yqhK, and/or yqh-I for increased pantothenic acid production. In addition, panE, ylbQ, panB, panD, panC, ilvB, ilvN, alsS, ilvC, ilvD, serA, serC, ywpJ, and/or glyA may be increased in expression. U.S. Pat. No. 6,171,845 discloses amplification of nucleotide sequences encoding keptopantoate reductase, in particular panE, in pantothenic acid producing microorganisms. It was shown that the *Saccharomyces cerevisiae* YRH063c ORF encodes a protein having ketopantoate reductase activity by complementation of a panE-ilvC mutant in *E. coli*. US 20050089973 discloses producing panto-compounds in microorganisms where existing biosynthetic pathways are manipulated, such as by overexpressing ketopantoate reductase and aspartate alpha-decarboxylase.

US 2005221466 discloses the use of cells with alanine 2,3-aminomutase activity, which converts alpha-alanine to beta-alanine, for production of pantothenate.

There remains a need for creating *Zymomonas* strains that are able to grow and produce ethanol in the absence of externally supplied PA. These *Zymomonas* strains may be used to improve and reduce the cost of ethanol production using this biocatalyst.

SUMMARY OF THE INVENTION

The invention provides recombinant *Zymomonas* cells that express heterologous enzymes to provide a PA biosynthetic pathway.

Accordingly, the invention provides a bacterial strain of the genus *Zymomonas* comprising a heterologous nucleic acid molecule encoding a polypeptide having 2-dehydropantoate reductase activity and a heterologous nucleic acid molecule encoding a polypeptide having aspartate 1-decarboxylase activity.

In another embodiment the invention provides a process for producing a *Zymomonas* strain that synthesizes pantothenic acid comprising:
 a) providing a bacterial strain of the genus *Zymomonas*;
 b) introducing a heterologous nucleic acid molecule encoding a polypeptide having 2-dehydropantoate reductase activity; and
 c) introducing a heterologous nucleic acid molecule encoding a polypeptide having aspartate 1-decarboxylase activity;
 wherein steps b) and c) may be in either order or simultaneous and wherein 2-dehydropantoate reductase and aspartate 1-decarboxylase activities are expressed in the strain.

In yet another embodiment the invention provides a method for producing ethanol comprising:
 a) providing the recombinant bacterial strain of the genus *Zymomonas* comprising a heterologous nucleic acid molecule encoding a polypeptide having 2-dehydropantoate reductase activity and a heterologous nucleic acid molecule encoding a polypeptide having aspartate 1-decarboxylase activity; and
 b) contacting the strain of (a) with fermentation medium under conditions whereby the strain produces ethanol.

BRIEF DESCRIPTION OF THE FIGURES, BIOLOGICAL DEPOSITS AND SEQUENCE DESCRIPTIONS

Applicants have made the following biological deposits under the terms of the Budapest Treaty on the International Recognition of the Deposit of Microorganisms for the Purposes of Patent Procedure:

Information on Deposited Strains

| Depositor Identification Reference | International Depository Designation | Date of Deposit |
|---|---|---|
| Zymomonas ZW658 | ATCC No PTA-7858 | Sep. 12, 2006 |

FIG. 1 is a diagram of a pantothenic acid biosynthetic pathway with bold arrows marking activities that may be present in *Zymomonas* and arrows with "X" marking absent activities. The numbers with the arrows are EC numbers of enzymes that perform the shown reaction. Gene names associated with the EC numbers are given in some cases.

FIG. 2 shows conserved amino acid positions, using one letter abbreviations, of aspartate 1-decarboxylase polypeptides in a general structure diagram (A), in a representative sequence (B), and in the *E. coli* aspartate 1-decarboxylase amino acid sequence (C).

FIG. 3 shows conserved amino acid positions, using one letter abbreviations, of 2-dehydropantoate reductase polypeptides in a general structure diagram (A), in a representative sequence (B), in the *E. coli* 2-dehydropantoate reductase amino acid sequence based on a ten sequence alignment (C), and in the *E. coli* 2-dehydropantoate reductase amino acid sequence based on a 648 sequence alignment (D).

Figure 1:
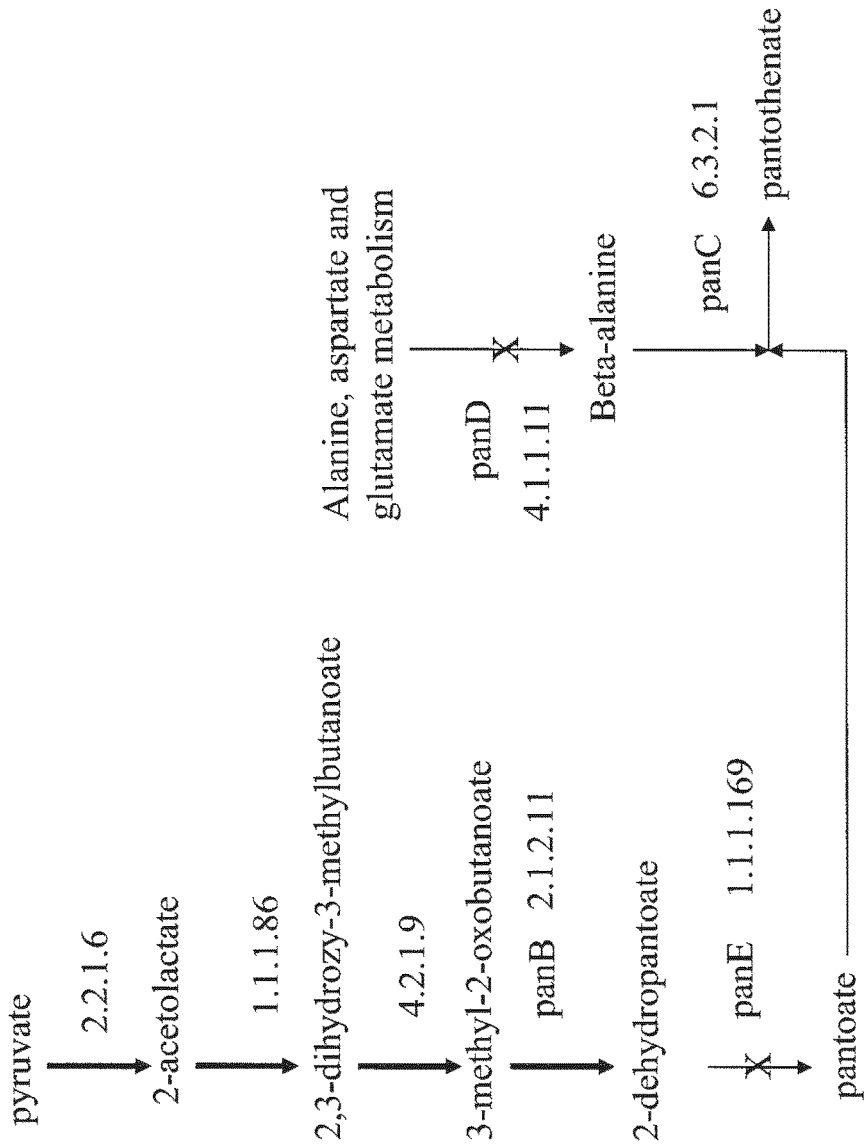

The invention can be more fully understood from the following detailed description and the accompanying sequence descriptions which form a part of this application.

The following sequences conform with 37 C.F.R. 1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (2009) and the sequence listing requirements of the EPO and PCT (Rules 5.2 and 49.5 (a-bis), and Section 208 and Annex C of the Administrative Instructions). The symbols and format used for nucleotide and amino acid sequence data comply with the rules set forth in 37 C.F.R. §1.822.

SEQ ID NO:1 is the nucleotide sequence of a synthetic chimeric *E. coli* panE and panD operon.

SEQ ID NO:2 is the nucleotide sequence of the GI promoter from the *Actinoplanes missouriensis* xylose isomerase gene.

SEQ ID NO:3 is the nucleotide sequence of the *E. coli* panE open reading frame encoding 2-dehydropantoate reductase.

SEQ ID NO:4 is the amino acid sequence of the *E. coli* panE encoded 2-dehydropantoate reductase (strain K-12 substr. MG1655; gi|16128410|ref|NP_414959.1|).

SEQ ID NO:5 is the nucleotide sequence of a stretch of DNA that is upstream from the start codon for the *Z. mobilis* glyceraldehyde 3-phosphate dehydrogenase gene that includes the Shine-Delgarno sequence SEQ ID NO:6 is the nucleotide sequence of the *E. coli* panD open reading frame encoding aspartate 1-decarboxylase.

SEQ ID NO:7 is the amino acid sequence of the *E. coli* panD encoded aspartate 1-decarboxylase.

SEQ ID NO:8 is the nucleotide sequence of a stretch of DNA that corresponds to the small, stabilizing stem-loop sequence that immediately follows the xylose isomerase (xylA) stop codon in the *E. coli* XylA/B operon.

TABLE 1

2-dehydropantoate reductases used in first alignment

| Accession number | Organism | SEQ ID NO |
|---|---|---|
| gi|53803269|ref|YP_114934.1| | *Methylococcus capsulatus* | 9 |
| gi|78223840|ref|YP_385587.1| | *Geobacter metallireducens* GS-15 | 10 |
| gi|19113647|ref|NP_596855.1| | *Schizosaccharomyces pombe* | 11 |
| gi|6321854|ref|NP_011930.1| | *Saccharomyces cerevisiae* S288c | 12 |
| gi|73538792|ref|YP_299159.1| | *Ralstonia eutropha* JMP134 | 13 |
| gi|207722086|ref|YP_002252524. | *Ralstonia solanacearum* MolK2 | 14 |
| gi|194367655|ref|YP_002030265. | *Stenotrophomonas maltophilia* R551-3 | 15 |
| gi|29376939|ref|NP_816093.1| | *Enterococcus faecalis* V583 | 16 |
| gi|16078575|ref|NP_389394.1| | *Bacillus subtilis* subsp. *subtilis* str. 168] | |

SEQ ID NO:18 is a representation of a conserved amino acid sequence for aspartate 1-decarboxylase showing the highly conserved amino acid positions, without notation of less conserved amino acid positions and with insertion positions omitted.

SEQ ID NO:19 is a representation of a conserved amino acid sequence for 2-dehydropantoate reductase showing the highly conserved amino acid positions, without notation of less conserved amino acid positions and with insertion positions omitted.

DETAILED DESCRIPTION

The following definitions may be used for the interpretation of the claims and specification:

As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

The term "invention" or "present invention" as used herein is a non-limiting term and is not intended to refer to any single embodiment of the particular invention but encompasses all possible embodiments as described in the specification and the claims.

As used herein, the term "about" modifying the quantity of an ingredient or reactant of the invention employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities. In one embodiment, the term "about" means within 10% of the reported numerical value, preferably within 5% of the reported numerical value.

"Gene" refers to a nucleic acid fragment that expresses a specific protein or functional RNA molecule, which may optionally include regulatory sequences preceding (5' non-coding sequences) and following (3' non-coding sequences) the coding sequence. "Native gene" or "wild type gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes.

"Promoter" or "Initiation control regions" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types at most times are commonly referred to as "constitutive promoters".

The term "expression", as used herein, refers to the transcription and stable accumulation of coding (mRNA) or functional RNA derived from a gene. Expression may also refer to translation of mRNA into a polypeptide. "Overexpression" refers to the production of a gene product in transgenic organisms that exceeds levels of production in normal or non-transformed organisms.

The term "transformation" as used herein, refers to the transfer of a nucleic acid fragment into a host organism, resulting in genetically stable inheritance. The transferred nucleic acid may be in the form of a plasmid maintained in the host cell, or some transferred nucleic acid may be integrated into the genome of the host cell. Host organisms containing the transformed nucleic acid fragments are referred to as "transgenic" or "recombinant" or "transformed" organisms.

The terms "plasmid" and "vector" as used herein, refer to an extra chromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "selectable marker" means an identifying factor, usually an antibiotic or chemical resistance gene, that is able to be selected for based upon the marker gene's effect, i.e., resistance to an antibiotic, wherein the effect is used to track the inheritance of a nucleic acid of interest and/or to identify a cell or organism that has inherited the nucleic acid of interest.

As used herein the term "codon degeneracy" refers to the nature in the genetic code permitting variation of the nucleotide sequence without affecting the amino acid sequence of an encoded polypeptide. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

The term "codon-optimized" as it refers to genes or coding regions of nucleic acid molecules for transformation of various hosts, refers to the alteration of codons in the gene or coding regions of the nucleic acid molecules to reflect the typical codon usage of the host organism without altering the polypeptide encoded by the DNA.

The term "carbon substrate" or "fermentable carbon substrate" refers to a carbon source capable of being metabolized by microorganisms. A type of carbon substrate is "fermentable sugars" which refers to oligosaccharides and monosaccharides that can be used as a carbon source by a microorganism in a fermentation process.

The term "lignocellulosic" refers to a composition comprising both lignin and cellulose. Lignocellulosic material may also comprise hemicellulose.

The term "cellulosic" refers to a composition comprising cellulose and additional components, which may include hemicellulose and lignin.

The term "saccharification" refers to the production of fermentable sugars from polysaccharides.

The term "pretreated biomass" means biomass that has been subjected to thermal, physical and/or chemical pretreatment to increase the availability of polysaccharides in the biomass to saccharification enzymes.

"Biomass" refers to any cellulosic or lignocellulosic material and includes materials comprising cellulose, and optionally further comprising hemicellulose, lignin, starch, oligosaccharides and/or monosaccharides. Biomass may also comprise additional components, such as protein and/or lipid. Biomass may be derived from a single source, or biomass can comprise a mixture derived from more than one source; for example, biomass could comprise a mixture of corn cobs and corn stover, or a mixture of grass and leaves. Biomass includes, but is not limited to, bioenergy crops, agricultural residues, municipal solid waste, industrial solid waste, sludge from paper manufacture, yard waste, wood and forestry waste. Examples of biomass include, but are not limited to, corn cobs, crop residues such as corn husks, corn stover, grasses, wheat, wheat straw, barley straw, hay, rice straw, switchgrass, waste paper, sugar cane bagasse, sorghum, components obtained from milling of grains, trees, branches, roots, leaves, wood chips, sawdust, shrubs and bushes, vegetables, fruits, flowers and animal manure.

"Biomass hydrolysate" refers to the product resulting from saccharification of biomass. The biomass may also be pretreated or pre-processed prior to saccharification.

The term "heterologous" means not naturally found in the location of interest. For example, a heterologous gene refers to a gene that is not naturally found in the host organism, but that is introduced into the host organism by gene transfer. For example, a heterologous nucleic acid molecule that is present in a chimeric gene is a nucleic acid molecule that is not naturally found associated with the other segments of the chimeric gene, such as the nucleic acid molecules having the coding region and promoter segments not naturally being associated with each other.

As used herein, an "isolated nucleic acid molecule" is a polymer of RNA or DNA that is single- or double-stranded, optionally containing synthetic, non-natural or altered nucleotide bases. An isolated nucleic acid molecule in the form of a polymer of DNA may be comprised of one or more segments of cDNA, genomic DNA or synthetic DNA.

A nucleic acid fragment is "hybridizable" to another nucleic acid fragment, such as a cDNA, genomic DNA, or RNA molecule, when a single-stranded form of the nucleic acid fragment can anneal to the other nucleic acid fragment under the appropriate conditions of temperature and solution ionic strength. Hybridization and washing conditions are well known and exemplified in Sambrook, J., Fritsch, E. F. and Maniatis, T. *Molecular Cloning: A Laboratory Manual*, 2$^{nd}$ ed., Cold Spring Harbor Laboratory: Cold Spring Harbor, N.Y. (1989), particularly Chapter 11 and Table 11.1 therein (entirely incorporated herein by reference). The conditions of temperature and ionic strength determine the "stringency" of the hybridization. Stringency conditions can be adjusted to screen for moderately similar fragments (such as homologous sequences from distantly related organisms), to highly similar fragments (such as genes that duplicate functional enzymes from closely related organisms). Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C. An additional set of stringent conditions include hybridization at 0.1×SSC, 0.1% SDS, 65° C. and washes with 2×SSC, 0.1% SDS followed by 0.1×SSC, 0.1% SDS, for example.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50-9.51). For hybridizations with shorter nucleic acids, i.e., oligonucleotides, the position of mismatches becomes more important, and the length of the oligonucleotide determines its specificity (see Sambrook et al., supra, 11.7-11.8). In one embodiment the length for a hybridizable nucleic acid is at least about 10 nucleotides. Preferably a minimum length for a hybridizable nucleic acid is at least about 15 nucleotides; more preferably at least about 20 nucleotides; and most preferably the length is at least about 30 nucleotides. Furthermore, the skilled artisan will recognize that the temperature and wash solution salt concentration may be adjusted as necessary according to factors such as length of the probe.

The term "complementary" is used to describe the relationship between nucleotide bases that are capable of hybridizing to one another. For example, with respect to DNA, adenosine is complementary to thymine and cytosine is complementary to guanine.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: 1.) *Computational Molecular Biology* (Lesk, A. M., Ed.) Oxford University: NY (1988); 2.) *Biocomputing: Informatics and Genome Projects* (Smith, D. W., Ed.) Academic: NY (1993); 3.) *Computer Analysis of Sequence Data, Part I* (Griffin, A. M., and Griffin, H. G., Eds.) Humania: NJ (1994); 4.) *Sequence Analysis in Molecular Biology* (von Heinje, G., Ed.) Academic (1987); and 5.) *Sequence Analysis Primer* (Gribskov, M. and Devereux, J., Eds.) Stockton: NY (1991).

Preferred methods to determine identity are designed to give the best match between the sequences tested. Methods to determine identity and similarity are codified in publicly available computer programs. Sequence alignments and percent identity calculations may be performed using the MegAlign program of the LASERGENE bioinformatics computing suite (DNASTAR Inc., Madison, Wis.).

Multiple alignment of the sequences is performed using the "Clustal method of alignment" which encompasses several varieties of the algorithm including the "Clustal V method of alignment" corresponding to the alignment method labeled Clustal V (described by Higgins and Sharp, *CABIOS.* 5:151-153 (1989); Higgins, D. G. et al., *Comput. Appl. Biosci.,* 8:189-191 (1992)) and found in the MegAlign v8.0 program of the LASERGENE bioinformatics computing suite (DNASTAR Inc.). For multiple alignments, the default values correspond to GAP PENALTY=10 and GAP LENGTH PENALTY=10. Default parameters for pairwise alignments and calculation of percent identity of protein sequences using the Clustal method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences using the Clustal V program, it is possible to obtain a "percent identity" by viewing the "sequence distances" table in the same program.

Additionally the "Clustal W method of alignment" is available and corresponds to the alignment method labeled Clustal W (described by Higgins and Sharp, CABIOS. 5:151-153 (1989); Higgins, D. G. et al., Comput. Appl. Biosci. 8:189-191 (1992); Thompson, J. D. et al, Nucleic Acid Research, 22 (22): 4673-4680, 1994) and found in the MegAlign v8.0 program of the LASERGENE bioinformatics computing suite (DNASTAR Inc.). Default parameters for multiple alignment (stated as protein/nucleic acid (GAP PENALTY=10/15, GAP LENGTH PENALTY=0.2/6.66, Delay Divergen Seqs (%)=30/30, DNA Transition Weight=0.5, Protein Weight Matrix=Gonnet Series, DNA Weight Matrix=IUB). After alignment of the sequences using the Clustal W program, it is possible to obtain a "percent identity" by viewing the "sequence distances" table in the same program.

It is well understood by one skilled in the art that many levels of sequence identity are useful in identifying polypeptides, from other species, wherein such polypeptides have the same or similar function or activity. Useful examples of percent identities include, but are not limited to: 50%, 55%, 60%, 65%, 70%, 75%, 80%, 85%, 90%, or 95%, or any integer percentage from 50% to 100% may be useful in identifying polypeptides of interest, such as 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%. Suitable nucleic acid fragments not only have the above identities but typically encode a polypeptide having at least 50 amino acids, preferably at least 100 amino acids, and more preferably at least 125 amino acids.

The term "sequence analysis software" refers to any computer algorithm or software program that is useful for the analysis of nucleotide or amino acid sequences. "Sequence analysis software" may be commercially available or independently developed. Typical sequence analysis software will include, but is not limited to: 1.) the GCG suite of programs (Wisconsin Package Version 9.0, Genetics Computer Group (GCG), Madison, Wis.); 2.) BLASTP, BLASTN, BLASTX (Altschul et al., J. Mol. Biol., 215:403-410 (1990)); 3.) DNASTAR (DNASTAR, Inc. Madison, Wis.); 4.) Sequencher (Gene Codes Corporation, Ann Arbor, Mich.); and 5.) the FASTA program incorporating the Smith-Waterman algorithm (W. R. Pearson, Comput. Methods Genome Res., [Proc. Int. Symp.] (1994), Meeting Date 1992, 111-20. Editor(s): Suhai, Sandor. Plenum: New York, N.Y.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized.

The term "E-value", as known in the art of bioinformatics, is "Expect-value" which provides the probability that a match will occur by chance. It provides the statistical significance of the match to a sequence. The lower the E-value, the more significant the hit.

Standard recombinant DNA and molecular cloning techniques used herein are well known in the art and are described by Sambrook, J. and Russell, D., Molecular Cloning: A Laboratory Manual, Third Edition, Cold Spring Harbor Laboratory Press, Cold Spring Harbor, N.Y. (2001); and by Silhavy, T. J., Bennan, M. L. and Enquist, L. W., Experiments with Gene Fusions, Cold Spring Harbor Laboratory Press, Cold Spring Harbor, N.Y. (1984); and by Ausubel, F. M. et. al., Short Protocols in Molecular Biology, 5$^{th}$ Ed. Current Protocols, John Wiley and Sons, Inc., N.Y., 2002.

Appendix 1, which is incorporated herein by reference, is a listing of Accession numbers and annotated identities of 648 2-dehydropantoate reductases of 250-350 amino acids that have an E-value of 0.00001 or smaller to the E. coli 2-dehydropantoate reductase of SEQ ID NO:4, with 95% identity and 95% overlap redundancy cutoffs.

Appendix 2, which is incorporated herein by reference, is a listing of Accession numbers and annotated identities of 693 aspartate 1-decarboxylases of 120-150 amino acids that have an E-value of 0.00001 or smaller to the E. coli aspartate 1-decarboxylase of SEQ ID NO:7, with 95% identity and 95% overlap redundancy cutoffs.

The present invention relates to engineered strains of Zymomonas that have the ability to grow without pantothenic acid (PA; also called pantothenate and vitamin $B_5$) supplementation in growth and production medium. A challenge for providing an economical process for fermentation by Zymomonas to produce ethanol is to reduce the requirement for vitamin supplementation in the medium, specifically of PA, thereby reducing the cost of growth and/or production medium. Zymomonas strains disclosed herein are genetically engineered to synthesize pantothenic acid.

Pantothenic Acid Biosynthesis

Zymomonas is known to lack the natural ability to synthesize pantothenic acid and therefore requires the presence of this vitamin in medium used for growth of this bacteria. PA is require for CoA (Coenzyme A) production, and is therefore critical for carbohydrate, protein and fatty acid metabolism.

Applicants analyzed the Zymomonas genome for the potential to encode enzymes of a pantothenic acid biosynthetic pathway. The complete sequence of the Zymomonas genome is known (Seo et al. (2005) Nat. Biotechnol. 23:63-68; NCBI Reference: NC_006526.2) and open reading frames (ORFs) have been annotated as encoding proteins with defined function where possible, based on sequence analysis. The presence of ORFs potentially encoding enzymes that could function in a pantothenic acid biosynthetic pathway was analyzed using KEGG analysis (Kyoto Encyclopedia of Genes and Genomes; Kanehisa et al. (2002) Nucleic Acids Res. 30:42-46; Kanehisa and Goto (2000) Nucleic Acids Res. 28:27-30; Kanehisa et al. (2006) Nucleic Acids Res. 34:D354-357). KEGG provides knowledge-based methods for uncovering higher-order systemic behaviors of the cell and the organism from genomic and molecular information, as stated by KEGG.

The KEGG analysis showed that the Zymomonas genome has the potential for encoding proteins with activities for some steps in a pantothenic acid biosynthetic pathway (see FIG. 1, bold arrows). The genome includes ORFs predicted to encode proteins with activities that may produce 2-dehydropantoate and L-aspartate. The EC group to which each enzyme activity in the pathway belongs, and in some cases the name of the gene encoding the enzyme, is shown in the pathway diagram of FIG. 1.

No ORF was found with the potential to encode a protein with activity that would convert 2-dehydropantoate to pantoate, and no ORF was found with the potential to encode a protein with activity that would convert L-aspartate to beta-alanine. These two steps are marked with an X in the FIG. 1 diagram. Pantoate and beta-alanine are ligated together to produce pantothenic acid in a known pantothenic acid biosynthetic pathway, such as from *E. coli*. Pantoate-beta-alanine ligase is encoded by the panC gene in many organisms, including in *E. coli*. The *Zymomonas* genome does have the potential for encoding a pantoate-beta-alanine ligase. However, the protein encoded by the ORF annotated as panC has only 46% amino acid sequence identity with the *E. coli* panC gene encoded pantoate-beta-alanine ligase. With presumably no pantoate and beta-alanine substrates available in the cell, the native function of the protein encoded by the ORF annotated as panC is unknown.

Conversion of 2-dehydropantoate to pantoate in *E. coli* is catalyzed by 2-dehydropantoate reductase, which is encoded by the panE ORF in many organisms including in *E. coli* (SEQ ID NO:3). Conversion of L-aspartate to beta-alanine is catalyzed by aspartate 1-decarboxylase, which is encoded by the panD ORF in many organisms including in *E. coli* (SEQ ID NO:6). Whether expression of these two activities in *Zymomonas* cells would confer the ability to synthesize PA was unknown, since that outcome necessitates the assumption that the presumed existing native enzymes, that sequence analysis speculates can participate in PA biosynthesis, actually do encode functional enzymes that do catalyze reactions of a portion of a PA biosynthetic pathway in *Zymomonas*.

Upon experimental analysis as disclosed herein, Applicants have discovered that *Zymomonas* cells engineered for expression of the *E. coli* panE and panD coding regions are able to grow in medium that does not contain PA. This result suggests that said *Zymomonas* cells have a complete functional PA biosynthetic pathway and synthesize PA. Further, the engineered wild type *Zymomonas* cells grow as well in medium that does not contain PA as wild type *Zymomonas* cells grow in the same medium supplemented with a non-limiting amount of PA.

In the present recombinant *Zymomonas* bacterial strains, a nucleic acid molecule encoding a polypeptide having 2-dehydropantoate reductase activity and a nucleic acid molecule encoding a polypeptide having aspartate 1-decarboxylase activity are introduced. These polypeptides are encoded by heterologous nucleic acid molecules that are introduced into the *Zymomonas* cell.

Host *Zymomonas* Cells

Heterologous nucleic acid molecules encoding polypeptides with 2-dehydropantoate reductase activity and aspartate 1-decarboxylase activity may be introduced into any strain of *Zymomonas*, such as *Zymomonas mobilis*, to create a pantothenic acid biosynthesis pathway. Wild type *Zymomonas* strains naturally produce ethanol and may be used as a host for introduction of said nucleic acid molecules. In other embodiments the *Zymomonas* host strains are recombinant strains engineered to be improved biocatalysts for ethanol production and comprise a number of genetic modifications that enhance the production of ethanol. Host strains may be strains engineered in one or more of the following ways, in any combination. *Z. mobilis* strains have been engineered to utilize xylose, a sugar found in biomass hydrolysate, for ethanol production (U.S. Pat. No. 5,514,583, U.S. Pat. No. 5,712,133, WO 95/28476, Feldmann et al. (1992) Appl. Microbiol. Biotechnol. 38: 354-361, Zhang et al. (1995) Science 267:240-243). Ethanol has been produced by genetically modified *Zymomonas* in lignocellulosic biomass hydrolysate fermentation media (U.S. Pat. No. 7,932,063). Genetically modified strains of *Z. mobilis* with improved xylose utilization and/or production of ethanol are disclosed in U.S. Pat. No. 7,223,575, U.S. Pat. No. 7,741,119, U.S. Pat. No. 7,897,396, U.S. Pat. No. 7,998,722, and WO2010/075241 (US 2011/0014670), which are herein incorporated by reference. Any of the disclosed strains, including for example ATCC31821/pZB5, ZW658 (ATCC #PTA-7858), ZW800, ZW801-4, ZW801-4::ΔhimA, AcR#3, ZW705, or other ethanol-producing strains of *Zymomonas*, may be used as host cells for expression of heterologous nucleic acid molecules encoding a polypeptide having 2-dehydropantoate reductase activity and encoding a polypeptide having aspartate 1-decarboxylase activity, which enables pantothenic acid biosynthesis.

Enzyme Activities

Any nucleic acid molecule encoding a polypeptide having 2-dehydropantoate reductase activity may be used in the present strains. Enzymes with 2-dehydropantoate reductase activity are also called 2-dehydropantoate 2-reductase, 2-oxopantoate reductase, ketopantoate reductase, ketopantoic acid reductase, KPA reductase, and KPR. The reaction catalyzed by this enzyme activity is:

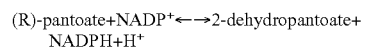

$(R)$-pantoate+$NADP^+$ ←→ 2-dehydropantoate+ $NADPH+H^+$

The 2-dehydropantoate reductase enzyme is classified as EC 1.1.1.169. A nucleic acid molecule encoding any enzyme belonging to this EC group having 2-dehydropantoate reductase activity may be used in the present strains.

Any nucleic acid molecule encoding a polypeptide having aspartate 1-decarboxylase activity may be used in the present strains. Enzymes with aspartate 1-decarboxylase activity are also called aspartate alpha-decarboxylase, L-aspartate alpha-decarboxylase, aspartic alpha-decarboxylase, L-aspartate 1-carboxy-lyase, ADC, AspDC, and Dgad2. The reaction catalyzed by this enzyme activity is:

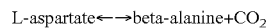

L-aspartate ←→ beta-alanine+$CO_2$

The aspartate 1-decarboxylase enzyme is classified as EC 4.1.1.11. A nucleic acid molecule encoding any enzyme belonging to this EC group having aspartate 1-decarboxylase activity may be used in the present strains. The protein translated from the *E. coli* panD gene is an inactive protein called the pi-protein (Ramjee et al (1997) Biochem. J. 323:661-669). This protein is autocatalytically self-processed into two subunits (alpha and beta) that form the active enzyme.

Polypeptides with 2-dehydropantoate reductase activity or aspartate 1-decarboxylase activity may be identified using bioinformatics and/or experimental methods. Amino acid sequences of these polypeptides can be readily found by EC number, gene name, and/or enzyme name using databases that are well known to one of skill in the art including NCBI (National Center for Biotechnology Information; Bethesda, Md.), BRENDA (The Comprehensive Enzyme Information System; Technical University of Braunschweig Dept. of Bioinformatics), and Swiss-Prot (Swiss Institute of Bioinformatics; Lausanne, Switzerland). In addition, amino acid sequences of these polypeptides can be readily found based on a known sequence using bioinformatics, including sequence analysis software such as BLAST sequence analysis using for example the *E. coli* sequences (2-dehydropantoate reductase: SEQ ID NO:4; aspartate 1-decarboxylase: SEQ ID NO:7).

The following analysis of polypeptide sequences identified a structure that is common to 2-dehydropantoate reductases belonging to EC 1.1.1.169. First the amino acid sequences of ten 2-dehydropantoate reductases (SEQ ID NOs: 9-17 and 4) with experimentally verified function and/or characterized structure as identified in the BRENDA database (BRaunschweig ENzyme Database; Cologne University BioInformatics Center; Scheer et al. (2011) Nucleic Acids Res. 39:670-676)

and the Protein Data Bank database (RCSB PDB; Berman et al. (2000) Nucleic Acids Res. 28:235-242) were aligned using Clustal W with the following parameters: Slow/Accurate Pairwise Parameters: Gap Opening=10, Gap Extend=0.1, Protein weight matrix Gonnet 250; Multiple Parameters: Gap Opening=10, Gap Extension=0.2, Protein Weight Matrix=Gonnet series. From this multiple sequence alignment, the amino acid positions with 90% to 100% conservation as a single amino acid among the ten sequences were identified and used to provide the conserved structure diagram shown in FIG. 3A. In this figure the conserved amino acids are indicated as G (glycine), L (leucine), K (lysine), N (asparagine), E (glutamic acid), S (serine), and D (aspartic acid). All of the amino acids shown are 100% conserved except the two asparagines (N) which are each 90% conserved. The dashed lines represent positions in the multiple sequence alignment where insertions and deletions, including N-terminal and C-terminal extensions, occur in one or more of the ten analyzed 2-dehydropantoate reductase amino acid sequences belonging to EC 1.1.1.169. The conserved structure of FIG. 3A is represented as a sequence in FIG. 3B (SEQ ID NO:19). In this sequence the dashed positions are omitted, and notation of other conserved amino acids, which are not as highly conserved, is omitted.

The amino acids at the conserved positions are highlighted in the $E.$ $coli$ 2-dehydropantoate reductase amino acid sequence (SEQ ID NO:4) in FIG. 3C and are G at position 7, G at position 9, G at position 12, L at position 19, K at position 72, N at position 98, G at position 99, K at position 176, N at position 180, N at position 184, E at position 210, S at position 244, D at position 248, and E at position 256. One of skill in the art will be readily able to align a candidate sequence with SEQ ID NO:4, allowing for extensions, insertions and deletions such as in positions indicated in the structure diagram of FIG. 3A, such that the presence of the conserved amino acids highlighted in FIG. 3C can be determined. Any polypeptide having at least 10, at least 11, at least 12, at least 13, or all 14 of these 14 conserved amino acids when compared to SEQ ID NO:4 and having 2-dehydropantoate reductase activity may be used in the present strains.

A BLAST search was performed using the $E.$ $coli$ 2-dehydropantoate reductase (SEQ ID NO:4) against publicly available sequences, and protein sequence matches with an E-value of 0.00001 or smaller were extracted. Matched protein sequences in the range of 250-350 amino acids were retained. Sequence redundancy was reduced to 95% identity and 95% overlap. This filtering resulted in 648 sequences, which are listed in Appendix 1 by their accession numbers. A multiple sequence alignment was performed using Clustal W with the same parameters used above. All of the amino acid positions identified above in the ten sequence alignment were also highly conserved among the 648 sequences except the L at position 19. In addition D at position 248 is replaced with S in about 4% of the sequences and the Ns at positions 180 and 184 have some variation. Thus characterization of the broader group of 2-dehydropantoate reductases provided a structure with conserved amino acids highlighted in the $E.$ $coli$ 2-dehydropantoate reductase amino acid sequence (SEQ ID NO:4) shown in FIG. 3D. The Ns at positions 180 and 184 are underlined but not bolded to represent some amino acid variation at those positions. At position 248, the presence of S instead of D is included in the conserved structure. The conserved amino acids are G at position 7, G at position 9, G at position 12, K at position 72, N at position 98, G at position 99, K at position 176, N at position 180, N at position 184, E at position 210, S at position 244, D or S at position 248, and E at position 256. One of skill in the art will be readily able to align a candidate sequence with SEQ ID NO:4, allowing for extensions, insertions and deletions such as in positions indicated in the structure diagram in FIG. 3A, such that the presence of the conserved amino acids of FIG. 3D can be determined. Any polypeptide having at least 10, at least 11, at least 12, or all 13 of these 13 conserved amino acids when compared to SEQ ID NO:4 and having 2-dehydropantoate reductase activity may be used in the present strains.

Nucleic acid molecules that may be used in the present strains include those encoding any protein having 2-dehydropantoate reductase activity, including for example: 1) those belonging to EC 1.1.1.169; 2) those with experimentally verified function and/or characterized structure (SEQ ID NOs: 9-17 and 4); 3) those having conserved structure of FIG. 3A, represented as a sequence in FIG. 3B (SEQ ID NO:19); 4) those having ten or more of the conserved amino acids highlighted in SEQ ID NO:4 in FIG. 3C; 5) those with at least about 95% sequence identity to any of the 648 proteins listed in Appendix 1; and 6) those having ten or more of the conserved amino acids highlighted in SEQ ID NO:4 in FIG. 3D.

The following analysis of polypeptide sequences identified a structure that is common to aspartate 1-decarboxylases belonging to EC 4.1.1.11. A BLAST search was performed using the $E.$ $coli$ aspartate 1-decarboxylase (SEQ ID NO:7) against publicly available sequences, and protein sequence matches with an E-value of 0.00001 or smaller were extracted. Matched protein sequences in the range of 120-150 amino acids were retained. Sequence redundancy was reduced to 95% identity and 95% overlap. This filtering resulted in 493 sequences, which are listed in Appendix 2 by their accession numbers. A multiple sequence alignment was performed using Clustal W with the following parameters: Slow/Accurate Pairwise Parameters: Gap Opening=10, Gap Extend=0.1, Protein weight matrix Gonnet 250; Multiple Parameters: Gap Opening=10, Gap Extension=0.2, Protein Weight Matrix=Gonnet series. A sequence logo was generated by LOGO extraction using Weblogo, a publicly available web based application (Crooks et al (2004) Genome Research 14:1188-1190); Schneider and Stephens (1990) Nucleic Acids Res. 18:6097-6100). According to the provided information, each logo consists of stacks of symbols, one stack for each position in the sequence. The overall height of the stack indicates the sequence conservation at that position, while the height of symbols within the stack indicates the relative frequency of each amino or nucleic acid at that position. The percent frequency of each amino acid at each position was calculated for the set of 493 sequences.

From this analysis, the most highly conserved amino acid positions were identified as those having a single amino acid occurring in at least 99% of the 493 sequences analyzed, and were used to provide the conserved structure diagram shown in FIG. 2A. In this figure the conserved amino acids are indicated as K (lysine), H (histidine), Y (tyrosine), G (glycine), S (serine), R (arginine), T (threonine), N (asparagine), and I (isoleucine). The dashed lines represent positions in the multiple sequence alignment where insertions and deletions, including N-terminal and C-terminal extensions, occur in one or more of the aligned 493 aspartate 1-decarboxylase amino acid sequences belonging to EC 4.1.1.11. The conserved structure of FIG. 2A is represented as a sequence in FIG. 2B (SEQ ID NO:18). In this sequence the dashed positions are omitted, and notation of other conserved amino acids, which are not as highly conserved, is omitted.

The amino acids at the most highly conserved positions are highlighted in the $E.$ $coli$ aspartate 1-decarboxylase amino acid sequence (SEQ ID NO:7) in FIG. 2C and are K at position 9, H at position 11, Y at position 22, G at position 24, S at position 25, G at position 52, R at position 54, T at position 57, Y at position 58, N at position 72, G at position 73, and I at position 86. One of skill in the art will be readily able to align a candidate sequence with SEQ ID NO:7, allowing for extensions, insertions and deletions such as in positions indicated in the structure diagram of FIG. 2A, such that the presence of the conserved amino acids highlighted in FIG. 2C can be determined. Any polypeptide having at least 8, at least 9, at least 10, at least 11, or all 12 of these 12 conserved amino acids when compared to SEQ ID NO:7 and having aspartate 1-decarboxylase activity may be used in the present strains.

Of the 12 most highly conserved amino acid positions shown in FIG. 2B, five of these occurred in 100% of the 493 sequences aligned. These 100% conserved positions are K at position 9, Y at position 22, G at position 24, T at position 57, and Y at position 58. In one embodiment a polypeptide that may be used has all five of these 100% highly conserved amino acid positions when compared to the E. coli aspartate 1-decarboxylase amino acid sequence (SEQ ID NO:7).

Nucleic acid molecules that may be used in the present strains include those encoding any protein having aspartate 1-decarboxylase activity, including for example: 1) those belonging to EC 4.1.1.11; 2); 2) those with 95% sequence identity to the E. coli aspartate 1-decarboxylase (SEQ ID NO:7); 3) those having conserved structure of FIG. 2A, represented as a sequence in FIG. 2B (SEQ ID NO:18); 4) those having eight or more of the conserved amino acids highlighted in SEQ ID NO:7 in FIG. 2C; 5) those having the five conserved amino acid positions K at position 9, Y at position 22, G at position 24, T at position 57, and Y at position 58, as compared to the E. coli aspartate 1-decarboxylase of SEQ ID NO:7; and 6) those with at least about 95% sequence identity to any of the 493 proteins listed in Appendix 2.

DNA sequences encoding polypeptides with 2-dehydropantoate reductase activity or aspartate 1-decarboxylase activity may also be identified using bioinformatics and/or experimental methods. Coding sequences can be found in databases including NCBI (ibid.) using gene name and/or enzyme name as is well know to one of skill in the art. Genes encoding 2-dehydropantoate reductase have multiple names, including for example panE or ApbA in E. coli, and PAN5 in Saccharomyces cerevisiae. In addition, nucleic acid sequences encoding these polypeptides can be readily found based on a known sequence using bioinformatics, including sequence analysis software such as BLAST sequence analysis using for example the E. coli sequences (2-dehydropantoate reductase: SEQ ID NO:3; aspartate 1-decarboxylase: SEQ ID NO:6). Experimental methods include those based on nucleic acid hybridization.

Nucleic acid molecules encoding 2-dehydropantoate reductase and aspartate 1-decarboxylase are found in numerous organisms including, for example, in some bacteria (excluding Zymomonas), yeast, and plants. A coding region sequence from one of these sources, which is heterologous to Zymomonas, may be used directly or it may be optimized for expression in Zymomonas. For example, it may be codon optimized for optimal protein expression in Zymomonas, and/or introns may be removed if present in a eukaryotic coding region, both of which are well known to one skilled in the art.

Expression of Enzyme Activities

For expression, a nucleic acid molecule encoding a polypeptide having 2-dehydropantoate reductase activity and a nucleic acid molecule encoding aspartate 1-decarboxylase are each constructed in a chimeric gene with operably linked promoter and typically a termination sequence. Alternatively the coding regions are constructed as part of an operon that is operably linked to a promoter and a termination sequence. In an operon, typically a ribosome binding site is located upstream of the start codons for all open reading frames in the operon. Promoters that may be used in chimeric genes and operons are promoters that are expressed in Zymomonas cells such as the promoters of Z. mobilis glyceraldehyde-3-phosphate dehydrogenase gene (GAP promoter), Z. mobilis enolase gene (ENO promoter), and the Actinoplanes missouriensis xylose isomerase gene (GI promoter). Termination signals are also those that are expressed in the target cell.

Chimeric genes or an operon for 2-dehydropantoate reductase and aspartate 1-decarboxylase expression are typically constructed in or transferred to a vector for further manipulations. Vectors are well known in the art. Particularly useful for expression in Zymomonas are vectors that can replicate in both E. coli and Zymomonas, such as pZB188 which is described in U.S. Pat. No. 5,514,583. Vectors may include plasmids for autonomous replication in a cell, and plasmids for carrying constructs to be integrated into bacterial genomes. Plasmids for DNA integration may include transposons, regions of nucleic acid sequence homologous to the target bacterial genome, or other sequences supporting integration. An additional type of vector may be a transposome produced using, for example, a system that is commercially available from EPICENTRE®. It is well known how to choose an appropriate vector for the desired target host and the desired function.

Vectors carrying the desired coding regions are introduced into Zymomonas cells using known methods such as electroporation, freeze-thaw transformation, calcium-mediated transformation, or conjugation. The coding regions may be maintained on a plasmid in the cell, or integrated into the genome. Integration methods may be used that are well known in the art such as homologous recombination, transposon insertion, or transposome insertion. In homologous recombination, DNA sequences flanking a target integration site are placed bounding a spectinomycin-resistance gene, or other selectable marker, and the chimeric genes or operon for expression, leading to insertion of the selectable marker and the expression sequences into the target genomic site. In addition, the selectable marker may be bounded by site-specific recombination sites, so that after expression of the corresponding site-specific recombinase, the resistance gene is excised from the genome.

Transformed Zymomonas strains expressing 2-dehydropantoate reductase and aspartate 1-decarboxylase may be readily identified by their ability to grow in medium lacking PA. A wild type strain of Zymomonas mobilis engineered as described in examples herein was able to grow in minimal medium lacking PA as well as the wild type strain grew with supplementation of 2.5 mg/L PA (i.e. a saturating concentration of this vitamin). In a strain of Zymomonas mobilis previously engineered for expression of xylose utilization enzyme activities and adapted to growth on xylose (U.S. Pat. No. 7,629,156), and engineered for improved ethanol production through disruption of the endogenous glucose-fructose oxidoreductase (U.S. Pat. No. 7,741,119) gene, expressing 2-dehydropantoate reductase and aspartate 1-decarboxylase also conferred the ability to grow in minimal medium lacking PA. However supplementation with p-aminobenzoic acid (PABA) was required for growth of this strain due to disruption of the pabB gene encoding p-aminobenzoate synthase subunit I, which occurred in previous engineering steps.

Ethanol Production by Pantothenic Acid Producing Strain

The present engineered Zymomonas strain expressing 2-dehydropantoate reductase and aspartate 1-decarboxylase may be used as a biocatalyst in fermentation to produce ethanol. The *Zymomonas* strain is brought in contact with medium containing a carbon substrate. Typically one or more sugars provide the carbon substrate. In one embodiment the medium may be a minimal medium with no addition of a complex ingredient that contains PA such as yeast extract, or PA itself, such that the medium lacks PA. Alternatively, the medium may contain an amount of PA that is suboptimal for growth and/or production of *Zymomonas* strains not engineered for pantothenic acid production. In one embodiment a seed culture is grown in minimal medium lacking PA or in medium having a sub-optimal amount of PA. The seed culture is then used to inoculate a larger fermentation culture. The fermentation medium may lack PA or have a sub-optimal amount of PA. Alternatively, the fermentation medium may contain an adequate amount of PA for growth and/or production of *Zymomonas* strains not engineered for pantothenic acid production.

Seed culture medium and/or fermentation medium may contain biomass hydrolysate which provides mixed sugars as a carbon source, typically including glucose, xylose, and arabinose. It is desirable that the present engineered *Zymomonas* strain also expresses enzyme activities for utilization of xylose, or of xylose and arabinose. When the mixed sugars concentration is high such that growth is inhibited, the medium may include sorbitol, mannitol, or a mixture thereof as disclosed in U.S. Pat. No. 7,629,156. Galactitol or ribitol may replace or be combined with sorbitol or mannitol. The present *Zymomonas* strain grows in the medium where fermentation occurs and ethanol is produced. The fermentation is run without supplemented air, oxygen, or other gases (which may include conditions such as anaerobic, microaerobic, or microaerophilic fermentation), for at least about 24 hours, and may be run for 30 or more hours. The timing to reach maximal ethanol production is variable, depending on the fermentation conditions. Typically, if inhibitors are present in the medium, as may be present in hydrolysate medium, a longer fermentation period is required. The fermentations may be run at temperatures that are between about 30° C. and about 37° C., at a pH of about 4.5 to about 7.5.

The present *Zymomonas* strains may be grown in medium without PA supplementation in laboratory scale fermenters, and in scaled up fermentation where commercial quantities of ethanol are produced. Where commercial production of ethanol is desired, a variety of culture methodologies may be applied. For example, large-scale production from the present *Zymomonas* strains may be produced by both batch and continuous culture methodologies. A classical batch culturing method is a closed system where the composition of the medium is set at the beginning of the culture and not subjected to artificial alterations during the culturing process. Thus, at the beginning of the culturing process the medium is inoculated with the desired organism and growth or metabolic activity is permitted to occur adding nothing to the system. Typically, however, a "batch" culture is batch with respect to the addition of carbon source and attempts are often made at controlling factors such as pH and oxygen concentration.

A variation on the standard batch system is the Fed-Batch system. Fed-Batch culture processes are also suitable for growth of the present *Zymomonas* strains and comprise a typical batch system with the exception that the substrate is added in increments as the culture progresses. Batch and Fed-Batch culturing methods are common and well known in the art and examples may be found in Biotechnology: A Textbook of Industrial Microbiology, Crueger, Crueger, and Brock, Second Edition (1989) Sinauer Associates, Inc., Sunderland, Mass., or Deshpande, Mukund V., *Appl. Biochem. Biotechnol.*, 36, 227, (1992), herein incorporated by reference.

Commercial production of ethanol may also be accomplished with a continuous culture. Continuous cultures are open systems where a culture medium is added continuously to a bioreactor and an equal amount of conditioned medium is removed simultaneously for processing. Continuous cultures generally maintain the cells at a constant high liquid phase density where cells are primarily in log phase growth.

Continuous or semi-continuous culture allows for the modulation of one factor or any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration, measured by medium turbidity, is kept constant. Continuous systems strive to maintain steady state growth conditions and thus the cell loss due to medium being drawn off must be balanced against the cell growth rate in the culture. Methods of modulating nutrients and growth factors for continuous culture processes as well as techniques for maximizing the rate of product formation are well known in the art of industrial microbiology and a variety of methods are detailed by Brock, supra.

Ethanol may be produce in simultaneous saccharification and fermentation (SSF) where pretreated biomass is saccharified producing hydrolysate containing fermentable sugars concurrently with ethanol production by the present *Zymomonas* strain.

In one embodiment the present *Zymomonas* strain is grown in shake flasks in minimal medium lacking PA at about 30° C. to about 37° C. with shaking at about 150 rpm in orbital shakers and then transferred to a 10 L seed fermentor containing a similar medium. The seed culture is grown in the seed fermentor anaerobically until $OD_{600}$ is between 3 and 6, when it is transferred to the production fermentor where the fermentation parameters are optimized for ethanol production. Typical inoculum volumes transferred from the seed tank to the production tank range from about 2% to about 20% v/v. Typical fermentation medium contains biomass hydrolysate. A final concentration of about 5 mM sorbitol or mannitol is present in the medium. The fermentation is controlled at pH 5.0-6.0 using caustic solution (such as ammonium hydroxide, potassium hydroxide, or sodium hydroxide) and either sulfuric or phosphoric acid. The temperature of the fermentor is controlled at 30° C.-35° C. In order to minimize foaming, antifoam agents (any class—silicone based, organic based etc) are added to the vessel as needed. An antimicrobial, to which the present *Zymomonas* strain has tolerance, may be used optionally to minimize contamination.

Any set of conditions described above, and additionally variations in these conditions that are well known in the art, are suitable conditions for production of ethanol by a pantothenic acid producing *Zymomonas* strain.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

General Methods

The meaning of abbreviations is as follows: "kb" means kilobase(s), "bp" means base pairs, "nts" means nucleotides, "hr" means hour(s), "min" means minute(s), "sec" means second(s), "d" means day(s), "L" means liter(s), "ml" means milliliter(s), "µL" means microliter(s), "µg" means microgram(s), "ng" means nanogram(s), "g" means gram(s), "mM" means millimolar, "µM" means micromolar, "nm" means nanometer(s), "µmol" means micromole(s), "pmol" means picomole(s), "OD" or "OD600" means optical density at 600 nm, "rpm" is revolutions per minute, "~" means approximately.

Shake Flask Experiments with Minimal Media

Unless otherwise noted, all experiments described below were conducted in shake flasks (15-ml loosely-capped, conical shaped test tubes) using PA-depleted cells and a synthetic growth medium, MM-G5, that does not contain pantothenic acid. MM-G5 is a modified version of a minimal medium that is described in Goodman et al. ((1982) Applied and Environmental Microbiology 44:496-498). It contains 50 g/L glucose, 2 g/L $KH_2PO_4$, 1 g/L $MgSO_4$ (7H2O) 2.5 g/L $(NH_4)_2SO_4$, 0.5 g/L NaCl, 50 mg/L $CaCl_2$ ($2H_2O$), 1 mg/L $Na_2MoO_4$ ($2H_2O$), 5 mg/L $FeSO_4$ ($7H_2O$), and 1 mg/L each of pyridoxine, nicotinic acid, biotin and thiamine; with the final pH brought to 5.9 with KOH, and the solution was filtered through a 0.2 µm membrane. It is also important to adjust the pH to ~5.9 with KOH after dissolving the first five ingredients in close to the final volume of deionized water to avoid precipitation of the other components. To deplete intracellular and carryover PA, cells from agar plates or glycerol stocks were inoculated into MM-G5 medium to an OD of 0.1-0.3 and the cultures were incubated at 33° C. (~150 rpm) until the cells stopped growing (~14-20 hrs). However, depending on the history of the cells, the volume and density of the initial inoculum and the extent of growth that occurred during the incubation period, complete depletion of PA may require a second growth period in fresh MM-G5 medium and/or a longer incubation period. Unless stated otherwise, spectinomycin (200 µg/ml) was included in the growth media for all experiments that were performed with the plasmid-bearing strains ZW1/PanED#1 and 801/PanED#1.

Example 1

Construction of the Synthetic GipanEpanD Operon

To complete a putative pathway for pantothenic acid (PA) biosynthesis in Z. mobilis we designed a synthetic 1620 bp DNA fragment (SEQ ID NO:1) that codes for an artificial, chimeric E. coli panE and panD operon (referred to below as either the "GipanEpanD operon" or the "GI-PanED operon"). The 5' end of the operon contains the A. missouriensis (ATCC 14538) GI promoter and there is a stretch of DNA at the 3' end that corresponds to the small, stabilizing stem-loop sequence that immediately follows the xylose isomerase (xylA) stop codon in the E. coli XylA/B operon. The synthetic DNA fragment also has NcoI and SpeI sites at its 5' end and NotI and EcoRI sites at its 3' end that can be used for cloning purposes. With reference to the DNA sequence of SEQ ID NO:1, nts 23-209 (SEQ ID NO:2) correspond to the GI promoter; nts 210-1121 (SEQ ID NO:3) correspond to the E. coli panE open reading frame (Gen Bank accession number AAC73528) that codes for 2-dehydropantoate reductase; nts 1122-1139 (SEQ ID NO:5) correspond to a stretch of DNA that is upstream from the start codon for the Z. mobilis glyceraldehyde 3-phosphate dehydrogenase gene that includes the Shine-Delgarno sequence; nts 1140-1520 (SEQ ID NO:6) correspond to the E. coli panD open reading frame (Gen Bank accession no. AAC73242) that codes for aspartate 1-decarboxylase; and nts 1543-1577 (SEQ ID NO:8) correspond to the stabilizing xylA stem-loop structure described above. The GI-PanED operon DNA fragment was synthesized by Genescript (Piscataway, N.J.).

Example 2

Construction of the Shuttle Vector Used for GI-PanED Operon Expression in Z. mobilis, and Generation of PanED Strains To introduce the GI-PanED operon into Z. mobilis, the synthetic DNA molecule described above was digested with NcoI and NotI, and the resulting fragment was ligated into the unique NcoI and NotI sites of the plasmid shuttle vector pZB188/aadA. As described in US 2009-0246876 A1, which is herein incorporated by reference, pZB188/aadA is vector pZB188 described in U.S. Pat. No. 5,514,583, which is herein incorporated by reference, which is able to replicate in Z. mobilis and E. coli since it has origins of replication for both bacterial species, with an added spectinomycin resistance DNA fragment. To generate non-methylated plasmid DNA for transformation of Z. mobilis, pZB188/aadA-GIpanEpanD was introduced into chemically competent E. coli SCS110 cells (Stratagene, San Diego, Calif.), and transformants were selected on LB medium that contained spectinomycin (100 µg/ml). Isolated non-methylated plasmid DNA was then electroporated into ZW1 (ATCC #31821) and ZW801-4. A detailed description of the construction of the xylose-utilizing recombinant strain, ZW801-4, starting from the wild type parent strain, ZW1, is provided in U.S. Pat. No. 7,741,084, which is herein incorporated by reference. Strain ZW801-4 was derived from strain ZW800, which was derived from strain ZW658, all as described in U.S. Pat. No. 7,741,084. ZW658 was constructed by integrating two operons, $P_{gap}$xylAB and $P_{gap}$taltkt, containing four xylose-utilizing genes encoding xylose isomerase (xylA), xylulokinase (xylB), transaldolase (tal), and transketolase (tkt), into the genome of ZW1 (rename of strain ZM4; ATCC #31821) via sequential transposition events to produce strain X13L3, which was renamed ZW641, and followed by adaptation on selective media containing xylose. ZW658 was deposited under the Budapest Treaty as ATCC #PTA-7858. In ZW658, the gene encoding glucose-fructose oxidoreductase was insertionally-inactivated using host-mediated, double-crossover, homologous recombination and spectinomycin resistance as a selectable marker to create strain ZW800. The spectinomycin resistance marker, which was bounded by loxP sites, was removed by site specific recombination using Cre recombinase to create strain ZW801-4. As disclosed in commonly owned and co-pending US Patent Application Publication #US 20090246846, which is herein incorporated by reference, ZW648 has much more xylose isomerase activity (about 4-fold higher) than ZW641 (represented by X13bC strain) due to a point mutation in the promoter (Pgap) that drives expression of the xylA coding region.

Transformants were selected on agar plates that contained mRM3-G5 media (50 g/L glucose, 10 g/L yeast extract (contains PA), 2 g/L $KH_2PO_4$, 1 g/L $MgSO_4$) and 200 µg/ml of spectinomycin. The resulting ZW1 and ZW801-4 strains that harbor the pZB188/aadA-GIpanEpanD shuttle vector were named ZW1/PanED #1 and 801/PanED #1, respectively. It should be noted that two primary transformants for each strain were evaluated in the shake flask experiments described below. Since both transformants behaved essentially the same in both cases, only the results that were obtained with ZW1/PanED#1 and 801/PanED#1 are presented below.

Example 3

Growth of ZW1 in MM-G5 Medium Requires PA Supplementation

Figure 4:
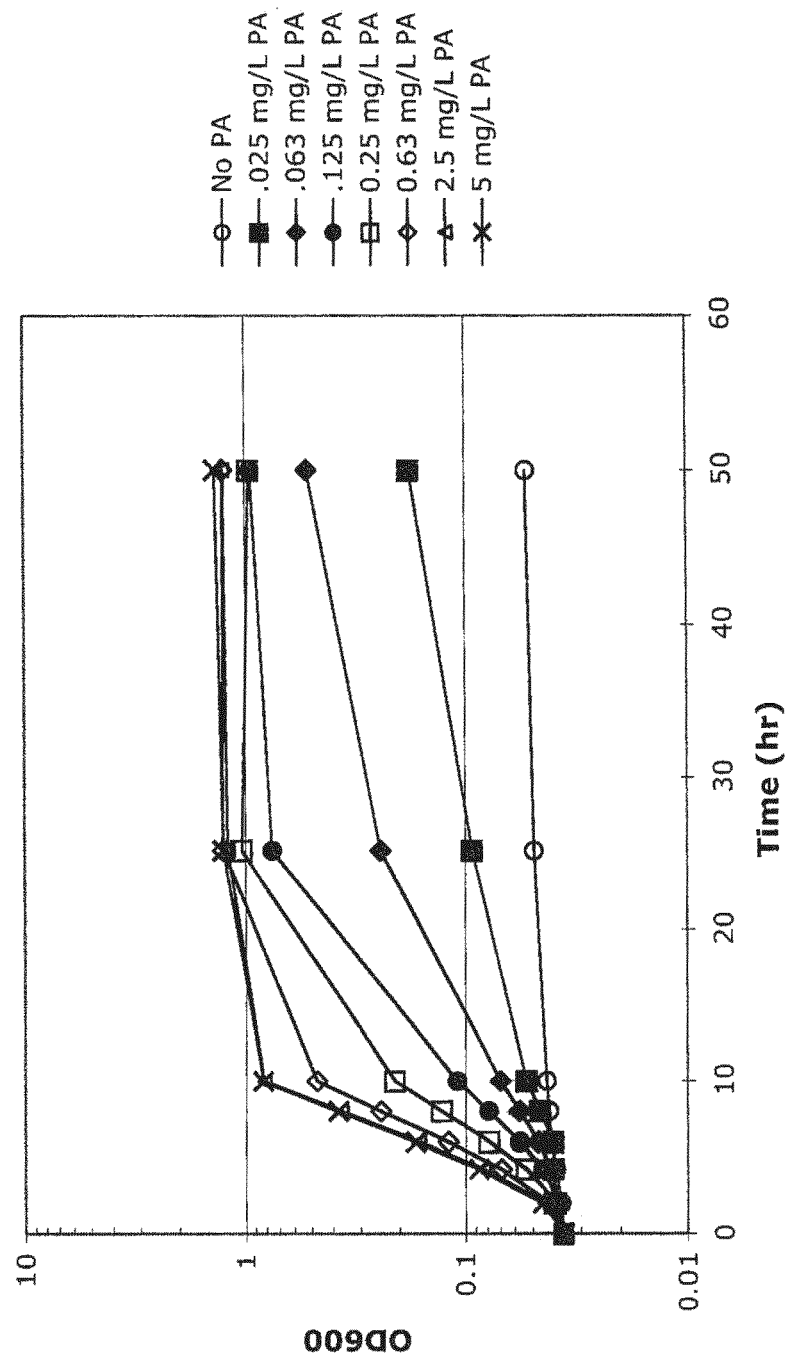
FIG. 4 shows a graph of growth curves of wild type *Zymomonas* strain ZW1 grown in minimal medium supplemented with different concentrations of pantothenic acid (PA), after a PA-depletion step.

The ZW1 strain from an mRM3-G5 plate that contained 50 g/L glucose, 10 g/L yeast extract, 2 g/L KH$_2$PO4, 1 g/L MgSO$_2$ and 1.5% agar was inoculated into 20 ml of MM-G5 (described in General Methods) and the culture was incubated for ~19 hours at 33° C. (150 rpm) to deplete carryover pantothenic acid. The OD600 increased from 0.178 to 0.408 during the incubation period. An aliquot of the PA-depleted cells was then diluted with fresh MM-G5 medium to an OD600 of 0.035, and 10-ml aliquots of the resulting culture were distributed to eight 15-ml conical test tubes that contained various amounts of pantothenic acid (0, 0.025, 0.063, 0.125, 0.25, 0.63, 2.5, or 5 mg/L, final concentrations). After this step the eight cultures were incubated at 33° C. at 150 rpm, and growth was monitored by following changes in optical density (OD) at 600 nm as a function of time. As shown in FIG. 4, both the exponential growth rate and maximum cell density increased in a dose related manner with increasing concentrations of pantothenic acid until saturation was achieved and growth was no longer limited by this vitamin. It was clear from this experiment that a concentration of ~2.5 mg/L PA or higher is able to support maximum growth of ZW1 in MM-G5 medium under the conditions employed. Growth was not observed unless the cells were supplemented with pantothenic acid.

Example 4

Effect of the Synthetic GI-PanED Operon in ZW1

Growth curves for ZW1 and ZW1/PanED #1 in the presence and absence of supplemented pantothenic acid were assayed. The protocol for this experiment was as follows. Two 10-ml MM-G5 cultures were started for each of strains ZW1 and ZW1/PanED #1. One was supplemented with PA (2.5 mg/L) while the other received an equivalent volume of sterile water. The initial ODs for all four cultures were ~0.1. After a 15-hr incubation period at 33° C. (150 rpm), aliquots of these cultures were used to start new 10-ml cultures that contained the same growth media as the original cultures; the initial OD was ~0.05 in all cases. The new cultures were incubated at 33° C. (150 rpm) and growth was monitored by OD600. The resulting exponential growth curves are shown in FIG. 5.

Figure 5A:
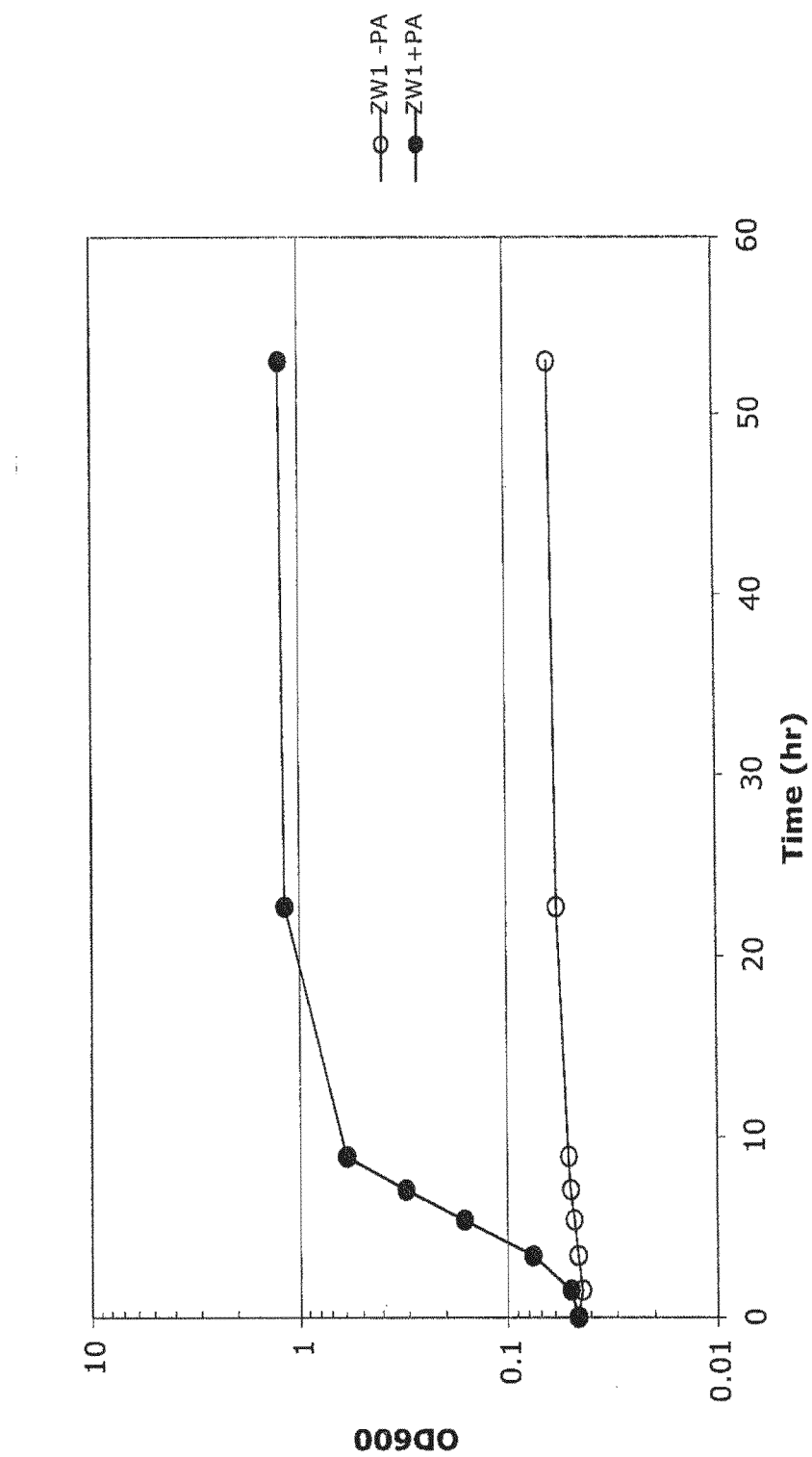
FIG. 5 shows a graph of growth curves of wild type *Zymomonas* strain ZW1(A) and strain ZW1/PanED#1 (also referred to as ZED#1) (B) grown in minimal medium with or without 2.5 mg/L pantothenic acid supplementation, after a PA-depletion step.
Figure 5B:
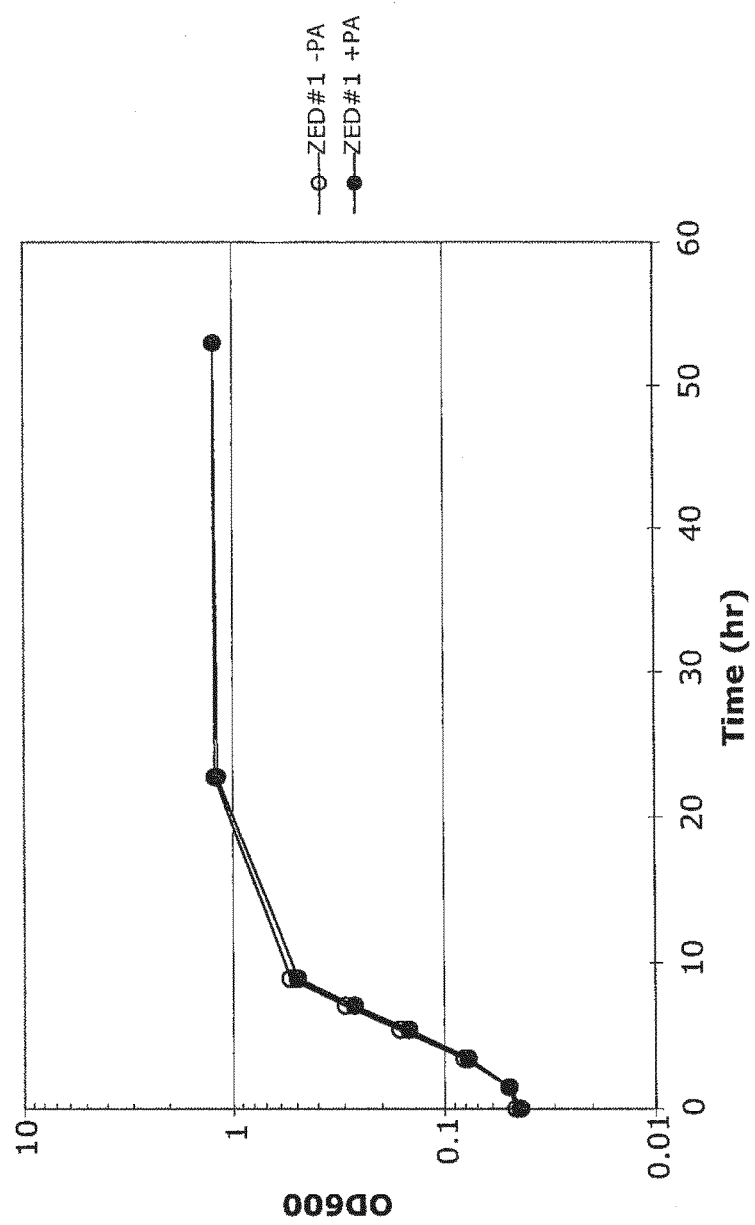

Consistent with previous results, when ZW1 was depleted of pantothenic acid in MM-G5 medium and then transferred to fresh medium that had the same composition, it failed to grow (FIG. 5A). In contrast, when ZW1 was transferred to medium that contained 2.5 mg/L of pantothenic acid, the cells grew exponentially with a doubling time of about 2 hours to a final OD of ~1.2 (FIG. 5A). Very different results were obtained with the ZW1 derivative that contains the synthetic GI-PanED operon. As shown in FIG. 5B, ZW1/PanED#1 (ZED#1) grew with the same kinetics in MM-G5 medium in the presence or absence of supplemented PA. Indeed, both growth curves for this strain were virtually identical to the growth curve for ZW1 when a saturating concentration of PA was present. These results clearly demonstrate that with introduction of panE and panD genes *Zymomonas* was able to synthesize PA, and PA was made in an amount sufficient to support the maximum growth rate in minimal medium lacking PA.

Example 5

Effect of the Synthetic GI-PanED Operon in ZW801-4

Figure 6A:
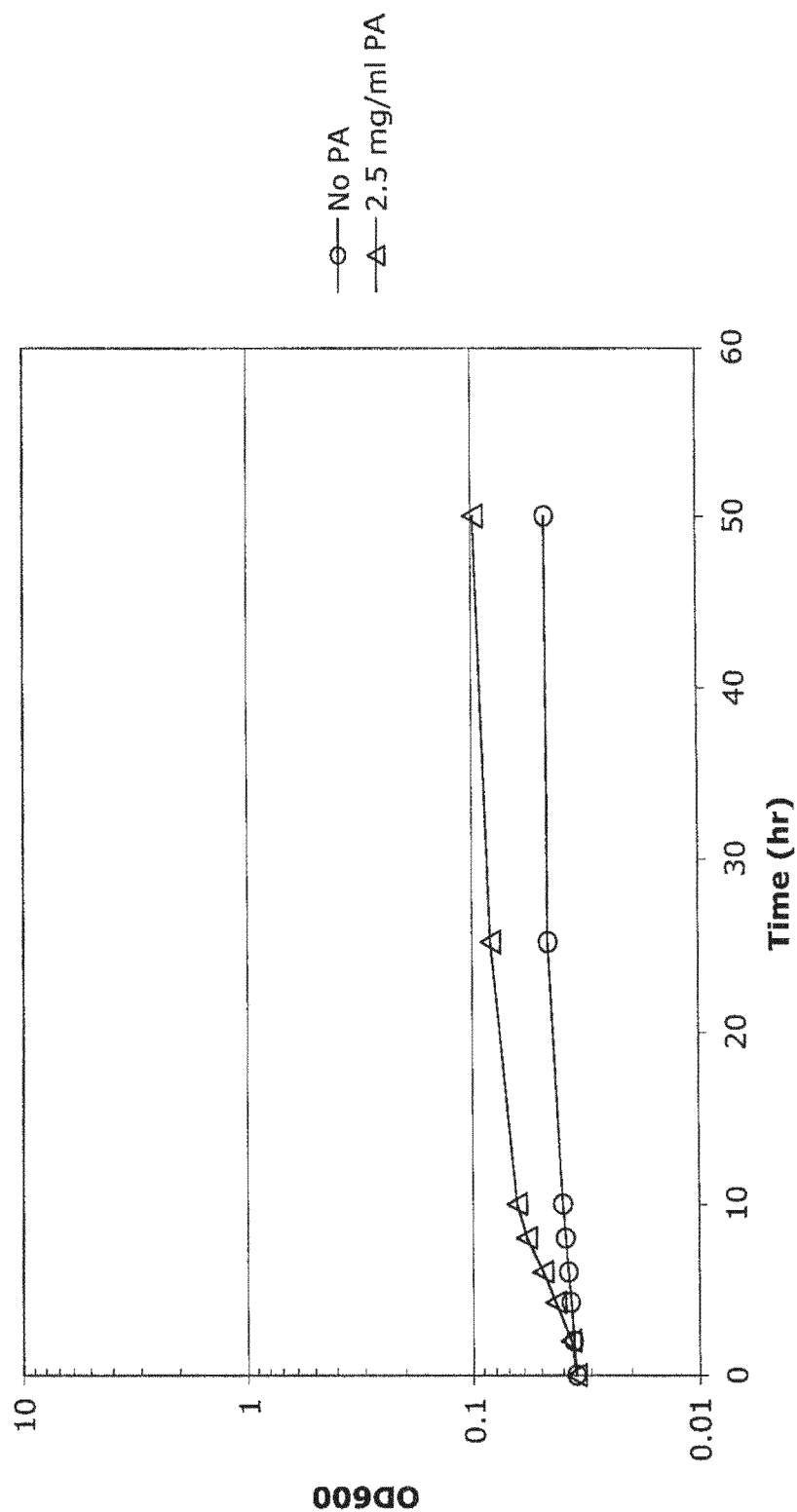
FIG. 6 shows a graph of growth curves of *Zymomonas* strain ZW801-4 in (A) minimal medium with and without 2.5 mg/L pantothenic acid supplementation, after a PA-depletion step, and in (B) minimal medium containing 15 mg/L p-aminobenzoic acid and different concentrations of pantothenic acid, after a PA-depletion step.

ZW801-4 has two vitamin requirements for growth in minimal medium. Growth experiments using ZW801-4 were carried out as described in General Methods and the resulting growth curves are shown in FIG. 6. As seen in FIG. 6A, when ZW801-4 was depleted of pantothenic acid in MM-G5 and transferred to the same medium it failed to grow, similar to the results that were obtained with ZW1. However, very little growth was also observed when pantothenic acid (2.5 mg/L) was added to the growth medium during the second incubation period (FIG. 6A). There is a genetic basis for this observation that is related to strain construction. Like other ZW641 derivatives, ZW801-4 cannot synthesize p-aminobenzoic acid (PABA), which is a vitamin that is required for folic acid biosynthesis and hence is essential. As described in U.S. Pat. No. 7,741,084, the first step in the construction of ZW641 was the integration of a synthetic P$_{gap}$taltkt operon (encoding *E. coli* transaldolase and transketolase under the control of the *Z. mobilis* P$_{gap}$ promoter) into the ZW1 chromosome. The operon was introduced by a transposon that randomly integrates into DNA, and the transposon insertion site for the strain that was selected for further metabolic engineering is in the open reading frame of the *Z. mobilis* pabB gene that codes for p-aminobenzoate synthase, subunit I, which is required for biosynthesis of PABA. The P$_{gap}$taltkt transposon insert is located between nts 102021 and 102022 of GenBank accession number AE008692, as determined by whole genome DNA sequence analysis. Since the disrupted pabB gene does not appear to be functional, ZW641 and all strains that were derived from it require two vitamins for growth in minimal media, namely PA and PABA.

Figure 6B:
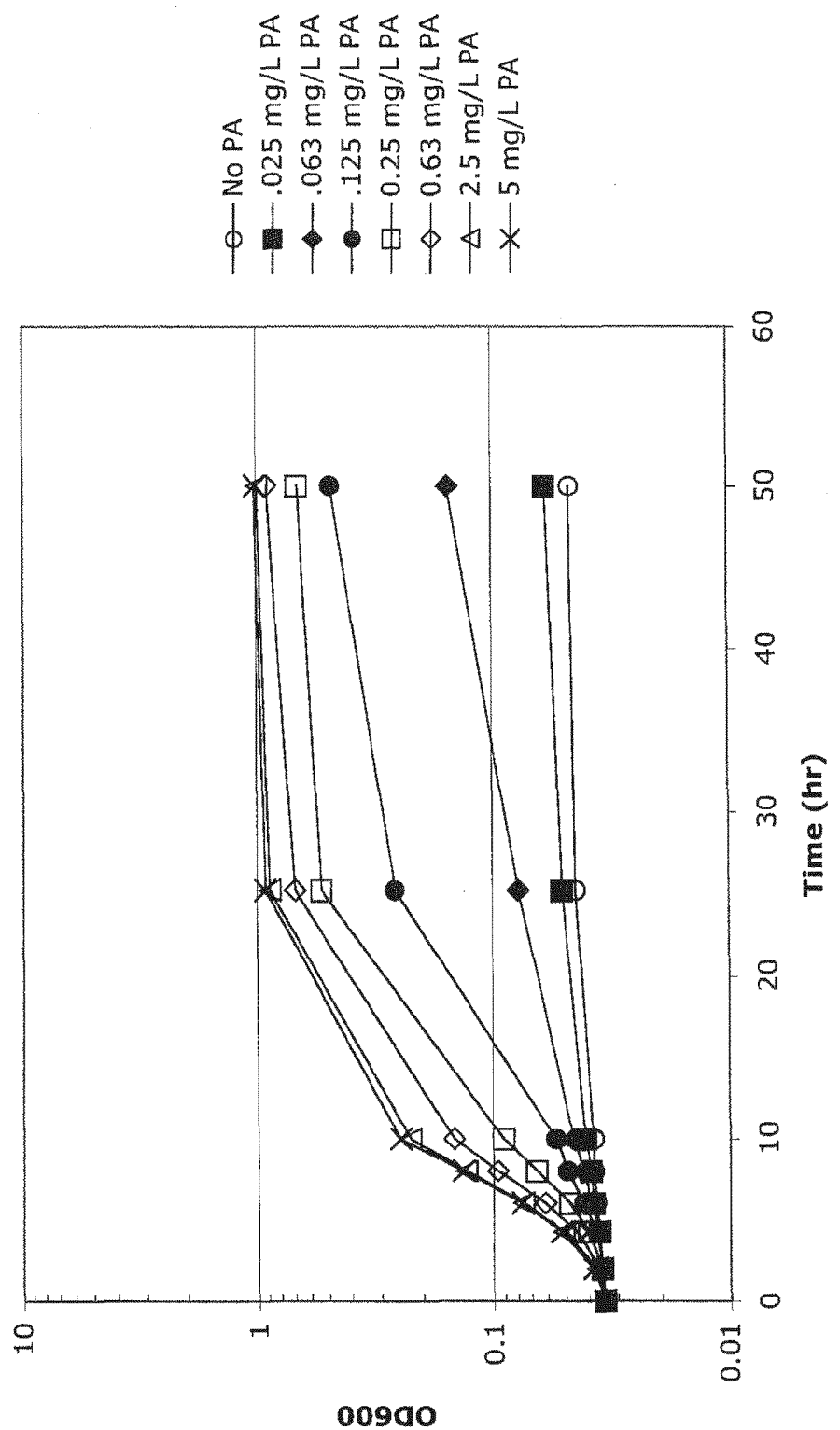

A titration experiment was conducted with ZW801-4 to determine the optimal concentration of PA for growth of in MM-G5 medium that contains a saturating concentration of PABA (15 mg/L; FIG. 6B). Strain ZW801-4 cells were inoculated into 20 ml of MM-G5 medium and the culture was incubated for ~19 hours at 33° C. (150 rpm) to deplete intracellular and carryover pantothenic acid. During the incubation period the OD increased from 0.143 to 0.364. The PA-depleted culture was then diluted with MM-G5 medium to an OD of ~0.035 and PABA was added to a final concentration of 15 mg/L. Aliquots (10 ml) of the cell suspension were distributed to eight 15-ml conical tubes that contained various concentrations of PA (ranging from 0-5 mg/L), and the resulting cultures were incubated at 33° C. (150 rpm) to monitor growth. As shown in FIG. 6B, the optimal concentration of PA for growth of ZW801-4 in MM-G5 medium that contains a saturating concentration of PABA was ~2.5 mg/L, similar to the requirement for ZW1 (FIG. 4).

GI-PanED Operon in ZW801-4

Each of strains ZW801-4 and ZW801-4/PanED#1 was inoculated into 10 ml of MM-G5 and the cultures were incubated at 33° C. for 15 hrs to deplete pantothenic acid and partially deplete PABA; the initial OD was ~0.1 in both cases. Following this step the cultures were diluted with the same growth medium to an OD of ~0.04, and quadruplicate 10-ml aliquots of each cell suspension were distributed to eight 15-ml conical tubes. The tubes were then supplemented with PA, PABA both vitamins, or neither, and the resulting cultures were incubated at 33° C. to monitor growth at 600 nm. The final concentrations of PA and PABA when present were 2.5 mg/L and 15 mg/L, respectively, and the no vitamin control cultures received an equivalent volume of sterile water. The resulting growth curves are shown in FIG. 7.

Figure 7A:
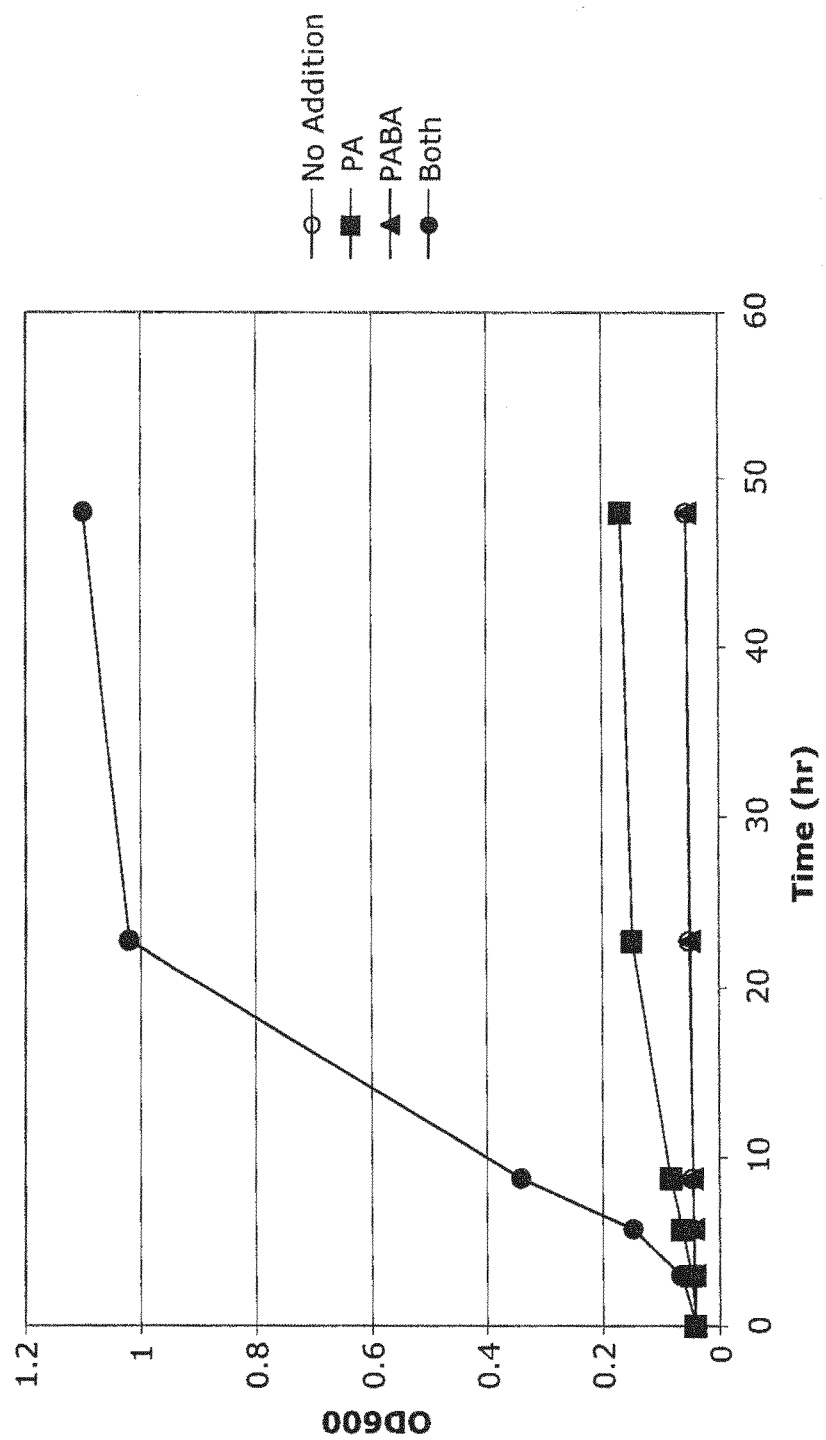
FIG. 7 shows a graph of growth curves of *Zymomonas* strains ZW801-4 (A) and ZW801-4/PanED#1(B) grown in minimal medium supplemented with 15 mg/L p-aminobenzoic acid (PABA), 2.5 mg/L pantothenic acid, both compounds, or neither, after a PA-depletion step.
Figure 7B:
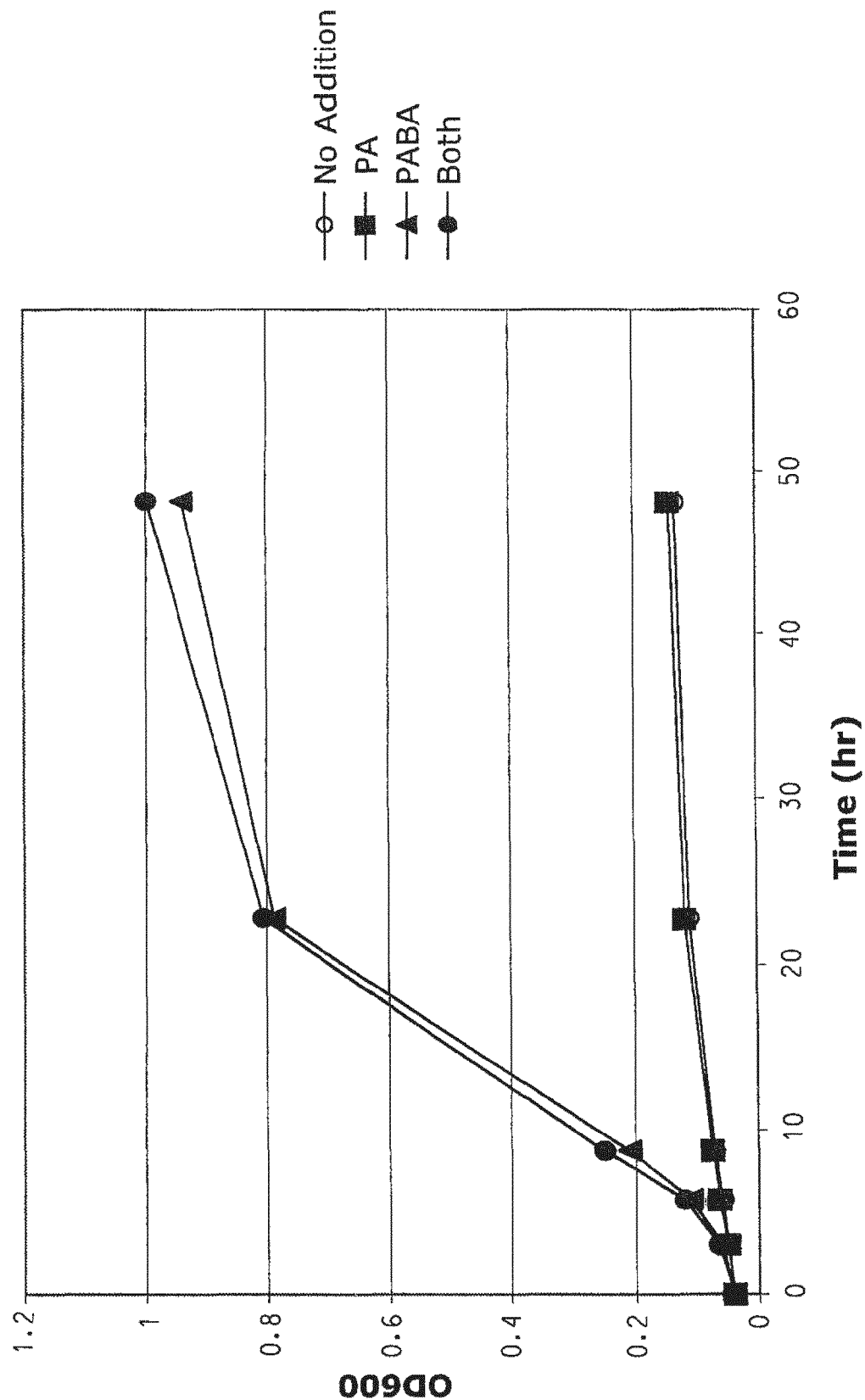

Consistent with previous results, ZW801-4 only grew when PA and PABA were both added to the growth medium (FIG. 7A). The small amount of growth that occurred in the culture that was only supplemented with PA is the result of carryover PABA, since there is always a small amount of residual PABA after the PA-depletion step during the first incubation period in MM-G5 medium (i.e. the cells use up all the PA before they run out of PABA). In contrast to the above results, the ZW801-4 strain that contained the synthetic GI-PanED operon only required PABA for growth (FIG. 7B)) since it was able to synthesize pantothenic acid.

Note that the ZW801-4 culture that was supplemented with both vitamins grew slightly better in MM-G5 medium than the corresponding culture of ZW801-4/PanED#1 (FIG. 7A versus 7B). The most likely explanation for this result is "plasmid burden", which is often observed with *Z. mobilis* and other bacterial strains (Kim et al, (2000) Applied and Environmental Microbiology 66:186-193 and references therein). This phenomenon, whereby energy that would otherwise be available for growth is diverted to plasmid replication and maintenance, would likely be far more pronounced in minimal medium compared to rich medium.

The key finding in this experiment is that ZW801-4/PanED#1 grew with the same kinetics and to the same cell density in the presence and absence of added pantothenic acid when the growth medium contained a saturating concentration of PABA. Taken together the above results clearly indicate that co-expression of the *E. coli* panE and panD coding regions in wild type and recombinant strains of *Z. mobilis* allowed growth under conditions where pantothenic acid was limiting.

APPENDIX 1

Polypeptides of 250-350 Amino Acids with E Value of 0.00001 or Smaller to SEQ ID NO:4 with 95% Identity and 95% Overlap Redundancy Cut-offs >gi|16128410|ref|NP_414959.1| 2-dehydropantoate reductase, NADPH-specific [*Escherichia coli* str. K-12 substr MG1655]
>gi|126031569|pdb|2OFP|A Chain A, Crystal Structure Of *Escherichia Coli* Ketopantoate Reductase In A Ternary Complex With Nadp+ And Pantoate
>gi|157146959|ref|YP_001454278.1| 2-dehydropantoate 2-reductase [*Citrobacter koseri* ATCC BAA-895]
>gi|168232408|ref|ZP_02657466.1| 2-dehydropantoate 2-reductase [*Salmonella enterica* subsp. *enterica* serovar Kentucky str. CDC 191]
>gi|283764244|ref|YP_003364109.1| 2-dehydropantoate 2-reductase [*Citrobacter rodentium* ICC168]
>gi|283834256|ref|ZP_06353997.1| 2-dehydropantoate 2-reductase [*Citrobacter youngae* ATCC 29220]
>gi|261341017|ref|ZP_05968875.1| 2-dehydropantoate 2-reductase [*Enterobacter cancerogenus* ATCC 35316]
>gi|296101546|ref|YP_003611692.1| 2-dehydropantoate 2-reductase [*Enterobacter cloacae* subsp. *cloacae* ATCC 13047]
>gi|146310553|ref|YP_001175627.1| 2-dehydropantoate 2-reductase [*Enterobacter* sp. 638]
>gi|206579053|ref|YP_002240106.1| 2-dehydropantoate 2-reductase [*Klebsiella pneumoniae* 342]
>gi|161615377|ref|YP_001589342.1| hypothetical protein SPAB_03148 [*Salmonella enterica* subsp. *enterica* serovar Paratyphi B str. SPB7]
>gi|311280686|ref|YP_003942917.1| 2-dehydropantoate 2-reductase [*Enterobacter cloacae* SCF1]
>gi|493074|gb|AAA56681.1| ApbA protein [*Salmonella enterica* subsp. *enterica* serovar *Typhimurium*]
>gi|260596793|ref|YP_003209364.1| 2-dehydropantoate 2-reductase [*Cronobacter turicensis* z3032]
>gi|156935026|ref|YP_001438942.1| hypothetical protein ESA_02877 [*Cronobacter sakazakii* ATCC BAA-894]
>gi|188534647|ref|YP_001908444.1| 2-dehydropantoate 2-reductase (KPA reductase) [*Erwinia tasmaniensis* Et1/99]
>gi|157369326|ref|YP_001477315.1| 2-dehydropantoate 2-reductase [*Serratia proteamaculans* 568]
>gi|259909271|ref|YP_002649627.1| 2-dehydropantoate 2-reductase (KPA reductase) [*Erwinia pyrifoliae* Ep1/96]
>gi|317047160|ref|YP_004114808.1| 2-dehydropantoate 2-reductase [*Pantoea* sp. At-9b]
>gi|270263558|ref|ZP_06191827.1| 2-dehydropantoate 2-reductase [*Serratia odorifera* 4Rx13]
>gi|304395487|ref|ZP_07377370.1| 2-dehydropantoate 2-reductase [*Pantoea* sp. aB]
>gi|300715579|ref|YP_003740382.1| 2-dehydropantoate 2-reductase (KPA reductase) [*Erwinia billingiae* Eb661]
>gi|293392557|ref|ZP_06636877.1| 2-dehydropantoate 2-reductase [*Serratia odorifera* DSM 4582]
>gi|318604615|emb|CBY26113.1| 2-dehydropantoate 2-reductase [*Yersinia enterocolitica* subsp. *palearctica* Y11]
>gi|238754221|ref|ZP_04615578.1| 2-dehydropantoate 2-reductase [*Yersinia ruckeri* ATCC 29473]
>gi|238783622|ref|ZP_04627643.1| 2-dehydropantoate 2-reductase [*Yersinia bercovieri* ATCC 43970]
>gi|238750992|ref|ZP_04612488.1| 2-dehydropantoate 2-reductase [*Yersinia rohdei* ATCC 43380]
>gi|238791418|ref|ZP_04635056.1| 2-dehydropantoate 2-reductase [*Yersinia intermedia* ATCC 29909]
>gi|22124921|ref|NP_668344.1| 2-dehydropantoate 2-reductase [*Yersinia pestis* KIM 10]
>gi|291616534|ref|YP_003519276.1| PanE [*Pantoea ananatis* LMG 20103]
>gi|227113453|ref|ZP_03827109.1| 2-dehydropantoate 2-reductase [*Pectobacterium carotovorum* subsp. *brasiliensis* PBR1692]
>gi|261822519|ref|YP_003260625.1| 2-dehydropantoate 2-reductase [*Pectobacterium wasabiae* WPP163]
>gi|238759275|ref|ZP_04620442.1| 2-dehydropantoate 2-reductase [*Yersinia aldovae* ATCC 35236]
>gi|271499585|ref|YP_003332610.1| 2-dehydropantoate 2-reductase [*Dickeya dadantii* Ech586]
>gi|322834061|ref|YP_004214068.1| 2-dehydropantoate 2-reductase [*Rahnella* sp. Y9602]
>gi|317492927|ref|ZP_07951351.1| 2-dehydropantoate 2-reductase [*Enterobacteriaceae bacterium* 9_2_54FAA]
>gi|307129910|ref|YP_003881926.1| 2-dehydropantoate reductase, NADPH-specific [*Dickeya dadantii* 3937]
>gi|251790660|ref|YP_003005381.1| 2-dehydropantoate 2-reductase [*Dickeya zeae* Ech1591]
>gi|242240305|ref|YP_002988486.1| 2-dehydropantoate 2-reductase [*Dickeya dadantii* Ech703]

>gi|269138340|ref|YP_003295040.1| 2-dehydropantoate 2-reductase [*Edwardsiella tarda* EIB202]
>gi|85058639|ref|YP_454341.1| 2-dehydropantoate 2-reductase [*Sodalis glossinidius* str. 'morsitans']
>gi|290474680|ref|YP_003467560.1| 2-dehydropantoate 2-reductase [*Xenorhabdus bovienii* SS-2004]
>gi|294635317|ref|ZP_06713814.1| 2-dehydropantoate 2-reductase [*Edwardsiella tarda* ATCC 23685]
>gi|300722004|ref|YP_003711284.1| 2-dehydropantoate 2-reductase, NADPH-specific, alternative pyrimidine biosynthesis [*Xenorhabdus nematophila* ATCC 19061]
>gi|253990908|ref|YP_003042264.1| 2-dehydropantoate 2-reductase [*Photorhabdus asymbiotica* subsp. *asymbiotica* ATCC 43949]
>gi|268592049|ref|ZP_06126270.1| 2-dehydropantoate 2-reductase [*Providencia rettgeri* DSM 1131]
>gi|261346377|ref|ZP_05974021.1| 2-dehydropantoate 2-reductase [*Providencia rustigianii* DSM 4541]
>gi|37527742|ref|NP_931087.1| 2-dehydropantoate 2-reductase [*Photorhabdus luminescens* subsp. *laumondii* TTO1]
>gi|226329087|ref|ZP_03804605.1| hypothetical protein PROPEN_02990 [*Proteus penneri* ATCC 35198]
>gi|183601047|ref|ZP_02962540.1| hypothetical protein PROSTU_04668 [*Providencia stuartii* ATCC 25827]
>gi|212709183|ref|ZP_03317311.1| hypothetical protein PROVALCAL_00216 [*Providencia alcalifaciens* DSM 30120]
>gi|227358117|ref|ZP_03842458.1| 2-dehydropantoate 2-reductase [*Proteus mirabilis* ATCC 29906]
>gi|94677011|ref|YP_588722.1| 2-dehydropantoate 2-reductase [*baumannia cicadellinicola* str. Hc (*Homalodisca coagulata*)]
>gi|32490895|ref|NP_871149.1| hypothetical protein WGLp146 [*Wigglesworthia glossinidia* endosymbiont of *Glossina brevipalpis*]
>gi|292493929|ref|YP_003533073.1| 2-dehydropantoate 2-reductase [*Candidatus Riesia pediculicola* USDA]
>gi|89073146|ref|ZP_01159685.1| 2-dehydropantoate 2-reductase [*Photobacterium* sp. SKA34]
>gi|90579842|ref|ZP_01235650.1| 2-dehydropantoate 2-reductase [*Vibrio angustum* S14]
>gi|90410911|ref|ZP_01218925.1| 2-dehydropantoate 2-reductase [*Photobacterium profundum* 3TCK]
>gi|54308007|ref|YP_129027.1| 2-dehydropantoate 2-reductase [*Photobacterium profundum* SS9]
>gi|323491692|ref|ZP_08096870.1| 2-dehydropantoate 2-reductase [*Vibrio brasillensis* LMG 20546]
>gi|148979964|ref|ZP_01815804.1| 2-dehydropantoate 2-reductase [*Vibrionales bacterium* SWAT-3]
>gi|153217426|ref|ZP_01951177.1| 2-dehydropantoate 2-reductase [*Vibrio cholerae* 1567]
>gi|91223419|ref|ZP_01258684.1| 2-dehydropantoate 2-reductase [*Vibrio alginolyticus* 12G01]
>gi|28899137|ref|NP_798742.1| 2-dehydropantoate 2-reductase [*Vibrio parahaemolyticus* RIMD 2210633]
>gi|229521149|ref|ZP_04410569.1| 2-dehydropantoate 2-reductase [*Vibrio cholerae* TM 11079-80]
>gi|153825996|ref|ZP_01978663.1| 2-dehydropantoate 2-reductase [*Vibrio cholerae* MZO-2]
>gi|229513947|ref|ZP_04403409.1| 2-dehydropantoate 2-reductase [*Vibrio cholerae* TMA 21]
>gi|261211422|ref|ZP_05925710.1| 2-dehydropantoate 2-reductase [*Vibrio* sp. RC341]
>gi|197335509|ref|YP_002155481.1| 2-dehydropantoate 2-reductase [*Vibrio fischeri* MJ11]
>gi|258620951|ref|ZP_05715985.1| 2-dehydropantoate 2-reductase [*Vibrio mimicus* VM573]
>gi|59711325|ref|YP_204101.1| 2-dehydropantoate 2-reductase [*Vibrio fischeri* ES114]
>gi|319999267|gb|AAO10217.2| 2-dehydropantoate 2-reductase [*Vibrio vulnificus*]
>gi|258627307|ref|ZP_05722091.1| 2-dehydropantoate 2-reductase [*Vibrio mimicus* VM603]
>gi|84388932|ref|ZP_00991140.1| 2-dehydropantoate 2-reductase [*Vibrio splendidus* 12B01]
>gi|269103241|ref|ZP_06155936.1| 2-dehydropantoate 2-reductase [*Photobacterium damselae* subsp. *damselae* CIP 102761]
>gi|269960517|ref|ZP_06174889.1| conserved hypothetical protein [*Vibrio harveyi* 1DA3]
>gi|297580947|ref|ZP_06942872.1| 2-dehydropantoate 2-reductase [*Vibrio cholerae* RC385]
>gi|209694510|ref|YP_002262438.1| 2-dehydropantoate 2-reductase [*Aliivibrio salmonicida* LFI1238]
>gi|163802380|ref|ZP_02196274.1| 2-dehydropantoate 2-reductase [*Vibrio* sp. AND4]
>gi|260773428|ref|ZP_05882344.1| 2-dehydropantoate 2-reductase [*Vibrio metschnikovii* CIP 69.14]
>gi|153833983|ref|ZP_01986650.1| 2-dehydropantoate 2-reductase [*Vibrio harveyi* HY01]
>gi|149189154|ref|ZP_01867442.1| 2-dehydropantoate 2-reductase [*Vibrio shilonii* AK1]
>gi|260775331|ref|ZP_05884228.1| 2-dehydropantoate 2-reductase [*Vibrio coralliilyticus* ATCC BAA-450]
>gi|261253775|ref|ZP_05946348.1| 2-dehydropantoate 2-reductase [*Vibrio orientalis* CIP 102891]
>gi|312884367|ref|ZP_07744073.1| 2-dehydropantoate 2-reductase [*Vibrio caribbenthicus* ATCC BAA-2122]
>gi|156975556|ref|YP_001446463.1| 2-dehydropantoate 2-reductase [*Vibrio harveyi* ATCC BAA-1116]
>gi|218708705|ref|YP_002416326.1| 2-dehydropantoate 2-reductase [*Vibrio splendidus* LGP32]
>gi|308125784|ref|ZP_05777325.2| 2-dehydropantoate 2-reductase [*Vibrio parahaemolyticus* K5030]
>gi|323497930|ref|ZP_08102939.1| 2-dehydropantoate 2-reductase [*Vibrio sinaloensis* DSM 21326]
>gi|315181023|gb|ADT87937.1| 2-dehydropantoate 2-reductase [*Vibrio furnissii* NCTC 11218]
>gi|86145667|ref|ZP_01063997.1| 2-dehydropantoate 2-reductase [*Vibrio* sp. MED222]
>gi|237807568|ref|YP_002892008.1| 2-dehydropantoate 2-reductase [*Tolumonas auensis* DSM 9187]
>gi|254507837|ref|ZP_05119967.1| 2-dehydropantoate 2-reductase [*Vibrio parahaemolyticus* 16]
>gi|145300108|ref|YP_001142949.1| 2-dehydropantoate 2-reductase [*Aeromonas salmonicida* subsp. *salmonicida* A449]
>gi|117618856|ref|YP_855669.1| 2-dehydropantoate 2-reductase [*Aeromonas hydrophila* subsp. *hydrophila* ATCC 7966]
>gi|109897687|ref|YP_660942.1| 2-dehydropantoate 2-reductase [*Pseudoalteromonas atlantica* T6c]
>gi|167625112|ref|YP_001675406.1| 2-dehydropantoate 2-reductase [*Shewanella halifaxensis* HAW-EB4]
>gi|149911104|ref|ZP_01899731.1| 2-dehydropantoate 2-reductase [*Moritella* sp. PE36]
>gi|254480183|ref|ZP_05093431.1| 2-dehydropantoate 2-reductase [marine gamma proteobacterium HTCC2148]
>gi|116052432|ref|YP_792743.1| 2-dehydropantoate 2-reductase [*Pseudomonas aeruginosa* UCBPP-PA14]
>gi|221134751|ref|ZP_03561054.1| 2-dehydropantoate 2-reductase [*Glaciecola* sp. HTCC2999]

>gi|157962933|ref|YP_001502967.1| 2-dehydropantoate 2-reductase [*Shewanella pealeana* ATCC 700345]
>gi|157376577|ref|YP_001475177.1| 2-dehydropantoate 2-reductase [*Shewanella sediminis* HAW-EB3]
>gi|294142129|ref|YP_003558107.1| 2-dehydropantoate 2-reductase [*Shewanella violacea* DSS12]
>gi|90409046|ref|ZP_01217173.1| ketopantoate reductase [*Psychromonas* sp. CNPT3]
>gi|120553890|ref|YP_958241.1| 2-dehydropantoate 2-reductase [*Marinobacter aquaeolei* VT8]
>gi|153002110|ref|YP_001367791.1| 2-dehydropantoate 2-reductase [*Shewanella baltica* OS185]
>gi|104783439|ref|YP_609937.1| 2-dehydropantoate 2-reductase [*Pseudomonas entomophila* L48]
>gi|163750766|ref|ZP_02158001.1| 2-dehydropantoate 2-reductase [*Shewanella benthica* KT99]
>gi|71278126|ref|YP_267839.1| 2-dehydropantoate 2-reductase [*Colwellia psychrerythraea* 34H]
>gi|152984521|ref|YP_001350304.1| 2-dehydropantoate 2-reductase [*Pseudomonas aeruginosa* PA7]
>gi|146291921|ref|YP_001182345.1| 2-dehydropantoate 2-reductase [*Shewanella putrefaciens* CN-32]
>gi|307304742|ref|ZP_07584492.1| 2-dehydropantoate 2-reductase [*Shewanella baltica* BA175]
>gi|196157569|ref|YP_002127058.1| 2-dehydropantoate 2-reductase [*Alteromonas macleodii* 'Deep ecotype']
>gi|146283482|ref|YP_001173635.1| 2-dehydropantoate 2-reductase [*Pseudomonas stutzeri* A1501]
>gi|226943468|ref|YP_002798541.1| 2-dehydropantoate 2-reductase [*Azotobacter vinelandii* DJ]
>gi|229592315|ref|YP_002874434.1| 2-dehydropantoate 2-reductase [*Pseudomonas fluorescens* SBW25]
>gi|126667530|ref|ZP_01736500.1| 2-dehydropantoate 2-reductase [*Marinobacter* sp. ELB17]
>gi|148549578|ref|YP_001269680.1| 2-dehydropantoate 2-reductase [*Pseudomonas putida* F1]
>gi|312962772|ref|ZP_07777260.1| ketopantoate reductase ApbA [*Pseudomonas fluorescens* WH6]
>gi|77460643|ref|YP_350150.1| 2-dehydropantoate 2-reductase [*Pseudomonas fluorescens* Pf0-1]
>gi|91792130|ref|YP_561781.1| 2-dehydropantoate 2-reductase [*Shewanella denitrificans* OS217]
>gi|167035489|ref|YP_001670720.1| 2-dehydropantoate 2-reductase [*Pseudomonas putida* GB-1]
>gi|89093977|ref|ZP_01166922.1| 2-dehydropantoate 2-reductase [*Oceanospirillum* sp. MED92]
>gi|324101840|gb|EGB99375.1| 2-dehydropantoate 2-reductase [*Pseudomonas* sp. TJI-51]
>gi|83644750|ref|YP_433185.1| 2-dehydropantoate 2-reductase [*Hahella chejuensis* KCTC 2396]
>gi|146305972|ref|YP_001186437.1| 2-dehydropantoate 2-reductase [*Pseudomonas mendocina* ymp]
>gi|170727979|ref|YP_001762005.1| 2-dehydropantoate 2-reductase [*Shewanella woodyi* ATCC 51908]
>gi|170720144|ref|YP_001747832.1| 2-dehydropantoate 2-reductase [*Pseudomonas putida* W619]
>gi|113971493|ref|YP_735286.1| 2-dehydropantoate 2-reductase [*Shewanella* sp. MR-4]
>gi|119945922|ref|YP_943602.1| 2-dehydropantoate 2-reductase [*Psychromonas ingrahamii* 37]
>gi|288573554|ref|ZP_06391911.1| 2-dehydropantoate 2-reductase [*Dethiosulfovibrio peptidovorans* DSM 11002]
>gi|117919232|ref|YP_868424.1| 2-dehydropantoate 2-reductase [*Shewanella* sp. ANA-3]
>gi|311694203|gb|ADP97076.1| 2-dehydropantoate 2-reductase [marine bacterium HP15]
>gi|149378127|ref|ZP_01895846.1| 2-dehydropantoate 2-reductase [*Marinobacter algicola* DG893]
>gi|253576112|ref|ZP_04853444.1| 2-dehydropantoate 2-reductase [*Paenibacillus* sp. oral taxon 786 str. D14]
>gi|70732101|ref|YP_261857.1| 2-dehydropantoate 2-reductase [*Pseudomonas fluorescens* Pf-5]
>gi|304310467|ref|YP_003810065.1| 2-dehydropantoate 2-reductase [Ketopantoate reductase)/gamma *proteobacterium* HdN1]
>gi|212634008|ref|YP_002310533.1| 2-dehydropantoate 2-reductase [*Shewanella piezotolerans* WP3]
>gi|302189612|ref|ZP_07266285.1| 2-dehydropantoate 2-reductase [*Pseudomonas syringae* pv. *syringae* 642]
>gi|288931618|ref|YP_003435678.1| 2-dehydropantoate 2-reductase [*Ferroglobus placidus* DSM 10642]
>gi|127513823|ref|YP_001095020.1| 2-dehydropantoate 2-reductase [*Shewanella loihica* PV-4]
>gi|24375310|ref|NP_719353.1| 2-dehydropantoate 2-reductase [*Shewanella oneidensis* MR-1]
>gi|254515212|ref|ZP_05127273.1| 2-dehydropantoate 2-reductase [gamma *proteobacterium* NOR5-3]
>gi|237799306|ref|ZP_04587767.1| 2-dehydropantoate 2-reductase [*Pseudomonas syringae* pv. *oryzae* str. 1_6]
>gi|294101101|ref|YP_003552959.1| 2-dehydropantoate 2-reductase [*Aminobacterium colombiense* DSM 12261]
>gi|119468495|ref|ZP_01611586.1| putative 2-dehydropantoate reductase [*Alteromonadales bacterium* TW-7]
>gi|312879258|ref|ZP_07739058.1| 2-dehydropantoate 2-reductase [*Aminomonas paucivorans* DSM 12260]
>gi|28871529|ref|NP_794148.1| 2-dehydropantoate 2-reductase [*Pseudomonas syringae* pv. *tomato* str. DC3000]
>gi|298488549|ref|ZP_07006579.1| 2-dehydropantoate 2-reductase [*Pseudomonas savastanoi* pv. *savastanoi* NCPPB 3335]
>gi|114561913|ref|YP_749426.1| 2-dehydropantoate 2-reductase [*Shewanella frigidimarina* NCIMB 400]
>gi|119477336|ref|ZP_01617527.1| 2-dehydropantoate 2-reductase [marine gamma *proteobacterium* HTCC2143]
>gi|282165330|ref|YP_003357715.1| 2-dehydropantoate 2-reductase [*Methanocella paludicola* SANAE]
>gi|94502098|ref|ZP_01308601.1| 2-dehydropantoate 2-reductase [*Oceanobacter* sp. RED65]
>gi|269792076|ref|YP_003316980.1| 2-dehydropantoate 2-reductase [*Thermanaerovibrio acidaminovorans* DSM 6589]
>gi|322383702|ref|ZP_08057453.1| 2-dehydropantoate 2-reductase-like protein [*Paenibacillus larvae* subsp. *larvae* B-3650]
>gi|119775691|ref|YP_928431.1| 2-dehydropantoate 2-reductase [*Shewanella amazonensis* SB2B]
>gi|308048598|ref|YP_003912164.1| 2-dehydropantoate 2-reductase [*Ferrimonas balearica* DSM 9799]
>gi|85712652|ref|ZP_01043698.1| 2-dehydropantoate 2-reductase [*Idiomarina baltica* OS145]
>gi|229541211|ref|ZP_04430271.1| 2-dehydropantoate 2-reductase [*Bacillus coagulans* 36D1]
>gi|77361202|ref|YP_340777.1| 2-dehydropantoate reductase [*Pseudoalteromonas haloplanktis* TAC125]
>gi|11499285|ref|NP_070523.1| 2-dehydropantoate 2-reductase [*Archaeoglobus fulgidus* DSM 4304]
>gi|254427620|ref|ZP_05041327.1| 2-dehydropantoate 2-reductase [*Alcanivorax* sp. DG881]
>gi|317151157|ref|XP_001824478.2| 2-dehydropantoate 2-reductase [*Aspergillus oryzae* RIB40]
>gi|254281804|ref|ZP_04956772.1| 2-dehydropantoate 2-reductase [gamma *proteobacterium* NOR51-B]

>gi|315125903|ref|YP_004067906.1| 2-dehydropantoate reductase [*Pseudoalteromonas* sp. SM9913]
>gi|300311176|ref|YP_003775268.1| 2-dehydropantoate 2-reductase [*Herbaspirillum seropedicae* SmR1]
>gi|251797891|ref|YP_003012622.1| 2-dehydropantoate 2-reductase [*Paenibacillus* sp. JDR-2]
>gi|307544890|ref|YP_003897369.1| 2-dehydropantoate 2-reductase [*Halomonas elongata* DSM 2581]
>gi|301064244|ref|ZP_07204687.1| 2-dehydropantoate 2-reductase [delta *proteobacterium* NaphS2]
>gi|82523896|emb|CAI78619.1| ketopantoate reductase [uncultured delta *proteobacterium*]
>gi|315646013|ref|ZP_07899134.1| 2-dehydropantoate 2-reductase [*Paenibacillus vortex* V453]
>gi|229061526|ref|ZP_04198870.1| 2-dehydropantoate 2-reductase [*Bacillus cereus* AH603]
>gi|229162856|ref|ZP_04290813.1| 2-dehydropantoate 2-reductase [*Bacillus cereus* R309803]
>gi|228960138|ref|ZP_04121802.1| 2-dehydropantoate 2-reductase [*Bacillus thuringiensis* serovar *pakistani* str. T13001]
>gi|324327820|gb|ADY23080.1| 2-dehydropantoate 2-reductase [*Bacillus thuringiensis* serovar *finitimus* YBT-020]
>gi|282857022|ref|ZP_06266273.1| 2-dehydropantoate 2-reductase [*Pyramidobacter piscolens* W5455]
>gi|56460968|ref|YP_156249.1| 2-dehydropantoate 2-reductase [*Idiomarina loihiensis* L2TR]
>gi|302342758|ref|YP_003807287.1| 2-dehydropantoate 2-reductase [*Desulfarculus baarsii* DSM 2075]
>gi|260655057|ref|ZP_05860545.1| 2-dehydropantoate 2-reductase [*Jonquetella anthropi* E3_33 E1]
>gi|297180479|gb|ADI16693.1| ketopantoate reductase [uncultured gamma *proteobacterium* HF0010_05D02]
>gi|229117417|ref|ZP_04246793.1| 2-dehydropantoate 2-reductase [*Bacillus cereus* Rock1-3]
>gi|294501030|ref|YP_003564730.1| 2-dehydropantoate 2-reductase [*Bacillus megaterium* QM B1551]
>gi|310643005|ref|YP_003947763.1| 2-dehydropantoate 2-reductase [*Paenibacillus polymyxa* SC2]
>gi|121704788|ref|XP_001270657.1| 2-dehydropantoate 2-reductase, putative [*Aspergillus clavatus* NRRL 1]
>gi|194015015|ref|ZP_03053632.1| 2-dehydropantoate 2-reductase [*Bacillus pumilus* ATCC 7061]
>gi|121534373|ref|YP_001666197.1| 2-dehydropantoate 2-reductase [*Thermosinus carboxydivorans* Nor1]
>gi|300854950|ref|YP_003779934.1| ketopantoate reductase PanE/ApbA [*Clostridium ljungdahlii* DSM 13528]
>gi|228909746|ref|ZP_04073569.1| 2-dehydropantoate 2-reductase [*Bacillus thuringiensis* IBL 200]
>gi|153938200|ref|YP_001390518.1| 2-dehydropantoate 2-reductase [*Clostridium botulinum* F str. Langeland]
>gi|51243923|ref|YP_063807.1| 2-dehydropantoate 2-reductase [*Desulfotalea psychrophila* LSv54]
>gi|88858567|ref|ZP_01133209.1| putative 2-dehydropantoate reductase [*Pseudoalteromonas tunicata* D2]
>gi|241895418|ref|ZP_04782714.1| 2-dehydropantoate 2-reductase [*Weissella paramesenteroides* ATCC 33313]
>gi|229019124|ref|ZP_04175958.1| 2-dehydropantoate 2-reductase [*Bacillus cereus* AH1273]
>gi|313124944|ref|YP_004035208.1| ketopantoate reductase [*Halogeometricum borinquense* DSM 11551]
>gi|308069898|ref|YP_003871503.1| 2-dehydropantoate 2-reductase [*Paenibacillus polymyxa* E681]
>gi|134299186|ref|YP_001112682.1| 2-dehydropantoate 2-reductase [*Desulfotomaculum reducens* MI-1]
>gi|116750179|ref|YP_846866.1| 2-dehydropantoate 2-reductase [*Syntrophobacter fumaroxidans* MPOB]
>gi|242399000|ref|YP_002994424.1| 2-dehydropantoate 2-reductase [*Thermococcus sibiricus* MM 739]
>gi|190347904|gb|EDK40261.2| hypothetical proten PGUG_04359 [*Pichia guilliermondii* ATCC 6260]
>gi|301055411|ref|YP_003793622.1| putative 2-dehydropantoate 2-reductase [*Bacillus anthracis* CI]
>gi|300712827|ref|YP_03738639.1| 2-dehydropantoate 2-reductase [*Halalkalicoccus jeotgali* B3]
>gi|156052196|ref|XP_001592059.1| hypothetical protein SS1G_07507 [*Sclerotinia sclerotiorum* 1980]
>gi|85704948|ref|ZP_01036049.1| ketopantoate reductase ApbA [*Roseovarius* sp. 217]
>gi|295399703|ref|ZP_06809684.1| 2-dehydropantoate 2-reductase [*Geobacillus thermoglucosidasius* C56-YS93]
>gi|254573604|ref|XP_002493911.1| hypothetical protein [*Pichia pastoris* GS115]
>gi|299132097|ref|ZP_07025292.1| 2-dehydropantoate 2-reductase [*Afipia* sp. 1NLS2]
>gi|307354061|ref|YP_003895112.1| 2-dehydropantoate 2-reductase [*Methanoplanus petrolearius* DSM 11571]
>gi|261405647|ref|YP_003241888.1| 2-dehydropantoate 2-reductase [*Paenibacillus* sp. Y412MC10]
>gi|289581665|ref|YP_003480131.1| 2-dehydropantoate 2-reductase [*Natrialba magadii* ATCC 43099]
>gi|212696972|ref|ZP_03305100.1| hypothetical protein ANHYDRO_01535 [*Anaerococcus hydrogenalis* DSM 7454]
>gi|70730838|ref|YP_260579.1| 2-dehydropantoate 2-reductase [*Pseudomonas fluorescens* Pf-5]
>gi|225575149|ref|ZP_03783759.1| hypothetical protein RUMHYD_03238 [*Blautia hydrogenotrophica* DSM 10507]
>gi|296504414|ref|YP_003666114.1| 2-dehydropantoate 2-reductase [*Bacillus thuringiensis* BMB171]
>gi|187780219|ref|ZP_02996692.1| hypothetical protein CLOSPO_03815 [*Clostridium sporogenes* ATCC 15579]
>gi|56475560|ref|YP_157149.1| ketopantoate reductase ApbA [*Aromatoleum aromaticum* EbN1]
>gi|57641903|ref|YP_184361.1| 2-dehydropantoate 2-reductase [*Thermococcus kodakarensis* KOD1]
>gi|296242388|ref|YP_003649875.1| 2-dehydropantoate 2-reductase [*Thermosphaera aggregans* DSM 11486]
>gi|229031552|ref|ZP_04187552.1| 2-dehydropantoate 2-reductase [*Bacillus cereus* AH1271]
>gi|152996054|ref|YP_001340889.1| 2-dehydropantoate 2-reductase [*Marinomonas* sp. MWYL1]
>gi|88704128|ref|ZP_01101843.1| Ketopantoate reductase ApbA/PanE [*Congregibacter litoralis* KT71]
>gi|149181743|ref|ZP_01860235.1| 2-dehydropantoate 2-reductase [*Bacillus* sp. SG-1]
>gi|322371463|ref|ZP_08046012.1| 2-dehydropantoate 2-reductase [*Haladaptatus paucihalophilus* DX253]
>gi|110833490|ref|YP_692349.1| 2-dehydropantoate 2-reductase [*Alcanivorax borkumensis* SK2]
>gi|241663589|ref|YP_002981949.1| 2-dehydropantoate 2-reductase [*Ralstonia pickettii* 12D]
>gi|18977768|ref|NP_579125.1| 2-dehydropantoate 2-reductase [*Pyrococcus furiosus* DSM 3638]
>gi|110798963|ref|YP_695239.1| 2-dehydropantoate 2-reductase [*Clostridium perfringens* ATCC 13124]
>gi|169782143|ref|XP_001825534.1| 2-dehydropantoate 2-reductase family protein [*Aspergillus oryzae* RIB40]
>gi|157692185|ref|YP_001486647.1| 2-dehydropantoate 2-reductase [*Bacillus pumilus* SAFR-032]
>gi|15606805|ref|NP_214186.1| hypothetical protein aq_1727 [*Aquifex aeolicus* VF5]

>gi|163782247|ref|ZP_02177245.1| hypothetical protein HG1285_05655 [*Hydrogenivirga* sp. 126-5-R1-1]
>gi|317129310|ref|YP_004095592.1| 2-dehydropantoate 2 reductase [*Bacillus cellulosilyticus* DSM 2522]
>gi|229174587|ref|ZP_04302117.1| 2-dehydropantoate 2-reductase [*Bacillus cereus* MM3]
>gi|229086485|ref|ZP_04218657.1| 2-dehydropantoate 2-reductase [*Bacillus cereus* Rock3-44]
>gi|167044940|gb|ABZ09606.1| putative Ketopantoate reductase PanE/ApbA [uncultured marine microorganism HF4000_APKG8D23]
>gi|15896190|ref|NP_349539.1| ketopantoate reductase PanE/ApbA [*Clostridium acetobutylicum* ATCC 824]
>gi|324103300|gb|EGC00636.1| 2-dehydropantoate 2-reductase [*Pseudomonas* sp. TJI-51]
>gi|14520967|ref|NP_126442.1| 2-dehydropantoate 2-reductase [*Pyrococcus abyssi GE*51]
>gi|222097366|ref|YP_002531423.1| 2-dehydropantoate 2-reductase [*Bacillus cereus Q*1]
>gi|319649677|ref|ZP_08003833.1| 2-dehydropantoate 2-reductase [*Bacillus* sp. 2_A_57_CT2]
>gi|258514829|ref|YP_003191051.1| 2-dehydropantoate 2-reductase [*Desulfotomaculum acetoxidans* DSM 771]
>gi|87121684|ref|ZP_01077770.1| ketopantoate reductase [*Marinomonas* sp. MED121]
>gi|145589722|ref|YP_01156319.1| 2-dehydropantoate 2-reductase [*Polynucleobacter necessarius* subsp. *asymbioticus* QLW-P1DMWA-1]
>gi|254173247|ref|ZP_04879920.1| 2-dehydropantoate 2-reductase [*Thermococcus* sp. AM4]
>gi|145592200|ref|YP_001154202.1| 2-dehydropantoate 2-reductase [*Pyrobaculum arsenaticum* DSM 13514]
>gi|91788789|ref|YP_549741.1| 2-dehydropantoate 2-reductase [*Polaromonas* sp. JS666]
>gi|257387161|ref|YP_003176934.1| 2-dehydropantoate 2-reductase [*Halomicrobium mukohataei* DSM 12286]
>gi|18314044|ref|NP_560711.1| 2-dehydropantoate 2-reductase (ketopantoate reductase) [*Pyrobaculum aerophilum* str. IM2]
>gi|319646112|ref|ZP_08000342.1| YlbQ protein [*Bacillus* sp. BT1B_CT2]
>gi|168232151|ref|ZP_02657209.1| 2-dehydropantoate 2-reductase [*Salmonella enterica* subsp. *enterica* serovar Kentucky str. CDC 191]
>gi|323488622|ref|ZP_08093866.1| 2-dehydropantoate 2-reductase [*Planococcus donghaensis* MPA1U2]
>gi|226313441|ref|YP_002773335.1| 2-dehydropantoate 2-reductase [*Brevibacillus brevis* NBRC 100599]
>gi|88799068|ref|ZP_01114649.1| 2-dehydropantoate 2-reductase [*Reinekea* sp. MED297]
>gi|242813341|ref|XP_002486147.1| 2-dehydropantoate 2-reductase, putative [*Talaromyces stipitatus* ATCC 10500]
>gi|225849819|ref|YP_002730053.1| 2-dehydropantoate 2-reductase [*Persephonella marina* EX-H1]
>gi|209664195|ref|YP_002288052.1| 2-dehydropantoate 2-reductase [*Oligotropha carboxidovorans* OM5]
>gi|188589152|ref|YP_001920485.1| 2-dehydropantoate 2-reductase [*Clostridium botulinum* E3 str. Alaska E43]
>gi|119505092|ref|ZP_01627168.1| 2-dehydropantoate 2-reductase [marine gamma *proteobacterium* HTCC2080]
>gi|15789904|ref|NP_279728.1| hypothetical protein VNG0730C [*Halobacterium* sp. NRC-1]
>gi|300709487|ref|YP_003735301.1| 2-dehydropantoate 2-reductase [*Halalkalicoccus jeotgali* B3]
>gi|269124038|ref|YP_003306615.1| 2-dehydropantoate 2-reductase [*Streptobacillus moniliformis* DSM 12112]
>gi|212224616|ref|YP_002307852.1| 2-dehydropantoate 2-reductase [*Thermococcus onnurineus* NA1]
>gi|302335576|ref|YP_003800783.1| 2-dehydropantoate 2-reductase [*Olsenella uli* DSM 7084]
>gi|154150658|ref|YP_001404276.1| 2-dehydropantoate 2-reductase [*Candidates Methanoregula boonei* 6A8]
>gi|284166943|ref|YP_003405222.1| 2-dehydropantoate 2-reductase [*Haloterrigena turkmenica* DSM 5511]
>gi|172057979|ref|YP_001814439.1| 2-dehydropantoate 2-reductase [*Exiguobacterium sibiricum* 255-15]
>gi|313637013|gb|EFS02587.1| 2-dehydropantoate 2-reductase [*Listeria seeligeri* FSL S4-171]
>gi|228998702|ref|ZP_04158289.1| 2-dehydropantoate 2-reductase [*Bacillus mycoides* Rock3-17]
>gi|152976282|ref|YP_001375799.1| 2-dehydropantoate 2-reductase [*Bacillus cereus* subsp. *cytotoxis* NVH 391-98]
>gi|92114269|ref|YP_574197.1| 2-dehydropantoate 2-reductase [*Chromohalobacter salexigens* DSM 3043]
>gi|240102379|ref|YP_002958688.1| 2-dehydropantoate 2-reductase [*Thermococcus gammatolerans* EJ3]
>gi|206889443|ref|YP_002249396.1| 2-dehydropantoate 2-reductase [*Thermodesulfovibrio yellowstonii* DSM 11347]
>gi|297583937|ref|YP_003699717.1| 2-dehydropantoate 2-reductase [*Bacillus selenitireducens* MLS10]
>gi|270290296|ref|ZP_06196521.1| 2-dehydropantoate 2-reductase [*Pediococcus acidilactici* 7_4]
>gi|147919508|ref|YP_686752.1| putative 2-dehydropantoate 2-reductase [uncultured methanogenic archaeon RC-1]
>gi|313632475|gb|EFR99493.1| 2-dehydropantoate 2-reductase [*Listeria seeligeri* FSL N1-067]
>gi|266623089|ref|ZP_06116024.1| 2-dehydropantoate 2-reductase [*Clostridium hathewayi* DSM 13479]
>gi|186470939|ref|YP_001862257.1| 2-dehydropantoate 2-reductase [*Burkholderia phymatum* STM815]
>gi|91975083|ref|YP_567742.1| 2-dehydropantoate 2-reductase [*Rhodopseudomonas palustris* BisB5]
>gi|168186958|ref|ZP_02621593.1| 2-dehydropantoate 2-reductase [*Clostridium botulinum* C str. Eklund]
>gi|171316249|ref|ZP_02905471.1| 2-dehydropantoate 2-reductase [*Burkholderia ambifaria* MEX-5]
>gi|118444120|ref|YP_877052.1| 2-dehydropantoate 2-reductase [*Clostridium novyi* NT]
>gi|304403996|ref|ZP_07385658.1| 2-dehydropantoate 2-reductase [*Paenibacillus curdlanolyticus* YK9]
>gi|14591192|ref|NP_143268.1| 2-dehydropantoate 2-reductase [*Pyrococcus horikoshii* OT3]
>gi|39937620|ref|NP_949896.1| putative 2-dehydropantoate 2-reductase [*Rhodopseudomonas palustris* CGA009]
>gi|257051985|ref|YP_003129818.1| 2-dehydropantoate 2-reductase [*Halorhabdus utahensis* DSM 12940]
>gi|297616632|ref|YP_003701791.1| 2-dehydropantoate 2-reductase [*Syntrophothermus lipocalidus* DSM 12680]
>gi|124485202|ref|YP_001029818.1| hypothetical protein Mlab_0375 [*Methanocorpusculum labreanum* Z]
>gi|311029915|ref|ZP_07708005.1| 2-dehydropantoate 2-reductase [*Bacillus* sp. m3-13]
>gi|320355422|ref|YP_004196761.1| 2-dehydropantoate 2-reductase [*Desulfobulbus propionicus* DSM 2032]
>gi|255654270|ref|ZP_05399679.1| putative ketopantoate reductase [*Clostridium difficile* QCD-23m63]
>gi|86747344|ref|YP_483840.1| 2-dehydropantoate 2-reductase [*Rhodopseudomonas palustris* HaA2]
>gi|319796261|ref|YP_004157901.1| 2-dehydropantoate 2-reductase [*Variovorax paradoxus* EPS]

>gi|289435387|ref|YP_003465259.1| 2-dehydropantoate 2-reductase [*Listeria seeligeri* serovar 1/2b str. SLCC3954]
>gi|284161230|ref|YP_003399853.1| 2-dehydropantoate 2-reductase [*Archaeoglobus profundus* DSM 5631]
>gi|163792409|ref|ZP_02186386.1| 2-dehydropantoate 2-reductase [alpha *proteobacterium* BAL199]
>gi|227535072|ref|ZP_03965121.1| 2-dehydropantoate 2-reductase [*Lactobacillus paracasei* subsp. *paracasei* ATCC 25302]
>gi|172065517|ref|YP_001816229.1| 2-dehydropantoate 2-reductase [*Burkholderia ambifaria* MC40-6]
>gi|56696485|ref|YP_166842.1| 2-dehydropantoate 2-reductase [*Ruegeria pomeroyi* DSS-3]
>gi|212639667|ref|YP_002316187.1| 2-dehydropantoate 2-reductase [*Anoxybacillus flavithermus* WK1]
>gi|73538792|ref|YP_299159.1| ketopantoate reductase ApbA/PanE [*Ralstonia eutropha* JMP134]
>gi|288818570|ref|YP_003432918.1| 2-dehydropantoate 2-reductase [*Hydrogenobacter thermophilus* TK-6]
>gi|160941380|ref|ZP_02088717.1| hypothetical protein CLOBOL_06273 [*Clostridium bolteae* ATCC BAA-613]
>gi|167630796|ref|YP_001681295.1| 2-dehydropantoate 2-reductase [*Heliobacterium modesticaldum* Ice1]
>gi|89099594|ref|ZP_01172469.1| 2-dehydropantoate 2-reductase [*Bacillus* sp. NRRL B-14911]
>gi|227431961|ref|ZP_03913981.1| possible 2-dehydropantoate 2-reductase [*Leuconostoc mesenteroides* subsp. *cremoris* ATCC 19254]
>gi|299534661|ref|ZP_07047993.1| putative 2-dehydropantoate 2-reductase [*Lysinibacillus fusiformis* ZC1]
>gi|227552200|ref|ZP_03982249.1| 2-dehydropantoate 2-reductase [*Enterococcus faecium* TX1330]
>gi|289595871|ref|YP_003482567.1| 2-dehydropantoate 2-reductase [*Aciduliprofundum boonei* T469]
>gi|138894643|ref|YP_001125096.1| 2-dehydropantoate 2-reductase [*Geobacillus thermodenitrificans* NG80-2]
>gi|55379641|ref|YP_137491.1| 2-dehydropantoate 2-reductase [*Haloarcula marismortui* ATCC 43049]
>gi|294083831|ref|YP_003550588.1| 2-dehydropantoate 2-reductase [*Candidatus Puniceispirillum marinum* IMCC1322]
>gi|119898762|ref|YP_933975.1| 2-dehydropantoate 2-reductase [*Azoarcus* sp. BH72]
>gi|119872861|ref|YP_930868.1| 2-dehydropantoate 2-reductase [*Pyrobaculum islandicum* DSM 4184]
>gi|257456159|ref|ZP_05621356.1| 2-dehydropantoate 2-reductase [*Treponema vincentii* ATCC 35580]
>gi|257867166|ref|ZP_05646819.1| ketopantoate reductase [*Enterococcus casseliflavus* EC30]
>gi|126459006|ref|YP_001055284.1| 2-dehydropantoate 2-reductase [*Pyrobaculum calidifontis* JCM 11548]
>gi|239826511|ref|YP_002949135.1| 2-dehydropantoate 2-reductase [*Geobacillus* sp. WCH70]
>gi|91790339|ref|YP_551291.1| 2-dehydropantoate 2-reductase [*Polaromonas* sp. JS666]
>gi|256829670|ref|YP_003158398.1| 2-dehydropantoate 2-reductase [*Desulfomicrobium baculatum* DSM 4028]
>gi|315659442|ref|ZP_07912305.1| 2-dehydropantoate 2-reductase [*Staphylococcus lugdunensis* M23590]
>gi|150403611|ref|YP_001330905.1| 2-dehydropantoate 2-reductase [*Methanococcus maripaludis* C7]
>gi|259047992|ref|ZP_05738393.1| 2-dehydropantoate 2-reductase [*Granulicatella adiacens* ATCC 49175]
>gi|24214890|ref|NP_712371.1| 2-dehydropantoate 2-reductase [*Leptospira interrogans* serovar Lai str. 56601]
>gi|319789510|ref|YP_004151143.1| 2-dehydropantoate 2-reductase [*Thermovibrio ammonificans* HB-1]
>gi|171320779|ref|ZP_02909787.1| 2-dehydropantoate 2-reductase [*Burkholderia ambifaria* MEX-5]
>gi|295705715|ref|YP_003598790.1| 2-dehydropantoate 2-reductase [*Bacillus megaterium* DSM 319]
>gi|256853805|ref|ZP_05559170.1| 2-dehydropantoate 2-reductase [*Enterococcus faecalis* T8]
>gi|186472751|ref|YP_001860093.1| 2-dehydropantoate 2-reductase [*Burkholderia phymatum* STM815]
>gi|164687814|ref|ZP_02211842.1| hypothetical protein CLOBAR_01458 [*Clostridium bartlettii* DSM 16795]
>gi|315147351|gb|EFT91367.1| 2-dehydropantoate 2-reductase [*Enterococcus faecalis* TX4244]
>gi|289450069|ref|YP_003474740.1| putative 2-dehydropantoate 2-reductase [*Clostridiales* genomosp. BVAB3 str. UPII9-5]
>gi|126178741|ref|YP_001046706.1| 2-dehydropantoate 2-reductase [*Methanoculleus marisnigri* JR1]
>gi|313622979|gb|EFR93276.1| 2-dehydropantoate 2-reductase [*Listeria innocua* FSL J1-023]
>gi|197117182|ref|YP_002137609.1| 2-dehydropantoate 2-reductase [*Geobacter bemidjiensis* Bem]
>gi|257065623|ref|YP_003151879.1| 2-dehydropantoate 2-reductase [*Anaerococcus prevotii* DSM 20548]
>gi|221211405|ref|ZP_03584384.1| 2-dehydropantoate 2-reductase [*Burkholderia multivorans* CGD1]
>gi|121606900|ref|YP_984229.1| 2-dehydropantoate 2-reductase [*Polaromonas naphthalenivorans* CJ2]
>gi|229823430|ref|ZP_04449499.1| hypothetical protein GCWU000282_00728 [*Catonella morbi* ATCC 51271]
>gi|303256960|ref|ZP_07342974.1| 2-dehydropantoate 2-reductase [*Burkholderiales bacterium* 1_1_47]
>gi|159042347|ref|YP_001541599.1| 2-dehydropantoate 2-reductase [*Caldivirga maquilingensis* IC-167]
>gi|315155665|gb|EFT99681.1| 2-dehydropantoate 2-reductase [*Enterococcus faecalis* TX0043]
>gi|317496587|ref|ZP_07954935.1| 2-dehydropantoate 2-reductase [*Gemella moribillum* M424]
>gi|323342656|ref|ZP_08082888.1| 2-dehydropantoate 2-reductase [*Erysipelothrix rhusiopathiae* ATCC 19414]
>gi|239817916|ref|YP_002946826.1| 2-dehydropantoate 2-reductase [*Variovorax paradoxus* S110]
>gi|254169372|ref|ZP_04876201.1| 2-dehydropantoate 2-reductase [*Aciduliprofundum boonei* T469]
>gi|307594721|ref|YP_003901038.1| 2-dehydropantoate 2-reductase [*Vulcanisaeta distributa* DSM 14429]
>gi|297530725|ref|YP_003672000.1| 2-dehydropantoate 2-reductase [*Geobacillus* sp. C56-T3]
>gi|300173017|ref|YP_003772183.1| 2-dehydropantoate 2-reductase [*Leuconostoc gasicomitatum* LMG 18811]
>gi|52549536|gb|AAU83385.1| hypothetical protein GZ27G5_16 [uncultured *archaeon* GZfos27G5]
>gi|119094200|gb|ABL61022.1| ketopantoate reductase [uncultured marine *bacterium* HF10_25F10]
>gi|162146807|ref|YP_001601268.1| putative 2-dehydropantoate 2-reductase [*Gluconacetobacter diazotrophicus* PAI 5]
>gi|256963612|ref|ZP_05567763.1| ketopantoate reductase ApbA/PanE [*Enterococcus faecalis* HIP11704]
>gi|313617966|gb|EFR90131.1| 2-dehydropantoate 2-reductase [*Listeria innocua* FSL S4-378]
>gi|313679570|ref|YP_004057309.1| 2-dehydropantoate 2-reductase [*Oceanithermus profundus* DSM 14977]
>gi|313885617|ref|ZP_07819367.1| 2-dehydropantoate 2-reductase[*(Eremococcus coleocola* ACS-139-V-Col8]

>gi|163790016|ref|ZP_02184451.1| 2-dehydropantoate 2-reductase [*Carnobacterium* sp. AT7]
>gi|225870636|ref|YP_002746583.1| ketopantoate reductase [*Streptococcus equi* subsp. *equi* 4047]
>gi|320527125|ref|ZP_08028312.1| 2-dehydropantoate 2-reductase [*Solobacterium moorei* F0204]
>gi|316936042|ref|YP_004111024.1| 2-dehydropantoate 2 reductase [*Rhodopseudomonas palustris* DX-1]
>gi|209559212|ref|YP_002285684.1| 2-dehydropantoate 2-reductase [*Streptococcus pyogenes* NZ131]
>gi|315304102|ref|ZP_07874502.1| 2-dehydropantoate 2-reductase [*Listeria ivanovii* FSL F6-596]
>gi|323373091|gb|ADX45360.1| 2-dehydropantoate 2-reductase [*Acidovorax avenae* subsp. *avenae* ATCC 19860]
>gi|169782199|ref|XP_001825562.1| 2-dehydropantoate 2-reductase family protein [*Aspergillus oryzae* RIB40]
>gi|188996324|ref|YP_001930575.1| 2-dehydropantoate 2-reductase [*Sulfurihydrogenibrum* sp. YO3AOP1]
>gi|206561131|ref|YP_02231896.1| putative ketopantoate reductase [*Burkholderia cenocepacia* J2315]
>gi|56807918|ref|ZP_00365743.1| COG1893: Ketopantoate reductase [*Streptococcus pyogenes* M49 591]
>gi|120610087|ref|YP_969765.1| 2-dehydropantoate 2-reductase [*Acidovorax avenae* subsp. *citrulli* AAC00-1]
>gi|52548816|gb|AAU82665.1| conserved hypothetical protein [uncultured *archaeon* GZfos19A5]
>gi|70725616|ref|YP_252530.1| 2-dehydropantoate 2-reductase [*Staphylococcus haemolyticus* JCSC1435]
>gi|292654245|ref|YP_003534142.1| 2-dehydropantoate 2-reductase [*Haloferax volcanii* DS2]
>gi|288931405|ref|YP_003435465.1| 2-dehydropantoate 2-reductase [*Ferroglobus placidus* DSM 10642]
>gi|150400258|ref|YP_001324025.1| 2-dehydropantoate 2-reductase [*Methanococcus vannielii* SB]
>gi|126466272|ref|YP_001041381.1| 2-dehydropantoate 2-reductase [*Staphylothermus marinus* F1]
>gi|221068483|ref|ZP_03544588.1| 2-dehydropantoate 2-reductase [*Comamonas testosteroni* KF-1]
>gi|299821547|ref|ZP_07053435.1| possible 2-dehydropantoate 2-reductase [*Listeri grayi* DSM 20601]
>gi|290508302|ref|ZP_06547673.1| 2-dehydropantoate 2-reductase [*Klebsiella* sp. 1_1_55]
>gi|297570429|ref|YP_003691773.1| 2-dehydropantoate 2-reductase [*Desulfurivibrio alkaliphilus* AHT2]
>gi|169827000|ref|YP_001697158.1| putative 2-dehydropantoate 2-reductase [*Lysinibacillus sphaericus* C3-41]
>gi|238503586|ref|XP_002383026.1| 2-dehydropantoate 2-reductase family protein, putative [*Aspergillus flavus* NRRL3357]
>gi|116873476|ref|YP_850257.1| 2-dehydropantoate 2-reductase [*Listeria welshimeri* serovar 6b str. SLCC5334]
>gi|242556790|pdb|3HWR|A Chain A, Crystal Structure Of PaneAPBA family ketopantoate reductase (Yp_299159.1) From Ralstonia Eutropha Jmp134
>gi|302387383|ref|YP_003823205.1| 2-dehydropantoate 2-reductase [*Clostridium saccharolyticum* WM1]
>gi|307726219|ref|YP_003909432.1| 2-dehydropantoate 2-reductase [*Burkholderia* sp. CCGE1003]
>gi|257871049|ref|ZP_05650702.1|ketopantoate reductase [*Enterococcus gallinarum* EG2]
>gi|145254262|ref|XP_001398576.1| 2-dehydropantoate 2-reductase family protein [*Aspergillus niger* CBS 513.88]
>gi|227515951|ref|ZP_03946000.1| 2-dehydropantoate 2-reductase [*Atopobium vaginae* DSM 15829]
>gi|254247377|ref|ZP_04940698.1|Ketopantoate reductase [*Burkholderia cenocepacia* PC184]
>gi|297527045|ref|YP_003669069.1| 2-dehydropantoate 2-reductase [*Staphylothermus hellenicus* DSM 12710]
>gi|303233096|ref|ZP_07319769.1| 2-dehydropantoate 2-reductase [*Atopobium vaginae* PB189-T1-4]
>gi|253699477|ref|YP_003020666.1| 2-dehydropantoate 2-reductase [*Geobacter* sp. M21]
>gi|293401734|ref|ZP_06645875.1| 2-dehydropantoate 2-reductase [*Erysipelotrichaceae bacterium* 5_2_54FAA]
>gi|225849463|ref|YP_002729628.1| 2-dehydropantoate 2-reductase [*Sulfurihydrogenibium azorense* Az-Fu1]
>gi|227893553|ref|ZP_04011358.1| 2-dehydropantoate 2-reductase [*Lactobacillus ultunensis* DSM 16047]
>gi|85544557|pdb|2EW2|A Chain A, Crystal Structure Of The Putative 2-Dehydropantoate 2- Reductase From *Enterococcus Faecalis*
>gi|146318978|ref|YP_001198690.1| 2-dehydropantoate 2-reductase [*Streptococcus suis* 05ZYH33]
>gi|124266554|ref|YP_001020558.1| 2-dehydropantoate 2-reductase [*Methylibium petroleiphilum* PM1]
>gi|283768342|ref|ZP_06341254.1| 2-dehydropantoate 2-reductase [*Bulleidia extructa* W1219]
>gi|315223029|ref|ZP_07864908.1| 2-dehydropantoate 2-reductase [*Streptococcus anginosus* F0211]
>gi|207857980|ref|YP_002244631.1| 2-dehydropantoate 2-reductase [*Salmonella enterica* subsp. *enterica* serovar Enteritidis str. P125109]
>gi|134293442|ref|YP_001117178.1| 2-dehydropantoate 2-reductase [*Burkholderia vietnamiensis* G4]
>gi|52550479|gb|AAU84328.1| conserved hypothetical protein [uncultured *archaeon* GZfos9D1]
>gi|324965153|gb|ADY55932.1| 2-dehydropantoate 2-reductase [*Syntrophobotulus glycolicus* DSM 8271]
>gi|296331086|ref|ZP_06873560.1| 2-dehydropantoate 2-reductase [*Bacillus subtilis* subsp. *spizizenii* ATCC 6633]
>gi|228474704|ref|ZP_04059435.1| 2-dehydropantoate 2-reductase [*Staphylococcus hominis* SK119]
>gi|119896483|ref|YP_931696.1| 2-dehydropantoate 2-reductase [*Azoarcus* sp. BH72]
>gi|297181166|gb|ADI17362.1| ketopantoate reductase [uncultured delta *proteobacterium* HF0070_30B07]
>gi|169333685|ref|ZP_02860878.1| hypothetical protein ANASTE_00069 [*Anaerofustis stercorihominis* DSM 17244]
>gi|171184791|ref|YP_001793710.1| 2-dehydropantoate 2-reductase [*Thermoproteus neutrophilus* V24Sta]
>gi|116334695|ref|YP_796222.1| 2-dehydropantoate 2-reductase [*Lactobacillus brevis* ATCC 367]
>gi|45358235|ref|NP_987792.1| binding-protein dependent transport system inner membrane protein [*Methanococcus maripaludis* S2]
>gi|15673305|ref|NP_267479.1| 2-dehydropantoate 2-reductase [*Lactococcus lactis* subsp. *lactis* Il1403]
>gi|167569002|ref|ZP_02361876.1| 2-dehydropantoate 2-reductase [*Burkholderia oklahomensis* C6786]
>gi|222444726|ref|ZP_03607241.1| hypothetical protein METSMIALI_00339 [*Methanobrevibacter smithii* DSM 2375]
>gi|148642093|ref|YP_001272606.1| ketopantoate reductase. ApbA [*Methanobrevibacter smithii* ATCC 35061]
>gi|56964133|ref|YP_175864.1| 2-dehydropantoate 2-reductase [*Bacillus clausii* KSM-K16]
>gi|76801123|ref|YP_326131.1| 2-dehydropantoate 2-reductase [*Natronomonas pharaonis* DSM 2160]
>gi|291563922|emb|CBL42738.1| ketopantoate reductase [butyrate-producing *bacterium* SS3/4]

>gi|126649737|ref|ZP_01721973.1| 2-dehydropantoate 2-reductase [*Bacillus* sp. B14905]
>gi|125623962|ref|YP_001032445.1| 2-dehydropantoate 2-reductase [*Lactococcus lactis* subsp. *cremoris* MG1363]
>gi|264677329|ref|YP_003277235.1| 2-dehydropantoate 2-reductase [*Comamonas testosteroni* CNB-2]
>gi|163793943|ref|ZP_02187917.1| putative ketopantoate reductase [alpha *proteobacterium* BAL199]
>gi|229543594|ref|ZP_04432654 1| 2-dehydropantoate 2-reductase [*Bacillus coagulans* 36D1]
>gi|208435758|pdb|3EGO|A Chain A, Crystal Structure Of Probable 2-Dehydropantoate 2-Reductase Pane From *Bacillus Subtillis*
>gi|86143831|ref|ZP_01062207.1| hypothetical protein MED217_01020 [*Leeuwenhoekiella blandensis* MED217]
>gi|260946531|ref|XP_002617563.1| hypothetical protein CLUG_03007 [*Clavispora lusitaniae* ATCC 42720]
>gi|15615142|ref|NP_243445.1| 2-dehydropantoate 2-reductase [*Bacillus halodurans* C-125]
>gi|239625263|ref|ZP_04668294.1| 2-dehydropantoate 2-reductase [*Clostridiales bacterium* 1_7_47_FAA]
>gi|315038258|ref|YP_004031826.1| 2-dehydropantoate 2-reductase [*Lactobacillus amylovorus* GRL 1112]
>gi|300310480|ref|YP_003774572.1| 2-dehydropantoate 2-reductase [*Herbaspirillum seropedicae* SmR1]
>gi|167893095|ref|ZP_02480497.1| 2-dehydropantoate 2-reductase [*Burkholderia pseudomallei* 7894]
>gi|89894746|ref|YP_518233.1| hypothetical protein DSY2000 [*Desulfitobacterium hafniense* Y51]
>gi|319762040|ref|YP_004125977.1| 2-dehydropantoate 2-reductase [*Alicycliphilus denitrificans* BC]
>gi|69250617|ref|ZP_00605173.1| Ketopantoate reductase ApbA/PanE [*Enterococcus faecium* DO]
>gi|288560576|ref|YP_003424062.1| 2-dehydropantoate 2-reductase PanE [*Methanobrevibacter ruminantium* M1]
>gi|70725181|ref|YP_252095.1| 2-dehydropantoate 2-reductase [*Staphylococcus haemolyticus* JCSC1435]
>gi|324098987|gb|EGB96980.1| 2-dehydropantoate 2-reductase [*Pseudomonas* sp. TJI-51]
>gi|86608338|ref|YP_477100.1| 2-dehydropantoate 2-reductase [*Synechococcus* sp. JA-2-3B'a(2-13)]
>gi|67906799|gb|AAY82862.1| putative ketopantoate reductase [uncultured *bacterium* MedeBAC46A06]
>gi|310778974|ref|YP_003967307.1| ketopantoate reductase [*Ilyobacter polytropus* DSM 2926]
>gi|242372095|ref|ZP_04817669.1| 2-dehydropantoate 2-reductase [*Staphylococcus epidermidis* M23864:W1]
>gi|170749968|ref|YP_001756228.1| 2-dehydropantoate 2-reductase [*Methylobacterium radiotolerans* JCM 2831]
>gi|167588290|ref|ZP_02380678.1| 2-dehydropantoate 2-reductase [*Burkholderia ubonensis* Bu]
>gi|78067381|ref|YP_370150.1| 2-dehydropantoate 2-reductase[*Burkholderia* sp. 383]
>gi|124028371|ref|YP_001013691.1| ketopantoate reductase [*Hyperthermus butylicus* DSM 5456]
>gi|219848017|ref|YP_002462450.1| 2-dehydropantoate 2-reductase [*Chloroflexus aggregans* DSM 9485]
>gi|167580031|ref|ZP_02372905.1| 2-dehydropantoate 2-reductase [*Burkholderia thailandensis* TXDOH]
>gi|288553174|ref|YP_003425109.1| 2-dehydropantoate 2-reductase [*Bacillus pseudofirmus* OF4]
>gi|186470810|ref|YP_001862128.1| 2-dehydropantoate 2-reductase [*Burkholderia phymatum* STM815]
>gi|313890559|ref|ZP_07824187.1| 2-dehydropantoate 2-reductase [*Streptococcus pseudoporcinus* SPIN 20026]
>gi|310827874|ref|YP_003960231.1| hypothetical protein ELI_2285 [*Eubacterium limosum* KIST612]
>gi|121595444|ref|YP_987340.1| 2-dehydropantoate 2-reductase [*Acidovorax* sp. JS42]
>gi|29375143|ref|NP_814296.1| 2-dehydropantoate 2-reductase [*Enterococcus faecalis* V583]
>gi|313899882|ref|ZP_07833385.1| 2-dehydropantoate 2-reductase [*Clostridium* sp. HGF2]
>gi|187920203|ref|YP_001889234.1| 2-dehydropantoate 2-reductase [*Burkholderia phytofirmans* PsJN]
>gi|27381507|ref|NP_773036.1| 2-dehydropantoate 2-reductase [*Bradyrhizobium japonicum* USDA 110]
>gi|300768503|ref|ZP_07078402.1| 2-dehydropantoate 2-reductase [*Lactobacillus plantarum* subsp. *plantarum* ATCC 14917]
>gi|197295211|ref|YP_002153752.1| putative 2-dehydropantoate 2-reductase [*Burkholderia cenocepacia* J2315]
>gi|225410102|ref|ZP_03761291.1| hypothetical protein CLOSTASPAR_05323 [*Clostridium asparagiforme* DSM 15981]
>gi|222152909|ref|YP_02562086.1| 2-dehydropantoate 2-reductase [*Streptococcus uberis* 0140J]
>gi|300854058|ref|YP_003779042.1| 2-dehydropantoate 2-reductase [*Clostridium ljungdahlii* DSM 13528]
>gi|237653536|ref|YP_002889650.1| 2-dehydropantoate 2-reductase [*Thauera* sp. MZ1T]
>gi|259047521|ref|ZP_05737922.1| 2-dehydropantoate 2-reductase [*Granulicatella adiacens* ATCC 49175]
>gi|319957266|ref|YP_004168529.1| 2-dehydropantoate 2-reductase [*Nitratifractor salsuginis* DSM 16511]
>gi|320355269|ref|YP_004196608.1| 2-dehydropantoate 2-reductase [*Desulfobulbus propionicus* DSM 2032]
>gi|239636063|ref|ZP_04677077.1| 2-dehydropantoate 2-reductase [*Staphylococcus warneri* L37603]
>gi|320100944|ref|YP_004176536.1| ketopantoate reductase [*Desulfurococcus mucosus* DSM 2162]
>gi|169630635|ref|YP_001704284.1| ketopantoate reductase ApbA/PanE [*Mycobacterium abscessus* ATCC 19977]
>gi|81427656|ref|YP_394653.1| 2-dehydropantoate 2-reductase [*Lactobacillus sakei* subsp. *sakei* 23K]
>gi|241889407|ref|ZP_04776708.1| 2-dehydropantoate 2-reductase [*Gemella haemolysans* ATCC 10379]
>gi|251811868|ref|ZP_04826341.1| 2-dehydropantoate 2-reductase [*Staphylococcus epidermidis* BCM-HMP0060]
>gi|218883653|ref|YP_002428035.1| 2-dehydropantoate 2-reductase [*Desulfurococcus kamchatkensis* 1221n]
>gi|229918541|ref|YP_002887187.1| 2-dehydropantoate 2-reductase [*Exiguobacterium* sp. AT1b]
>gi|314939006|ref|ZP_07846271.1| 2-dehydropantoate 2-reductase [*Enterococcus faecium* TX0133a04]
>gi|69244336|ref|ZP_00602804.1| Ketopantoate reductase ApbA/PanE [*Enterococcus faecium* DO]
>gi|311068031|ref|YP_003972954.1| 2-dehydropantoate2-reductase [*Bacillus atrophaeus* 1942]
>gi|219847221|ref|YP_002461654.1| 2-dehydropantoate 2-reductase [*Chloroflexus aggregans* DSM 9485]
>gi|295699875|ref|YP_003607768.1| 2-dehydropantoate 2-reductase [*Burkholderia* sp. CCGE1002]
>gi|307730136|ref|YP_003907360.1| 2-dehydropantoate 2-reductase [*Burkholderia sp.* CCGE1003]
>gi|261350733|ref|YP_05976150.1| 2-dehydropantoate 2-reductase [*Methanobrevibacter smithii* DSM 2374]
>gi|84489765|ref|YP_447997.1| putative 2-dehydropantoate 2-reductase [*Methanosphaera stadtmanae* DSM 3091]

>gi|319893545|ref|YP_004150420.1| 2-dehydropantoate 2-reductase [*Staphylococcus pseudintermedius* HKU10-03]
>gi|197302450|ref|ZP_03167505.1| hypothetical protein RUMLAC_01178 [*Ruminococcus lactaris* ATCC 29176]
>gi|258542366|ref|YP_003187799.1| ketopantoate reductase ApbA/PanE [*Acetobacter pasteurianus* IFO 3283-01]
>gi|172061542|ref|YP_001809194.1| 2-dehydropantoate 2-reductase [*Burkholderia ambifaria* MC40-6]
>gi|15894883|ref|NP_348232.1| ketopantoate reductase [*Clostridium acetobutylicum* ATCC 624]
>gi|299132927|ref|ZP_07026122.1| 2-dehydropantoate 2-reductase [*Afipia* sp. 1NLS2]
>gi|45657601|ref|YP_001687.1| 2-dehydropantoate 2-reductase [*Leptospira interrogans* serovar Copenhageni str. Fiocruz L1-130]
>gi|238024361|ref|YP_002908593.1| 2-dehydropantoate 2-reductase [*Burkholderia glumae* BGR1]
>gi|154685930|ref|YP_001421091.1| 2-dehydropantoate 2-reductase [*Bacillus amyloliquefaciens* FZB42]
>gi|126180322|ref|YP_001048287.1| 2-dehydropantoate 2-reductase [*Methanoculleus marisnigri* JR1]
>gi|161523150|ref|YP_001586079.1| 2-dehydropantoate 2-reductase [*Burkholderia multivorans* ATCC 17616]
>gi|323528188|ref|YP_004230340.1| 2-dehydropantoate 2-reductase [*Burkholderia* sp. CCGE1001]
>gi|254818916|ref|ZP_05223917.1| 2-dehydropantoate 2-reductase [*Mycobacterium intracellulare* ATCC 13950]
>gi|313498946|gb|ADR60312.1| 2-dehydropantoate 2-reductase [*Pseudomonas putida* BIRD-1]
>gi|22537498|ref|NP_688349.1| 2-dehydropantoate 2-reductase [*Streptococcus agalactiae* 2603V/R]
>gi|123403597|ref|XP_001302267.1| Ketopantoate reductase PanE/ApbA family protein [*Trichomonas vaginalis* G3]
>gi|189348029|ref|YP_001941225.1| 2-dehydropantoate 2-reductase [*Burkholderia multivorans* ATCC 17616]
>gi|222150304|ref|YP_002559457.1| 2-dehydropantoate 2-reductase homolog [*Macrococous caseolyticus* JCSC5402]
>gi|90962337|ref|YP_536253.1| 2-dehydropantoate 2-reductase [*Lactobacillus salivarius* UCC118]
>gi|160900483|ref|YP_001566065.1| 2-dehydropantoate 2-reductase [*Delftia acidovorans* SPH-1]
>gi|297588109|ref|ZP_06946753.1| 2-dehydropantoate 2-reductase [*Finegoldia magna* ATCC 53516]
>gi|299533998|ref|ZP_07047350.1| 2-dehydropantoate 2-reductase [*Comamonas testosteroni* S44]
>gi|291547410|emb|CBL20518.1| 2-dehydropantoate 2-reductase [*Ruminococcus* sp. SR1/5]
>gi|118592425|ref|ZP_01549817.1| 2-dehydropantoate 2-reductase [*Stappia aggregata* IAM 12614]
>gi|254826199|ref|ZP_05231200.1| 2-dehydropantoate 2-reductase [*Listeria monocytogenes* FSL J1-194]
>gi|116670444|ref|YP_831377.1| 2-dehydropantoate 2-reductase [*Arthrobacter* sp. FB24]
>gi|89897521|ref|YP_521008.1| hypothetical protein DSY4775 [*Desulfitobacterium hafniense* Y51]
>gi|293606857|ref|ZP_06689205.1| 2-dehydropantoate 2-reductase [*Achromobacter piechaudii* ATCC 43553]
>gi|126730558|ref|ZP_01746368.1| 2-dehydropantoate 2-reductase [*Sagittula stellata* E-37]
>gi|317133532|ref|YP_004092846.1| 2-dehydropantoate 2-reductase [*Ethanoligenens harbinense* YUAN-3]
>gi|167561774|ref|ZP_02354690.1| 2-dehydropantoate 2-reductase [*Burkholderia oklahomensis* EO147]
>gi|121604457|ref|YP_981786.1| 2-dehydropantoate 2-reductase [*Polaromonas naphthalenivorans* CJ2]
>gi|308173476|ref|YP_003920181.1| 2-dehydropantoate 2-reductase [*Bacillus amyloliquefaciens* DSM 7]
>gi|319939189|ref|ZP_08013552.1| 2-dehydropantoate 2-reductase [*Streptococcus anginosus* 1_2_62CV]
>gi|295136259|ref|YP_003586935.1| ketopantoate reductase PanE/ApbA [*Zunongwangia profunda* SM-A87]
>gi|94263023|ref|ZP_01286842.1| 2-dehydropantoate 2-reductase [delta *proteobacterium* MLMS-1]
>gi|89896295|ref|YP_519782.1| hypothetical protein DSY3549 [*Desulfitobacterium hafniense* Y51]
>gi|314934501|ref|ZP_07841860.1| 2-dehydropantoate 2-reductase [*Staphylococcus caprae* C87]
>gi|167747028|ref|ZP_02419155.1| hypothetical protein ANACAC_01740 [*Anaerostipes caccae* DSM 14662]
>gi|258425014|ref|ZP_05687885.1| 2-dehydropantoate 2-reductase [*Staphylococcus aureus* A9635]
>gi|225180981|ref|ZP_03734429.1| 2-dehydropantoate 2-reductase [*Dethiobacter alkaliphilus* AHT 1]
>gi|296111865|ref|YP_003622247.1| 2-dehydropantoate 2-reductase [*Leuconostoc kimchii* IMSNU 11154]
>gi|311319581|gb|EFQ87840.1| hypothetical protein PTT_16492 [*Pyranophora teres* f. *teres* 0-1]
>gi|225734175|pdb|3G17|A Chain A, Structure Of Putative 2-Dehydropantoate 2-Reductase From *Staphylococcus Aureus*
>gi|315283089|ref|ZP_07871356.1| 2-dehydropantoate 2-reductase [*Listeria marthii* FSL S4-120]
>gi|209543868|ref|YP_002276097.1| 2-dehydropantoate 2-reductase [*Gluconacetobacter diazotrophicus* PAI 5]
>gi|313113024|ref|ZP_07798663.1| 2-denydropantoate 2-reductase [*Faecalibacterium* cf. *prausnitzii* KLE1255]
>gi|291523448|emb|CBK81741.1| ketopantoate reductase [*Coprococcus catus* GD/7]
>gi|260584453|ref|ZP_05852200.1| 2-dehydropantoate 2-reductase [*Granulicatella elegans* ATCC 700633]
>gi|261415325|ref|YP_003249008.1| 2-dehydropantoate 2-reductase [*Fibrobacter succinogenes* subsp. *succinogenes* S85]
>gi|45184780|ref|NP_982498.1| AAL044Cp [*Ashbya gossypii* ATCC 10895]
>gi|255034556|ref|YP_003085177.1| Ketopantoate reductase ApbA/PanE domain proten [*Dyadobacter fermentans* DSM 18053]
>gi|264680193|ref|YP_003280103.1| 2-dehydropantoate 2-reductase [*Comamonas testosteroni* CNB-2]
>gi|148658426|ref|YP_001278631.1| 2-dehydropantoate 2-reductase [*Roseiflexus* sp. RS-1]
>gi|242372246|ref|ZP_04817820.1| 2-dehydropantoate 2-reductase [*Staphylococcus epidermidis* M23864W1]
>gi|225070608|ref|ZP_03779633.1| hypothetical protein CLOHYLEM_06710 [*Clostridium hylemonae* DSM 15053]
>gi|209520519|ref|ZP_03269277.1| 2-dehydropantoate 2-reductase [*Burkholderia* sp. H160]
>gi|217963807|ref|YP_002349485.1| 2-dehydropantoate 2-reductase [*Listeria monocytogenes* HCC23]
>gi|224477588|ref|YP_002635194.1| putative 2-dehydropantoate 2-reductase [*Staphylococcus carnosus* subsp. *carnosus* TM300]
>gi|118462253|ref|YP_883754.1| 2-dehydropantoate 2-reductase [*Mycobacterium avium* 104]
>gi|313672571|ref|YP_004050682.1| 2-dehydropantoate 2-reductase [*Calditerrivibrio nitroreducens* DSM 19672]
>gi|85714020|ref|ZP_01045009.1| 2-dehydropantoate 2-reductase [*Nitrobacter* sp. Nb-311A]

>gi|258593851|emb|CBE70192.1| putative 2-dehydropantoate 2-reductase (Ketopantoate reductase) (KPA reductase) (KPR) [NC10 bacterium 'Dutch sediment']
>gi|160896993|ref|YP_001562575.1| 2-dehydropantoate 2-reductase [*Delftia acidovorans* SPH-1]
>gi|91779353|ref|YP_554561.1| ketopantoate reductase ApbA/PanE [*Burkholderia xenovorans* LB400]
>gi|312795995|ref|YP_004028917.1| Ketopantoate reductase PanE/ApbA family protein [*Burkholderia rhizoxinica* HKI 454]
>gi|227544674|ref|ZP_03974723.1| 2-dehydropantoate 2-reductase [*Lactobacillus reuteri* CF48-3A]
>gi|134098436|ref|YP_001104097.1| 2-dehydropantoate 2-reductase [*Saccharopolyspora erythraea* NRRL 2338]
>gi|222478734|ref|YP_002564971.1| 2-dehydropantoate 2-reductase [*Halorubrum lacusprofundi* ATCC 49239]
>gi|301061481|ref|ZP_07202245.1| 2-dehydropantoate 2-reductase [delta *proteobacterium* NaphS2]
>gi|300024342|ref|YP_003756953.1| 2-dehydropantoate 2-reductase [*Hyphomicrobium denitrificans* ATCC 51888]
>gi|254443388|ref|ZP_05056864.1| 2-dehydropantoate 2-reductase [*Verrucomicrobiae bacterium* DG1235]
>gi|254457455|ref|ZP_05070883.1| 2-dehydropantoate 2-reductase [*Campylobacterales bacterium* GD 1]
>gi|189192294|ref|XP_001932486.1| 2-dehydropantoate 2-reductase [*Pyrenophora tritici-repentis* Pt-1C-BFP]
>gi|114777349|ref|ZP_01452346.1| putative 2-dehydropantoate 2-reductase [*Mariprofundus ferrooxydans* PV-1]
>gi|108805776|ref|YP_645713.1| 2-dehydropantoate 2-reductase [*Rubrobacter xylanophilus* DSM 9941]
>gi|324027764|gb|ADY14523.1| 2-dehydropantoate 2-reductase [*Spirochaeta* sp. Buddy]
>gi|227509602|ref|ZP_03939651.1| 2-dehydropantoate 2-reductase [*Lactobacillus brevis* subsp. *gravesensis* ATCC 27305]
>gi|256847249|ref|ZP_05552695.1| 2-dehydropantoate 2-reductase [*Lactobacillus coleohominis* 101-4-CHN]
>gi|218289275|ref|ZP_03493510.1| 2-dehydropantoate 2-reductase [*Alicyclobacillus acidocaldarius* LAA1]
>gi|68164573|gb|AAY87302.1| predicted ketopantoate reductase [uncultured *bacterium* BAC17H8]
>gi|150016117|ref|YP_001308371.1| 2-dehydropantoate 2-reductase [*Clostridium beijerinckii* NCIMB 8052]
>gi|291550661|emb|CBL26923.1| ketopantoate reductase [*Ruminococcus torques* L2-14]
>gi|163848405|ref|YP_001636449.1| 2-dehydropantoate 2-reductase [*Chloroflexus aurantiacus* J-10-fl]
>gi|302337021|ref|YP_003802227.1| 2-dehydropantoate 2-reductase [*Spirochaeta smaragdinae* DSM 11293]
>gi|253995436|ref|YP_003047500.1| 2-dehydropantoate 2-reductase [*Methylotenera mobilis* JLW8]
>gi|209966707|ref|YP_002299622.1| 2-dehydropantoate 2-reductase [*Rhodospirillum centenum* SW]
>gi|309790241|ref|ZP_07684811.1| hypothetical protein OSCT_0762 [*Oscillochloris trichoides* DG6]
>gi|159491174|ref|XP_001703548.1| ketopantoate reductase [*Chlamydomonas reinhardtii*]
>gi|288556204|ref|YP_003428139.1| 2-dehydropantoate 2-reductase [*Bacillus pseudofirmus* OF4]
>gi|119960789|ref|YP_946726.1| 2-dehydropantoate 2-reductase [*Arthrobacter aurescens* TC1]
>gi|221209631|ref|ZP_03582612.1| 2-dehydropantoate 2-reductase [*Burkholderia multivorans* CGD1]
>gi|149927298|ref|ZP_01915554.1| 2-dehydropantoate 2-reductase [*Limnobacter* sp. MED105]
>gi|255017282|ref|ZP_05289408.1| 2-dehydropantoate 2-reductase [*Listeria monocytogenes* FSL F2-515]
>gi|295700080|ref|YP_003607973.1| 2-dehydropantoate 2-reductase [*Burkholderia* sp. CCGE1002]
>gi|209518576|ref|YP_03267396.1| 2-dehydropantoate 2-reductase [*Burkholderia* sp. H160]
>gi|323528526|ref|YP_004230678.1| 2-dehydropantoate 2-reductase [*Burkholderia* sp. CCGE1001]
>gi|312130704|ref|YP_003998044.1| ketopantoate reductase apba/pano domain protein [*Leadbetterella byssophila* DSM 17132]
>gi|33592466|ref|NP_880110.1| putative ketopantoate reductase [*Bordetella pertussis* Tohama 1]
>gi|156740709|ref|YP_001430838.1| 2-dehydropantoate 2-reductase [*Roseiflexus castenholzii* DSM 13941]
>gi|183980885|ref|YP_001849176.1| ketopantoate reductase, ApoA [*Mycobacterium marinum* M]
>gi|315225886|ref|ZP_07867674.1| 2-dehydropantoate 2-reductase [*Parascardovia denticolens* DSM 10105]
>gi|170692978|ref|ZP_02884139.1| 2-dehydropantoate 2-reductase [*Burkholderia graminis* C4D1M]
>gi|184155218|ref|YP_001843558.1| 2-dehydropantoate 2-reductase [*Lactobacillus fermentum* IFO 3956]
>gi|229824124|ref|ZP_04450193.1| hypothetical protein GCWU000282_01428 [*Catonella morbi* ATCC 51271]
>gi|254557206|ref|YP_003063623.1| 2-dehydropantoate 2-reductase [*Lactobacillus plantarum* JDM1]
>gi|88812802|ref|ZP_01128047.1| 2-dehydropantoate 2-reductase [*Nitrococcus mobilis* Nb-231]
>gi|297625706|ref|YP_003687469.1| Putative 2-dehydropantoate 2-reductase (Ketopantoate reductase) (KPA reductase) (KPR) [*Propionibacterium freudenreichii* subsp. *shermanii* CIRM-BIA1]
>gi|163848886|ref|YP_001636930.1| 2-dehydropantoate 2-reductase [*Chloroflexus aurantiacus* J-10-fl]
>gi|239817446|ref|YP_002946356.1| 2-dehydropantoate 2-reductase [*Vartovorax paradoxus* S110]
>gi|324314617|gb|ADY25732.1| 2-dehydropantoate 2-reductase [*Deinococcus proteolyticus* MRP]
>gi|314934649|ref|ZP_07842008.1| 2-dehydropantoate 2-reductase [*Staphylococcus caprae* C87]
>gi|308270715|emb|CBX27325.1| hypothetical protein N47_H21470 [uncultured *Desulfobacterium* sp.]
>gi|228475460|ref|ZP_04060178.1| 2-dehydropantoate 2-reductase [*Staphylococcus hominis* SK119]
>gi|167618101|ref|ZP_02386732.1| 2-dehydropantoate 2-reductase [*Burkholderia thailandensis* Bt4]
>gi|197122126|ref|YP_002134077.1| 2-dehydropantoate 2-reductase [*Anaeromyxobacter* sp. K]
>gi|92115818|ref|YP_575547.1| 2-dehydropantoate 2-reductase [*Nitrobacter hamburgensis* X14]
>gi|107025901|ref|YP_623412.1| 2-dehydropantoate 2-reductase [*Burkholderia cenocepacia* AU 1054]
>gi|167747378|ref|ZP_02419505.1| hypothetical protein ANACAC_02097 [*Anaerostipes caccae* DSM 14662]
>gi|149188756|ref|ZP_01867047.1| 2-dehydropantoate 2-reductase [*Vibrio shilonii* AK1]
>gi|239628405|ref|ZP_04671436.1| ketopantoate reductase PanE/ApbA [*Clostridiales bacterium* 1_7_47_FAA]
>gi|315659888|ref|ZP_07912747.1| 2-dehydropantoate 2-reductase [*Staphylococcus lugdunensis* M23590]
>gi|257454611|ref|ZP_05619867.1| 2-dehydropantoate 2-reductase [*Enhydrobacter aerosaccus* SK60]
>gi|160940948|ref|ZP_02088288.1| hypothetical protein CLOBOL_05840 [*Clostridium bolteae* ATCC BAA-613]
>gi|167588280|ref|ZP_02380668.1| 2-dehydropantoate 2-reductase [*Burkholderia ubonensis* Bu]
>gi|159125630|gb|EDP50747.1| 2-dehydropantoate 2-reductase [*Aspergillus fumigatus* A1163]

>gi|87199694|ref|YP_496951.1| 2-dehydropantoate 2-reductase [*Novosphingobium aromaticivorans* DSM 12444]
>gi|307727196|ref|YP_003910409.1| 2-dehydropantoate 2-reductase [*Burkholderia* sp. CCGE1003]
>gi|149375503|ref|ZP_01893273.1| 2-dehydropantoate 2-reductase [*Marinobacter algicola* DG893]
>gi|284992269|ref|YP_003410823.1| 2-dehydropantoate 2-reductase [*Geodermatophilus obscurus* DSM 43160]
>gi|319795820|ref|YP_004157460.1| 2-dehydropantoate 2-reductase [*Variovorax paradoxus* EPS]
>gi|311696931|gb|ADP99804.1| ketopantoate reductase ApbA/PanE [marine *bacterium* HP15]
>gi|220916894|ref|YP_002492198.1| 2-dehydropantoate 2-reductase [*Anaeromyxobacter dehalogenans* 2CP-1]
>gi|29832362|ref|NP_826996.1| oxidoreductase [*Streptomyces avermitilis* MA-4680]
>gi|291246372|ref|YP_003505758.1| putative 2-dehydropantoate 2-reductase PanE [*Staphylococcus simulans* bv. *staphylolyticus*]
>gi|73661462|ref|YP_300243.1| 2-dehydropantoate 2-reductase [*Staphylococcus saprophyticus* subsp. *saprophyticus* ATCC 15305]
>gi|266619728|ref|ZP_06112663.1| 2-dehydropantoate 2-reductase [*Clostridium hathewayi* DSM 13479]
>gi|319891385|ref|YP_004148260.1| 2-dehydropantoate 2-reductase [*Staphylococcus pseudintermedius* HKU 10-03]
>gi|258512824|ref|YP_003186258.1| 2-dehydropantoate 2-reductase [*Alicyclobacillus acidocaldarius* subsp. *acidocaldarius* DSM 446]
>gi|296440847|ref|ZP_06882926.1| 2-dehydropantoate 2-reductase [*Clostridium lentocellum* DSM 5427]
>gi|254254805|ref|ZP_04948122.1| Ketopantoate reductase [*Burkholderia dolosa* AUO158]
>gi|222053269|ref|YP_002535631.1| 2-dehydropantoate 2-reductase [*Geobacter* sp. FRC-32]
>gi|89097458|ref|ZP_01170347.1| 2-dehydropantoate 2-reductase [*Bacillus* sp. NRRL B-14911]
>gi|298506713|gb|ADI85436.1| 2-dehydropantoate 2-reductase [*Geobacter sulfurreducens* KN400]
>gi|187919138|ref|YP_001888169.1| 2-dehydropantoate 2-reductase [*Burkholderia phytofirmans* PsJN]
>gi|291246359|ref|YP_003505745.1| putative 2-dehydropantoate 2-reductase PanE [*Staphylococcus simulans* bv. *staphylolyticus*]
>gi|260438889|ref|ZP_05792705.1| 2-dehydropantoate 2-reductase [*Butyrivibrio crossotus* DSM 2876]
>gi|148654505|ref|YP_001274710.1| 2-dehydropantoate 2-reductase [*Roseiflexus* sp. RS-1]
>gi|162146827|ref|YP_001601288.1| 2-dehydropantoate 2-reductase [*Gluconacetobacter diazotrophicus* PAl 5]
>gi|186473315|ref|YP_001860657.1| 2-dehydropantoate 2-reductase [*Burkholderia phymatum* STM815]
>gi|209885679|ref|YP_002289536.1| 2-dehydropantoate 2-reductase [*Oligotropha carboxidovorans* OM5]
>gi|90421544|ref|YP_529914.1| 2-dehydropantoate 2-reductase [*Rhodopseudomonas palustris* BisB18]
>gi|172063745|ref|YP_001811396.1| 2-dehydropantoate 2-reductase [*Burkholderia ambifaria* MC40-6]
>gi|254555474|ref|YP_003061891.1| 2-dehydropantoate 2-reductase [*Lactobacillus plantarum* JDM1]
>gi|253701459|ref|YP_003022648.1| 2-dehydropantoate 2-reductase [*Geobacter* sp. M21]
>gi|108760447|ref|YP_631324.1| 2-dehydropantoate 2-reductase [*Myxococcus xanthus* DK 1622]
>gi|148271549|ref|YP_001221110.1| 2-dehydropantoate 2-reductase [*Clavibacter michiganensis* subsp. *michiganensis* NCPPB 382]
>gi|86158581|ref|YP_465366.1| 2-dehydropantoate 2-reductase [*Anaeromyxobacter dehalogenans* 2CP-C]
>gi|307823565|ref|ZP_07653794.1| 2-dehydropantoate 2-reductase [*Methylobacter tundripaludum* SV96]
>gi|169629992|ref|YP_001703641.1| 2-dehydropantoate 2-reductase [*Mycobacterium abscessus* ATCC 19977]
>gi|114561980|ref|YP_749493.1| 2-dehydropantoate 2-reductase [*Shewanella frigidimarina* NCIMB 400]
>gi|119508832|ref|ZP_01627984.1| 2-dehydropantoate 2-reductase [*Nodularia spumigena* CCY9414]
>gi|86740566|ref|YP_480966.1| 2-dehydropantoate 2-reductase [*Frankia* sp. Ccl3]
>gi|169594880|ref|XP_001790864.1| hypothetical protein SNOG_00170 [*Phaeosphaeria nodorum* SN15]
>gi|27379715|ref|NP_771244.1| 2-dehydropantoate 2-reductase [*Bradyrhizobium japonicum* USDA 110]
>gi|284164004|ref|YP_003402283.1| 2-dehydropantoate 2-reductase [*Haloterrigena turkmenica* DSM 5511]
>gi|241661691|ref|YP_002980051.1| 2-dehydropantoate 2-reductase [*Ralstonia pickerttii* 12D]

APPENDIX 2

Polypeptides of 120-150 Amino Acids with E Value of 0.00001 or Smaller to SEQ ID NO:7 with 95% Identity and 95% Overlap Redundancy Cut-offs >gi|15799815|ref|NP_285827.1| aspartate alpha-decarboxylase [*Escherichia coli* O157:H7 EDL933]
>gi|39654551|pdb|1PT0|A Chain A, Unprocessed Pyruvoyl Dependent Aspartate Decarboxylase With An Alanine Insertion At Position 26
>gi|283783924|ref|YP_003363789.1| aspartate L-decarboxylase [*Citrobacter rodentium* ICC168]
>gi|290512515|ref|ZP_06551881.1| aspartate 1-decarboxylase [*Klebsiella* sp. 1_1_55]
>gi|261338866|ref|ZP_05966724.1| hypothetical protein ENTCAN_05063 [*Enterobacter cancerogenus* ATCC 35316]
>gi|156935344|ref|YP_001439260.1| aspartate alpha-decarboxylase [*Cronobacter sakazakii* ATCC BAA-894]
>gi|283477352|emb|CAY73268.1| panD [*Erwinia pyrifoliae* DSM 12163]
>gi|322834360|ref|YP_004214387.1| aspartate 1-decarboxylase [*Rahnella* sp. Y9602]
>gi|291616317|ref|YP_003519059.1| PanD [*Pantoea ananatis* LMG 20103]
>gi|317493244|ref|ZP_07951666.1| aspartate 1-decarboxylase [*Enterobacteriaceae bacterium* 9_2_54FAA]
>gi|317046954|ref|YP_004114602.1| aspartate 1-decarboxylase [*Pantoea* sp. At-9b]
>gi|251788657|ref|YP_003003378.1| aspartate alpha-decarboxylase [*Dickeya zeae* Ech1591]
>gi|261820473|ref|YP_003258579.1| aspartate 1-decarboxylase [*Pectobacterium wasabiae* WPP163]
>gi|293394524|ref|ZP_06638820.1| aspartate 1-decarboxylase [*Serratia odorifera* DSM 4582]
>gi|292489262|ref|YP_003532149.1| aspartate 1-decarboxylase [*Erwinia amylovora* CFBP1430]
>gi|300715369|ref|YP_003740172.1| Aspartate 1-decarboxylase [*Erwinia billingiae* Eb661]
>gi|197284104|ref|YP_002149976.1| aspartate alpha-decarboxylase [*Proteus mirabilis* HI4320]

>gi|238918726|ref|YP_002932240.1| aspartate alpha-decarboxylase [*Edwardsiella ictaluri* 93-146]
>gi|85058464|ref|YP_454166.1| aspartate alpha-decarboxylase [*Sodalis glossinidius* str. 'morsitans']
>gi|294635062|ref|ZP_06713578.1| aspartate 1-decarboxylase [*Edwardsiella tarda* ATCC 23685]
>gi|320539340|ref|ZP_08039009.1| aspartate 1-decarboxylase [*Serratia symbiotica* str. Tucson]
>gi|37524865|ref|NP_928209.1| aspartate alpha-decarboxylase [*Photorhabdus luminescens* subsp. *laumondii* TT01]
>gi|290476655|ref|YP_003469560.1| aspartate 1-decarboxylase [*Xenorhabdus bovienii* SS-2004]
>gi|183600092|ref|ZP_02961585.1| hypothetical protein PROSTU_03624 [*Providencia stuartii* ATCC 25827]
>gi|291326707|ref|ZP_06125512.2| hypothetical protein PROVRETT_07565 [*Providencia rettgeri* DSM 1131]
>gi|212711314|ref|ZP_03319442.1| hypothetical protein PROVALCAL_02386 [*Providencia alcalifaciens* DSM 30120]
>gi|149910516|ref|ZP_01899156.1| aspartate 1-decarboxylase precursor [*Moritella* sp. PE36]
>gi|148653905|ref|YP_001280998.1| aspartate alpha-decarboxylase [*Psychrobacter* sp. PRwf-1]
>gi|308050924|ref|YP_003914490.1| L-aspartate 1-decarboxylase [*Ferrimonas balearica* DSM 9799]
>gi|90406866|ref|ZP_01215058.1| aspartate 1-decarboxylase precursor [*Psychromonas* sp. CNPT3]
>gi|71064749|ref|YP_263476.1| aspartate alpha-decarboxylase [*Psychrobacter arcticus* 273-4]
>gi|237809047|ref|YP_002893487.1| aspartate 1-decarboxylase [*Tolumonas auensis* DSM 9187]
>gi|291613420|ref|YP_003523577.1| aspartate 1-decarboxylase [*Sideroxydans lithotrophicus* ES-1]
>gi|257455800|ref|ZP_05621026.1| aspartate 1-decarboxylase [*Enhydrobacter aerosaccus* SK60]
>gi|119944351|ref|YP_942031.1| aspartate 1-decarboxylase [*Psychromonas ingrahamii* 37]
>gi|297539336|ref|YP_003675105.1| aspartate 1-decarboxylase [*Methylotenera* sp. 301]
>gi|257094027|ref|YP_003167668.1| aspartate alpha-decarboxylase [*Candidatus Accumulibacter phosphatis* clade IIA str. UW-1]
>gi|253997254|ref|YP_003049318.1| aspartate 1-decarboxylase [*Methylotenera mobilis* JLW8]
>gi|121603845|ref|YP_981174.1| aspartate alpha-decarboxylase [*Polaromonas naphthalenivorans* CJ2]
>gi|220934056|ref|YP_002512955.1| Aspartate 1-decarboxylase [*Thioalkalivibrio* sp. HL-EbGR7]
>gi|91786803|ref|YP_547755.1| aspartate alpha-decarboxylase [*Polaromonas* sp. JS666]
>gi|253999879|ref|YP_003051942.1| aspartate 1-decarboxylase [*Methylovorus* sp. SIP3-4]
>gi|167835820|ref|ZP_02462703.1| aspartate alpha-decarboxylase [*Burkholderia thailandensis* MSMB43]
>gi|71908800|ref|YP_286387.1| aspartate alpha-decarboxylase [*Dechloromonas aromatica* RCB]
>gi|323525130|ref|YP_004227283.1| aspartate 1-decarboxylase [*Burkholderia* sp. CCGE1001]
>gi|53803579|ref|YP_114732.1| aspartate alpha-decarboxylase [*Methylococcus capsulatus* str. Bath]
>gi|302879352|ref|YP_003847916.1| aspartate 1-decarboxylase [*Gallionella capsiferriformans* ES-2]
>gi|89901803|ref|YP_524274.1| aspartate alpha-decarboxylase [*Rhodoferax ferrireducens* T118]
>gi|239820653|ref|YP_002947838.1| aspartate 1-decarboxylase [*Variovorax paradoxus* S110]
>gi|34497092|ref|NP_901307.1| aspartate alpha-decarboxylase [*Chromobacterium violaceum* ATCC 12472]
>gi|167585777|ref|ZP_02378165.1| aspartate alpha-decarboxylase [*Burkholderia ubonensis* Bu]
>gi|239815072|ref|YP_002943982.1| aspartate 1-decarboxylase [*Variovorax paradoxus* S110]
>gi|91774949|ref|YP_544705.1| aspartate alpha-decarboxylase [*Methylobacillus flagellatus* KT]
>gi|254447307|ref|ZP_05060774.1| aspartate 1-decarboxylase [gamma *proteobacterium* HTCC5015]
>gi|186476949|ref|YP_001858419.1| aspartate alpha-decarboxylase [*Burkholderia phymatum* STM815]
>gi|74318073|ref|YP_315813.1| aspartate alpha-decarboxylase [*Thiobacillus denitrificans* ATCC 25259]
>gi|254429606|ref|ZP_05043313.1| aspartate 1-decarboxylase [*Alcanivorax* sp. DG881]
>gi|78067243|ref|YP_370012.1| aspartate alpha-decarboxylase [*Burkholderia* sp. 383]
>gi|169796983|ref|YP_001714776.1| aspartate alpha-decarboxylase [*Acinetobacter baumannii* AYE]
>gi|307546720|ref|YP_003899199.1| aspartate 1-decarboxylase [*Halomonas elongata* DSM 2581]
>gi|224825655|ref|ZP_03698759.1| aspartate 1-decarboxylase [*Lutiella nitroferrum* 2002]
>gi|262369399|ref|ZP_06062727.1| aspartate 1-decarboxylase [*Acinetobacter johnsonii* SH046]
>gi|262376653|ref|ZP_06069881.1| aspartate 1-decarboxylase [*Acinetobacter lwoffii* SH145]
>gi|241766440|ref|ZP_04764313.1| aspartate 1-decarboxylase [*Acidovorax delafieldii* 2AN]
>gi|161524030|ref|YP_001579042.1| aspartate alpha-decarboxylase [*Burkholderia multivorans* ATCC 17616]
>gi|288942456|ref|YP_003444696.1| aspartate 1-decarboxylase [*Allochromatium vinosum* DSM 180]
>gi|299137499|ref|ZP_07030680.1| aspartate 1-decarboxylase [*Acidobacterium* sp. MP5ACTX8]
>gi|238028348|ref|YP_002912579.1| hypothetical protein bglu_1g28090 [*Burkholderia glumae* BGR1]
>gi|71901432|ref|ZP_00683522.1| Aspartate decarboxylase [*Xylella fastidiosa* Ann-1]
>gi|71276366|ref|ZP_00652643.1| Aspartate decarboxylase [*Xylella fastidiosa* Dixon]
>gi|94500961|ref|YP_01307486.1| aspartate 1-decarboxylase precursor [*Oceanobacter* sp. RED65]
>gi|149927699|ref|ZP_01915951.1| aspartate alpha-decarboxylase [*Limnobacter* sp. MED 105]
>gi|90020709|ref|YP_526536.1| aspartate 1-decarboxylase [*Saccharophagus degradans* 2-40]
>gi|254491956|ref|ZP_05105134.1| aspartate 1-decarboxylase [*Methylophaga thiooxidans* DMS010]
>gi|92115182|ref|YP_575110.1| aspartate alpha-decarboxylase [*Chromohalobacter salexigens* DSM 3043]
>gi|78485863|ref|YP_391788.1| aspartate alpha-decarboxylase [*Thiomicrospira crunogena* XCL-2]
>gi|307826254|ref|ZP_07656463.1| aspartate 1-decarboxylase [*Methylobacter tundripaludum* SV96]
>gi|89093284|ref|ZP_01166234.1| aspartate 1-decarboxylase [*Oceanospirillum* sp. MED92]
>gi|146283618|ref|YP_001173771.1| aspartate alpha-decarboxylase [*Pseudomonas stutzeri* A1501]
>gi|264679999|ref|YP_003279908.1| aspartate 1-decarboxylase [*Comamonas testosteroni* CNB-2]
>gi|116052878|ref|YP_793195.1| aspartate alpha-decarboxylase [*Pseudomonas aeruginosa* UCBPP-PA14]
>gi|160897278|ref|YP_001562860.1| aspartate alpha-decarboxylase [*Delftia acidovorans* SPH-1]

>gi|121997470|ref|YP_001002257.1| aspartate 1-decarboxylase [*Halorhodospira halophila* SL1]
>gi|38372456|sp|Q848I5.1| PAND_PSEFL RecName: Full=Aspartate 1-decarboxylase;
>gi|21231219|ref|NP_637136.1| aspartate alpha-decarboxylase [*Xanthomonas campestris* pv. *campestris* str. ATCC 33913]
>gi|319949737|ref|ZP_08023765.1| aspartate alpha-decarboxylase [*Dietzia cinnamea* P4]
>gi|226940325|ref|YP_002795399.1| PanD [*Laribacter hongkongensis* HLHK9]
>gi|88800686|ref|ZP_01116245.1| aspartate 1-decarboxylase precursor [*Reinekea* sp. MED297]
>gi|194365298|ref|YP_002027908.1| aspartate alpha-decarboxylase [*Stenotrophomonas maltophilia* R551-3]
>gi|254469038|ref|ZP_05082444.1| aspartate 1-decarboxylase [beta proteobacterium KB13]
>gi|188576407|ref|YP_001913336.1| aspartate alpha-decarboxylase [*Xanthomonas oryzae* pv. *oryzae* PXO99A]
>gi|171059338|ref|YP_001791687.1| aspartate 1-decarboxylase [*Leptothrix cholodnii* SP-6]
>gi|121595787|ref|YP_987683.1| aspartate alpha-decarboxylase [*Acidovorax* sp. JS42]
>gi|289209202|ref|YP_003461268.1| aspartate 1-decarboxylase [*Thioalkalivibrio* sp. K90mix]
>gi|213965138|ref|ZP_03393336.1| aspartate 1-decarboxylase [*Corynebacterium amycolatum* SK46]
>gi|91787463|ref|YP_548415.1| aspartate alpha-decarboxylase [*Polaromonas* sp. JS666]
>gi|254784766|ref|YP_003072194.1| aspartate 1-decarboxylase [*Teredinibacter turnerae* T7901]
>gi|187478858|ref|YP_786882.1| aspartate 1-decarboxylase [*Bordetella avium* 197N]
>gi|114776473|ref|ZP_01451518.1| aspartate 1-decarboxylase precursor [*Mariprofundus ferrooxydans* PV-1]
>gi|226946298|ref|YP_002801371.1| aspartate alpha-decarboxylase [*Azotobacter vinelandii* DJ]
>gi|118594493|ref|ZP_01551840.1| aspartate 1-decarboxylase precursor [*Methylophilales bacterium* HTCC2181]
>gi|87118637|ref|ZP_01074536.1| putative aspartate 1-decarboxylase [*Marinomonas* sp. MED121]
>gi|285017994|ref|YP_003375705.1| aspartate 1-decarboxylase precursor (aspartate alpha-decarboxylase) protein [*Xanthomonas albilineans* GPE PC73]
>gi|83859460|ref|ZP_00952981.1| aspartate 1-decarboxylase [*Oceanicaulis alexandrii* HTCC2633]
>gi|319786659|ref|YP_004146134.1| aspartate 1-decarboxylase [*Pseudoxanthomonas suwonensis* 11-1]
>gi|152995292|ref|YP_001340127.1| aspartate 1-decarboxylase [*Marinomonas* sp. MWYL1]
>gi|194290690|ref|YP_002006597.1| aspartate alpha-decarboxylase [*Cupriavidus taiwanensis* LMG 19424]
>gi|162449208|ref|YP_001611575.1| hypothetical protein sce0938 [*Sorangium cellulosum* 'So ce 56']
>gi|153003251|ref|YP_001377576.1| aspartate 1-decarboxylase [*Anaeromyxobacter* sp. Fw109-5]
>gi|293604513|ref|ZP_06686918.1| aspartate 1-decarboxylase [*Achromobacter piechaudii* ATCC 43553]
>gi|289704810|ref|ZP_06501229.1| aspartate 1-decarboxylase [*Micrococcus luteus* SK58]
>gi|237749062|ref|ZP_04579542.1| aspartate 1-decarboxylase [*Oxalobacter formigenes* OXCC13]
>gi|255020069|ref|YP_05292141.1| Aspartate 1-decarboxylase [*Acidithiobacillus caldus* ATCC51756]
>gi|119962044|ref|YP_949406.1| aspartate 1-decarboxylase [*Arthrobacter aurescens* TC1]
>gi|15805744|ref|NP_294441.1| aspartate alpha-decarboxylase [*Deinococcus radiodurans* R1]
>gi|197124548|ref|YP_002136499.1| aspartate 1-decarboxylase [*Anaeromyxobacter* sp. K]
>gi|300310032|ref|YP_003774124.1| aspartate 1-decarboxylase precursor protein [*Herbaspirillum seropedicae* SmR1]
>gi|77164404|ref|YP_342929.1| aspartate alpha-decarboxylase [*Nitrosococcus oceani* ATCC 19707]
>gi|158706108|sp|Q1IYG7.2|PAND_DEIGD RecName: Full=Aspartate 1-decarboxylase;
>gi|183985072|ref|YP_001853363.1| aspartate 1-decarboxylase precursor PanD [*Mycobacterium marinum* M]
>gi|291287339|ref|YP_003504155.1| aspartate 1-decarboxylase [*Denitrovibrio acetiphilus* DSM 12809]
>gi|302870300|ref|YP_003838937.1| aspartate 1-decarboxylase [*Micromonospora aurantiaca* ATCC 27029]
>gi|296040174|ref|ZP_06832727.1| aspartate 1-decarboxylase [*Rhodococcus equi* ATCC 33707]
>gi|153870646|ref|ZP_02000002.1| Aspartate decarboxylase [*Beggiatoa* sp. PS]
>gi|148271711|ref|YP_001221272.1| aspartate alpha-decarboxylase [*Clavibacter michiganensis* subsp. *michiganensis* NCPPB 382]
>gi|300690455|ref|YP_003751450.1| aspartate 1-decarboxylase [*Ralstonia solanacearum* PSI07]
>gi|292491194|ref|YP_003526633.1| aspartate 1-decarboxylase [*Nitrosococcus halophilus* Nc4]
>gi|300703064|ref|YP_003744666.1| aspartate 1-decarboxylase [*Ralstonia solanacearum* CFBP2957]
>gi|187930038|ref|YP_001900525.1| aspartate alpha-decarboxylase [*Ralstonia pickettii* 12J]
>gi|41406555|ref|NP_959391.1| aspartate alpha-decarboxylase [*Mycobacterium avium* subsp. *paratuberculosis* K-10]
>gi|169627646|ref|YP_001701295.1| aspartate 1-decarboxylase precursor [*Mycobacterium abscessus* ATCC 19977]
>gi|192360161|ref|YP_001983429.1| aspartate 1-decarboxylase [*Cellvibrio japonicus* Ueda107]
>gi|320094682|ref|ZP_08026439.1| aspartate 1-decarboxylase [*Actinomyces* sp. oral taxon 178 str. F0338]
>gi|283778561|ref|YP_003369316.1| aspartate 1-decarboxylase [*Pirellula staleyi* DSM 6068]
>gi|256789458|ref|ZP_05527889.1| aspartate alpha-decarboxylase [*Streptomyces lividans* TK24]
>gi|291297625|ref|YP_003508903.1| aspartate 1-decarboxylase [*Stackebrandtia nassauensis* DSM 44728]
>gi|55980575|ref|YP_143872.1| aspartate alpha-decarboxylase [*Thermus thermophilus* HB8]
>gi|120406311|ref|YP_956140.1| aspartate alpha-decarboxylase [*Mycobacterium vanbaalenii* PYR-1]
>gi|119475802|ref|ZP_01616154.1| aspartate 1-decarboxylase precursor [marine gamma proteobacterium HTCC2143]
>gi|114319727|ref|YP_741410.1| aspartate alpha-decarboxylase [*Alkalilimnicola ehrlichii* MLHE-1]
>gi|90416572|ref|ZP_01224503.1| aspartate 1-decarboxylase precursor [marine gamma proteobacterium HTCC2207]
>gi|184200024|ref|YP_001854231.1| aspartate 1-decarboxylase precursor [*Kocuria rhizophila* DC2201]
>gi|72162261|ref|YP_289918.1| aspartate alpha-decarboxylase [*Thermobifida fusca* YX]
>gi|154507911|ref|ZP_02043553.1| hypothetical protein ACTODO_00396 [*Actinomyces odontolyticus* ATCC 17982]

>gi|319442411|ref|ZP_07991567.1| aspartate alpha-decarboxylase [*Corynebacterium variabile* DSM 44702]
>gi|225028053|ref|ZP_03717245.1| hypothetical protein EUBHAL_02322 [*Eubacterium hallii* DSM 3353]
>gi|271970326|ref|YP_003344522.1| aspartate 1-decarboxylase [*Streptosporangium roseum* DSM 43021]
>gi|296138304|ref|YP_003645547.1| aspartate 1-decarboxylase [*Tsukamurella paurometabola* DSM 20162]
>gi|226304123|ref|YP_002764081.1| aspartate 1-decarboxylase [*Rhodococcus erythropolis* PR4]
>gi|145588837|ref|YP_001155434.1| aspartate alpha-decarboxylase [*Polynucleobacter necessarius* subsp. *asymbioticus* QLW-P1DMWA-1]
>gi|108801724|ref|YP_641921.1| aspartate alpha-decarboxylase [*Mycobacterium* sp. MCS]
>gi|323489711|ref|ZP_08094938.1| aspartate 1-decarboxylase [*Planococcus donghaensis* MPA1U2]
>gi|320450484|ref|YP_004202580.1| aspartate 1-decarboxylase [*Thermus scotoductus* SA-01]
>gi|240172844|ref|ZP_04751503.1| aspartate alpha-decarboxylase [*Mycobacterium kansasii* ATCC 12478]
>gi|148264137|ref|YP_001230843.1| aspartate alpha-decarboxylase [*Geobacter uraniireducens* Rf4]
>gi|302562209|ref|ZP_07314551.1| aspartate 1-decarboxylase [*Streptomyces griseoflavus* Tu4000]
>gi|197119382|ref|YP_002139809.1| aspartate alpha-decarboxylase [*Geobacter bemidjiensis* Bem]
>gi|15610737|ref|NP_218118.1| aspartate alpha-decarboxylase [*Mycobacterium tuberculosis* H37Rv]
>gi|159040208|ref|YP_001539461.1| aspartate alpha-decarboxylase [*Salinispora arenicola* CNS-205]
>gi|237746908|ref|ZP_04577388.1| aspartate-1-decarboxylase [*Oxalobacter formigenes* HOxBLS]
>gi|52080749|ref|YP_079540.1| aspartate alpha-decarboxylase [*Bacillus licheniformis* ATCC 14580]
>gi|296113074|ref|YP_003627012.1| aspartate 1-decarboxylase [*Moraxella catarrhalis* RH4]
>gi|111021388|ref|YP_704360.1| aspartate alpha-decarboxylase [*Rhodococcus jostii* RHA1]
>gi|298368957|ref|ZP_06980275.1| aspartate 1-decarboxylase [*Neisseria* sp. oral taxon 014 str. F0314]
>gi|315446243|ref|YP_004079122.1| L-aspartate 1-decarboxylase [*Mycobacterium* sp. Spyr1]
>gi|297190372|ref|YP_06907770.1| aspartate 1-decarboxylase [*Streptomyces pristinaespiralis* ATCC 25486]
>gi|315924106|ref|ZP_07920332.1| aspartate 1-decarboxylase [*Pseudoramibacter alactolyticus* ATCC 23263]
>gi|15677149|ref|NP_274302.1| aspartate alpha-decarboxylase [*Neisseria meningitidis* MC58]
>gi|239980059|ref|ZP_04702583.1| aspartate alpha-decarboxylase [*Streptomyces albus* J1074]
>gi|15827028|ref|NP_301291.1| aspartate alpha-decarboxylase [*Mycobacterium leprae* TN]
>gi|116672429|ref|YP_833362.1| aspartate alpha-decarboxylase [*Arthrobacter* sp. FB24]
>gi|229918730|ref|YP_002887376.1| aspartate 1-decarboxylase [*Exiguobacterium* sp. AT 1b]
>gi|238020351|ref|ZP_04600777.1| hypothetical protein GCWU000324_00231 [*Kingella oralis* ATCC 51147]
>gi|163840966|ref|YP_001625371.1| aspartate alpha-decarboxylase [*Renibacterium salmoninarum* ATCC 33209]
>gi|68535357|ref|YP_250062.1| aspartate alpha-decarboxylase [*Corynebacterium jeikeium* K411]
>gi|117927421|ref|YP_871972.1| L-aspartate 1-decarboxylase [*Acidothermus cellulolyticus* 11B]
>gi|124268753|ref|YP_001022757.1| aspartate alpha-decarboxylase [*Methylibium petroleiphilum* PM1]
>gi|220914411|ref|YP_002489720.1| aspartate 1-decarboxylase [*Arthrobacter chlorophenolicus* A6]
>gi|108758834|ref|YP_634947.1| aspartate 1-decarboxylase [*Myxococcus xanthus* DK 1622]
>gi|269218264|ref|ZP_06162118.1| aspartate 1-decarboxylase [*Actinomyces* sp. oral taxon 848 str. F0332]
>gi|311743353|ref|ZP_07717160.1| aspartate 1-decarboxylase [*Aeromicrobium marinum* DSM 15272]
>gi|145596791|ref|YP_001161088.1| aspartate alpha-decarboxylase [*Salinispora tropica* CNB-440]
>gi|198284767|ref|YP_002221088.1| aspartate 1-decarboxylase [*Acidithiobacillus ferrooxidans* ATCC 53993]
>gi|308178526|ref|YP_003917932.1| aspartate 1-decarboxylase [*Arthrobacter arilaitensis* Re117]
>gi|255065696|ref|ZP_05317551.1| aspartate 1-decarboxylase [*Neisseria sicca* ATCC 29256]
>gi|88810485|ref|ZP_01125742.1| aspartate 1-decarboxylase precursor [*Nitrococcus mobilis* Nb-231]
>gi|158706097|sp|A1SDW8.2|PAND_NOCSJ RecName: Full=Aspartate 1-decarboxylase;
>gi|172041372|ref|YP_001801086.1| aspartate alpha-decarboxylase [*Corynebacterium urealyticum* DSM 7109]
>gi|291297729|ref|YP_003509007.1| aspartate 1-decarboxylase [*Stackebrandtia nassauensis* DSM 44728]
>gi|294675086|ref|YP_003575702.1| aspartate 1-decarboxylase [*Prevotella ruminicola* 23]
>gi|291519794|emb|CBK75015.1| L-aspartate 1-decarboxylase [*Butyrivibrio fibrisolvens* 16/4]
>gi|78042854|ref|YP_361172.1| aspartate alpha-decarboxylase [*Carboxydothermus hydrogenoformans* Z-2901]
>gi|54022371|ref|YP_116613.1| aspartate alpha-decarboxylase [*Nocardia farcinica* IFM 10152]
>gi|153815600|ref|ZP_01968268.1| hypothetical protein RUMTOR_01836 [*Ruminococcus torques* ATCC 27756]
>gi|119952798|ref|YP_950285.1| aspartate 1-decarboxylase [*Arthrobacter aurescens* TC1]
>gi|118581933|ref|YP_903183.1| aspartate alpha-decarboxylase [*Pelobacter propionicus* DSM 2379]
>gi|308174032|ref|YP_003920737.1| aspartate 1-decarboxylase [*Bacillus amyloliquefaciens* DSM 7]
>gi|227498405|ref|ZP_03928551.1| aspartate alpha-decarboxylase [*Acidaminococcus* sp. D21]
>gi|261880070|ref|YP_06006497.1| aspartate 1-decarboxylase [*Prevotella bergensis* DSM 17361]
>gi|284989228|ref|YP_003407782.1| aspartate 1-decarboxylase [*Geodermatophilus obscurus* DSM 43160]
>gi|89099887|ref|ZP_01172759.1| aspartate 1-decarboxylase precursor [*Bacillus* sp. NRRL B-14911]
>gi|296271376|ref|YP_003654008.1| aspartate 1-decarboxylase [*Thermobispora bispora* DSM 43833]
>gi|168698967|ref|ZP_02731244.1| hypothetical protein GobsU_05571 [*Gemmata obscuriglobus* UQM 2246]
>gi|220929206|ref|YP_002506115.1| aspartate 1-decarboxylase [*Clostridium cellulolyticum* H10]
>gi|84495005|ref|ZP_00994124.1| aspartate 1-decarboxylase precursor [*Janibacter* sp. HTCC2649]
>gi|291547262|emb|CBL20370.1| L-aspartate 1-decarboxylase [*Ruminococcus* sp. SR1/5]
>gi|298246275|ref|ZP_06970081.1| aspartate 1-decarboxylase [*Ktedonobacter racemifer* DSM 44963]
>gi|150017466|ref|YP_001309720.1| aspartate alpha-decarboxylase [*Clostridium beijerinckii* NCIMB 8052]
>gi|300934633|ref|ZP_07149889.1| aspartate alpha-decarboxylase [*orynebacterium resistens* DSM 45100]
>gi|269124634|ref|YP_003298004.1| aspartate 1-decarboxylase [*Thermomonospora curvata* DSM 43183]

>gi|269128681|ref|YP_003302051.1| aspartate 1-decarboxylase [*Thermomonospora curvata* DSM 43183]
>gi|307244703|ref|ZP_07526806.1| aspartate 1-decarboxylase [*Peptostreptococcus stomatis* DSM 17678]
>gi|282862735|ref|ZP_06271796.1| aspartate 1-decarboxylase [*Streptomyces* sp. ACTE]
>gi|227494386|ref|ZP_03924702.1| aspartate 1-decarboxylase [*Actinomyces coleocanis* DSM 15436]
>gi|268316317|ref|YP_003290036.1| aspartate 1-decarboxylase [*Rhodothermus marinus* DSM 4252]
>gi|226312091|ref|YP_002771985.1| aspartate 1-decarboxylase precursor [*Brevibacillus brevis* NBRC 100599]
>gi|308069472|ref|YP_003871077.1| Aspartate 1-decarboxylase precursor (Aspartate alpha-decarboxylase) [*Paenibacillus polymyxa* E681]
>gi|121535059|ref|ZP_01666876.1| aspartate 1-decarboxylase [*Thermosinus carboxydivorans* Nor1]
>gi|29376392|ref|NP_815546.1| aspartate alpha-decarboxylase [*Enterococcus faecalis* V583]
>gi|172057787|ref|YP_001814247.1| aspartate 1-decarboxylase [*Exiguobacterium sibiricum* 255-15]
>gi|289522732|ref|ZP_06439586.1| aspartate 1-decarboxylase [*Anaerobaculum hydrogeniformans* ATCC BAA-1850]
>gi|315605842|ref|ZP_07880874.1| aspartate 1-decarboxylase [*Actinomyces* sp. oral taxon 180 str. F0310]
>gi|255994546|ref|ZP_05427681.1| aspartate 1-decarboxylase [*Eubacterium saphenum* ATCC 49989]
>gi|251796457|ref|YP_003011188.1| aspartate 1-decarboxylase [*Paenibacillus* sp. JDR-2]
>gi|54295766|ref|YP_128181.1| aspartate alpha-decarboxylase [*Legionella pneumophila* str. Lens]
>gi|258654511|ref|YP_003203667.1| aspartate 1-decarboxylase [*Nakamurella multipartita* DSM 44233]
>gi|311068755|ref|YP_003973678.1| aspartate alpha-decarboxylase [*Bacillus atrophaeus* 1942]
>gi|229544027|ref|ZP_04433086.1| aspartate 1-decarboxylase [*Bacillus coagulans* 36D1]
>gi|257068435|ref|YP_003154690.1| L-aspartate 1-decarboxylase [*Brachybacterium faecium* DSM 4810]
>gi|256753469|ref|ZP_05494262.1| aspartate 1-decarboxylase [*Clostridium papyrosolvens* DSM 2782]
>gi|324980408|gb|EGC16074.1| aspartate 1-decarboxylase [*Kingella denitrificans* ATCC 33394]
>gi|225075174|ref|ZP_03718373.1| hypothetical protein NEIFLAOT_00174 [*Neisseria flavescens* NRL30031/H210]
>gi|258510312|ref|YP_003183746.1| aspartate 1-decarboxylase [*Alicyclobacillus acidocaldarius* subsp. *acidocaldarius* DSM 446]
>gi|309813243|ref|ZP_07706964.1| aspartate 1-decarboxylase [*Dermacoccus* sp. Ellin185]
>gi|77919424|ref|YP_357239.1| aspartate alpha-decarboxylase [*Pelobacter carbinolicus* DSM 2380]
>gi|124009556|ref|ZP_01694230.1| aspartate 1-decarboxylase [*Microscilla marina* ATCC 23134]
>gi|320007101|gb|ADW01951.1| aspartate 1-decarboxylase [*Streptomyces flavogriseus* ATCC 33331]
>gi|299538597|ref|ZP_07051880.1| aspartate 1-decarboxylase precursor [*Lysinibacillus fusiformis* ZC1]
>gi|225017697|ref|ZP_03706889.1| hypothetical protein CLOSTMETH_01626 [*Clostridium methylpentosum* DSM 5476]
>gi|256397482|ref|YP_003119046.1| aspartate 1-decarboxylase [*Catenulispora acidiphila* DSM 44928]
>gi|320006702|gb|ADW01552.1| aspartate 1-decarboxylase [*Streptomyces flavogriseus* ATCC 33331]
>gi|323471151|gb|ADX74836.1| L-aspartate 1-decarboxylase [*Arthrobacter phenanthrenivorans* Sphe3]
>gi|25026691|ref|NP_736745.1| aspartate alpha-decarboxylase [*Corynebacterium efficiens* YS-314]
>gi|16079298|ref|NP_390122.1| aspartate alpha-decarboxylase [*Bacillus subtilis* subsp. *subtilis* str. 168]
>gi|319790447|ref|YP_004152080.1| aspartate 1-decarboxylase [*Thermovibrio ammonificans* HB-1]
>gi|251779952|ref|ZP_04822872.1| aspartate 1-decarboxylase [*Clostridium botulinum* E1 str. 'BoNT E Beluga']
>gi|167462328|ref|ZP_02327417.1| aspartate alpha-decarboxylase [*Paenibacillus larvae* subsp. *larvae* BRL-230010]
>gi|225025397|ref|ZP_03714589.1| hypothetical protein EIKCOROL_02295 [*Eikenella corrodens* ATCC 23834]
>gi|291279242|ref|YP_003496077.1| aspartate 1-decarboxylase [*Deferribacter desulfuricans* SSM1]
>gi|311896800|dbj|BAJ29208.1| putative L-aspartate 1-decarboxylase [*Kitasatospora setae* KM-6054]
>gi|169827548|ref|YP_001697706.1| aspartate 1-decarboxylase [*Lysinibacillus sphaericus* C3-41]
>gi|299134421|ref|ZP_07027614.1| aspartate 1-decarboxylase [*Afipia* sp. 1NLS2]
>gi|242372243|ref|ZP_04817817.1| aspartate alpha-decarboxylase [*Staphylococcus epidermidis* M23864:W1]
>gi|226325379|ref|ZP_03800897.1| hypothetical protein COPCOM_03181 [*Coprococcus comes* ATCC 27758]
>gi|284029184|ref|YP_003379115.1| aspartate 1-decarboxylase [*Kribbella flavida* DSM 17836]
>gi|319651315|ref|ZP_08005445.1| aspartate 1-decarboxylase [*Bacillus* sp. 2_A_57_CT2]
>gi|254496676|ref|ZP_05109539.1| aspartate alpha-decarboxylase [*Legionella drancourtii* LLAP12]
>gi|256833308|ref|YP_003162035.1| aspartate 1-decarboxylase [*Jonesia denitrificans* DSM 20603]
>gi|261417985|ref|YP_003251667.1| aspartate 1-decarboxylase [*Geobacillus* sp. Y412MC61]
>gi|302876569|ref|YP_003845202.1| aspartate 1-decarboxylase [*Clostridium cellulovorans* 743B]
>gi|212638969|ref|YP_002315489.1| aspartate alpha-decarboxylase [*Anoxybacillus flavithermus* WK1]
>gi|15896169|ref|NP_349518.1| aspartate alpha-decarboxylase [*Clostridium acetobutylicum* ATCC 824]
>gi|304406905|ref|ZP_07388559.1| aspartate 1-decarboxylase [*Paenibacillus curdlanolyticus* YK9]
>gi|317128616|ref|YP_004094898.1| aspartate 1-decarboxylase [*Bacillus cellulosilyticus* DSM 2522]
>gi|149183103|ref|ZP_01861554.1| aspartate 1-decarboxylase precursor [*Bacillus* sp. SG-1]
>gi|169335507|ref|ZP_02862700.1| hypothetical protein ANASTE_01921 [*Anaerofustis stercorihominis* DSM 17244]
>gi|197303353|ref|ZP_03168393.1| hypothetical protein RUMLAC_02076 [*Ruminococcus lactaris* ATCC 29176]
>gi|268608082|ref|ZP_06141811.1| aspartate alpha-decarboxylase [*Ruminococcus flavefaciens* FD-1]
>gi|294789798|ref|ZP_06755027.1| aspartate 1-decarboxylase [*Simonsiella muelleri* ATCC 29453]
>gi|49484793|ref|YP_042017.1| aspartate alpha-decarboxylase [*Staphylococcus aureus* subsp. *aureus* MRSA252]
>gi|28377460|ref|NP_784352.1| aspartate alpha-decarboxylase [*Lactobacillus plantarum* WCFS1]
>gi|182418494|ref|ZP_02949787.1| aspartate 1-decarboxylase [*Clostridium butyricum* 5521]
>gi|302553297|ref|ZP_07305639.1| aspartate 1-decarboxylase [*Streptomyces viridochromogenes* DSM 40736]

>gi|159896918|ref|YP_001543165.1| aspartate 1-decarboxylase [*Herpetosiphon aurantiacus* ATCC 23779]
>gi|114570673|ref|YP_757353.1| aspartate alpha-decarboxylase [*Maricaulis maris* MCS10]
>gi|239827468|ref|YP_002950092.1| aspartate 1-decarboxylase [*Geobacillus* sp. WCH70]
>gi|323465432|gb|ADX77585.1| aspartate 1-decarboxylase [*Staphylococcus pseudintermedius* ED99]
>gi|182434568|ref|YP_001822287.1| aspartate alpha-decarboxylase [*Streptomyces griseus* subsp. *griseus* NBRC 13350]
>gi|149178749|ref|ZP_01857332.1| aspartate 1-decarboxylase [*Planctomyces maris* DSM 8797]
>gi|297616344|ref|YP_003701503.1| aspartate 1-decarboxylase [*Syntrophothermus lipocalidus* DSM 12680]
>gi|83816527|ref|YP_445536.1| aspartate 1-decarboxylase [*Salinibacter ruber* DSM 13855]
>gi|288556128|ref|YP_003428063.1| aspartate alpha-decarboxylase [*Bacillus pseudofirmus* OF4]
>gi|239635857|ref|ZP_04676881.1| aspartate 1-decarboxylase [*Staphylococcus warneri* L37603]
>gi|302342373|ref|YP_003806902.1| aspartate 1-decarboxylase [*Desulfarculus baarsii* DSM 2075]
>gi|146297697|ref|YP_001181468.1| aspartate 1-decarboxylase [*Caldicellulosiruptor saccharolyticus* DSM 8903]
>gi|147676557|ref|YP_001210772.1| aspartate alpha-decarboxylase [*Pelotomaculum thermopropionicum* SI]
>gi|138895755|ref|YP_001126208.1| aspartate alpha-decarboxylase [*Geobacillus thermodenitrificans* NG80-2]
>gi|193215499|ref|YP_001996698.1| aspartate alpha-decarboxylase [*Chloroherpeton thalassium* ATCC 35110]
>gi|270158276|ref|ZP_06186933.1| aspartate 1-decarboxylase [*Legionella longbeachae* D-4968]
>gi|154483470|ref|ZP_02025918.1| hypothetical protein EUBVEN_01174 [*Eubacterium ventriosum* ATCC 27560]
>gi|19551386|ref|NP_599388.1| aspartate alpha-decarboxylase [*Corynebacterium glutamicum* ATCC 13032]
>gi|269956437|ref|YP_003326226.1| aspartate 1-decarboxylase [*Xylanimonas cellulosilytica* DSM 15894]
>gi|154491071|ref|ZP_02031012.1| hypothetical protein PARMER_00990 [*Parabacteroides merdae* ATCC 43184]
>gi|164511440|emb|CAN89641.1| putative aspartate-1-decarboxylase precursor [*Streptomyces collinus*]
>gi|284044344|ref|YP_003394684.1| aspartate 1-decarboxylase [*Conexibacter woesei* DSM 14684]
>gi|300786909|ref|YP_003767200.1| aspartate 1-decarboxylase [*Amycolatopsis mediterranei* U32]
>gi|118443940|ref|YP_877157.1| aspartate alpha-decarboxylase [*Clostridium novyi* NT]
>gi|294671143|ref|ZP_06735998.1| hypothetical protein NEIELOOT_02851 [*Neisseria elongata* subsp. *glycolytica* ATCC 29315]
>gi|317499217|ref|ZP_07957492.1| aspartate decarboxylase [*Lachnospiraceae bacterium* 5_1_63FAA]
>gi|300087723|ref|YP_003758245.1| aspartate 1-decarboxylase [*Dehalogenimonas lykanthroporepellens* BL-DC-9]
>gi|312792944|ref|YP_004025867.1| aspartate 1-decarboxylase [*Caldicellulosiruptor kristjanssonii* 177R1B]
>gi|253577525|ref|ZP_04854838.1| aspartate 1-decarboxylase [*Paenibacillus* sp. oral taxon 786 str. D14]
>gi|304364119|ref|ZP_07361364.1| aspartate 1-decarboxylase [*Actinomyces viscosus* C505]

>gi|70725184|ref|YP_252098.1| aspartate alpha-decarboxylase [*Staphylococcus haemolyticus* JCSC1435]
>gi|238924848|ref|YP_002938364.1| aspartate 1-decarboxylase [*Eubacterium rectale* ATCC 33656]
>gi|167748367|ref|ZP_02420494.1| hypothetical protein ANACAC_03111 [*Anaerostipes caccae* DSM 14662]
>gi|294498158|ref|YP_003561858.1| aspartate 1-decarboxylase [*Bacillus megaterium* QM B1551]
>gi|229172278|ref|ZP_04299842.1| Aspartate 1-decarboxylase alpha chain [*Bacillus cereus* MM3]
>gi|89892958|ref|YP_516445.1| aspartate alpha-decarboxylase [*Desulfitobacterium hafniense* Y51]
>gi|158312064|ref|YP_001504572.1| aspartate alpha-decarboxylase [*Frankia* sp. EAN1 pec]
>gi|303257894|ref|ZP_07343903.1| aspartate 1-decarboxylase [*Burkholderiales bacterium* 1_1_47]
>gi|296131758|ref|YP_003639005.1| aspartate 1-decarboxylase [*Thermincola* sp. JR]
>gi|288817983|ref|YP_003432330.1| aspartate 1-decarboxylase [*Hydrogenobacter thermophilus* TK-6]
>gi|291246356|ref|YP_003505742.1| putative aspartate alpha-decarboxylase PanD [*Staphylococcus simulans* bv. *staphylolyticus*]
>gi|188996356|ref|YP_001930607.1| aspartate 1-decarboxylase [*Sulfurihydrogenibium* sp. YO3AOP1]
>gi|160894028|ref|ZP_02074807.1| hypothetical protein CLOL250_01583 [*Clostridium* sp. L2-50]
>gi|228475771|ref|ZP_04060489.1| aspartate 1-decarboxylase [*Staphylococcus hominis* SK119]
>gi|56963830|ref|YP_175561.1| aspartate alpha-decarboxylase [*Bacillus clausii* KSM-K16]
>gi|82548277|gb|ABB82968.1| putative aspartate decarboxylase [uncultured organism HF70_19B12]
>gi|148244908|ref|YP_001219602.1| aspartate alpha-decarboxylase [*Candidatus Vesicomyosocius okutanii* HA]
>gi|153855966|ref|ZP_01996907.1| hypothetical protein DORLON_02932 [*Dorea longicatena* DSM 13814]
>gi|226947534|ref|YP_002802625.1| aspartate 1-decarboxylase [*Clostridium botulinum* A2 str. Kyoto]
>gi|297568701|ref|YP_003690045.1| aspartate 1-decarboxylase [*Desulfurivibrio alkaliphilus* AHT2]
>gi|289548459|ref|YP_003473447.1| aspartate 1-decarboxylase [*Thermocrinis albus* DSM 14484]
>gi|225180974|ref|YP_03734422.1| aspartate 1-decarboxylase [*Dethiobacter alkaliphilus* AHT 1]
>gi|117165150|emb|CAJ88706.1| putative L-aspartate-alpha-decarboxylase [*Streptomyces ambofaciens* ATCC 23877]
>gi|317123772|ref|YP_004097884.1| L-aspartate 1-decarboxylase [*Intrasporangium calvum* DSM 43043]
>gi|294055934|ref|YP_003549592.1| aspartate 1-decarboxylase [*Coraliomargarita akajimensis* DSM 45221]
>gi|15614252|ref|NP_242555.1| aspartate alpha-decarboxylase [*Bacillus halodurans* C-125]
>gi|297560480|ref|YP_003679454.1| aspartate 1-decarboxylase [*Nocardiopsis dassonvillei* subsp. *dassonvillei* DSM 43111]
>gi|295094090|emb|CBK83181.1| L-aspartate 1-decarboxylase [*Coprococcus* sp. ART55/1]
>gi|312197107|ref|YP_004017168.1| aspartate 1-decarboxylase [*Frankia* sp. Eul1c]
>gi|302038222|ref|YP_003798544.1| aspartate 1-decarboxylase [*Candidatus Nitrospira defluvii*]
>gi|294640899|ref|ZP_06718851.1| aspartate 1-decarboxylase [*Ruminococcus albus* 8]
>gi|227548075|ref|ZP_03978124.1| aspartate alpha-decarboxylase [*Corynebacterium lipophiloflavum* DSM 44291]

>gi|314934646|ref|ZP_07842005.1| aspartate 1-decarboxylase [*Staphylococcus caprae* C87]
>gi|258405137|ref|YP_003197879.1| aspartate 1-decarboxylase [*Desulfohalobium retbaense* DSM 5692]
>gi|302538161|ref|ZP_07290503.1| aspartate 1-decarboxylase [*Streptomyces* sp. C]
>gi|87308237|ref|ZP_01090378.1| aspartate 1-decarboxylase precursor [*Blastopirellula marina* DSM 3645]
>gi|269797992|ref|YP_003311892.1| aspartate 1-decarboxylase [*Veillonella parvula* DSM 2008]
>gi|21673091|ref|NP_661156.1| aspartate alpha-decarboxylase [*Chlorobium tepidum* TLS]
>gi|225851045|ref|YP_002731279.1| aspartate alpha-decarboxylase [*Persephonella marina* EX-H1]
>gi|119356218|ref|YP_910862.1| aspartate alpha-decarboxylase [*Chlorobium phaeobacteroides* DSM 266]
>gi|323141842|ref|ZP_08076706.1| aspartate 1-decarboxylase [*Phascolarctobacterium* sp. YIT 12067]
>gi|15605956|ref|NP_213333.1| aspartate alpha-decarboxylase [*Aquifex aeolicus* VF5]
>gi|317052380|ref|YP_004113496.1| aspartate 1-decarboxylase [*Desulfurispirillum indicum* S5]
>gi|163782147|ref|ZP_02177146.1| aspartate 1-decarboxylase precursor [*Hydrogenivirga* sp. 128-5-R1-1]
>gi|125973417|ref|YP_001037327.1| aspartate alpha-decarboxylase [*Clostridium thermocellum* ATCC 27405]
>gi|315647107|ref|ZP_07900220.1| aspartate 1-decarboxylase [*Paenibacillus vortex* V453]
>gi|152993855|ref|YP_001359576.1| aspartate decarboxylase [*Sulfurovum* sp. NBC37-1]
>gi|16803939|ref|NP_465424.1| aspartate alpha-decarboxylase [*Listeria monocytogenes* EGD-e]
>gi|29833787|ref|NP_828421.1| aspartate alpha-decarboxylase [*Streptomyces avermitilis* MA-4680]
>gi|167629397|ref|YP_001679896.1| aspartate 1-decarboxylase [*Heliobacterium modesticaldum* Ice1]
>gi|157692740|ref|YP_001487202.1| aspartate alpha-decarboxylase [*Bacillus pumilus* SAFR-032]
>gi|258513596|ref|YP_003189818.1| aspartate 1-decarboxylase [*Desulfotomaculum acetoxidans* DSM 771]
>gi|320105461|ref|YP_004181051.1| aspartate 1-decarboxylase [*Terriglobus saanensis* SP1PR4]
>gi|238019295|ref|ZP_04599721.1| hypothetical protein VEIDISOL_01159 [*Veillonella dispar* ATCC 17748]
>gi|261406085|ref|YP_003242326.1| aspartate 1-decarboxylase [*Paenibacillus* sp. Y412MC10]
>gi|323703659|ref|ZP_08115301.1| aspartate 1-decarboxylase [*Desulfotomaculum nigrificans* DSM 574]
>gi|254389556|ref|ZP_05004782.1| aspartate 1-decarboxylase [*Streptomyces clavuligerus* ATCC 27064]
>gi|163813891|ref|ZP_02205285.1| hypothetical protein COPEUT_00044 [*Coprococcus eutactus* ATCC 27759]
>gi|118473676|ref|YP_884441.1| aspartate alpha-decarboxylase [*Mycobacterium smegmatis* str. MC2 155]
>gi|242243653|ref|ZP_04798097.1| aspartate alpha-decarboxylase [*Staphylococcus epidermidis* W23144]
>gi|295840549|ref|ZP_06827482.1| aspartate 1-decarboxylase [*Streptomyces* sp. SPB74]
>gi|229084647|ref|ZP_04216915.1| Aspartate 1-decarboxylase alpha chain [*Bacillus cereus* Rock3-44]
>gi|193213421|ref|YP_001999374.1| aspartate alpha-decarboxylase [*Chlorobaculum parvum* NCIB 8327]
>gi|78189411|ref|YP_379749.1| aspartate alpha-decarboxylase [*Chlorobium chlorochromatii* CaD3]
>gi|262203861|ref|YP_003275069.1| aspartate 1-decarboxylase [*Gordonia bronchialis* DSM 43247]
>gi|57237347|ref|YP_178360.1| aspartate alpha-decarboxylase [*Campylobacter jejuni* RM1221]
>gi|110597596|ref|ZP_01385881.1| aspartate 1-decarboxylase [*Chlorobium ferrooxidans* DSM 13031]
>gi|224477558|ref|YP_002635164.1| putative aspartate 1-decarboxylase [*Staphylococcus carnosus* subsp. *carnosus* TM300]
>gi|311900398|dbj|BAJ32806.1| putative L-aspartate 1-decarboxylase [*Kitasatospora setae* KM-6054]
>gi|228472221|ref|ZP_04056987.1| aspartate 1-decarboxylase [*Capnocytophaga gingivalis* ATCC 33624]
>gi|212696954|ref|ZP_03305082.1| hypothetical protein ANHYDRO_01517 [*Anaerococcus hydrogenalis* DSM 7454]
>gi|152975064|ref|YP_001374581.1| aspartate alpha-decarboxylase [*Bacillus cereus* subsp. *cytotoxis* NVH 391-98]
>gi|311030322|ref|ZP_07708412.1| aspartate alpha-decarboxylase [*Bacillus* sp. m3-13]
>gi|23099218|ref|NP_692684.1| aspartate alpha-decarboxylase [*Oceanobacillus iheyensis* HTE831]
>gi|183983171|ref|YP_001851462.1| aspartate 1-decarboxylase precursor PanD_2 [*Mycobacterium marinum* M]
>gi|306820308|ref|ZP_07453947.1| aspartate 1-decarboxylase [*Eubacterium yurii* subsp. *margaretiae* ATCC 43715]
>gi|312621811|ref|YP_004023424.1| aspartate 1-decarboxylase [*Caldicellulosiruptor kronotskyensis* 2002]
>gi|239927316|ref|ZP_04684269.1| aspartate alpha-decarboxylase [*Streptomyces ghanaensis* ATCC 14672]
>gi|295696300|ref|YP_003589538.1| aspartate 1-decarboxylase [*Bacillus tusciae* DSM 2912]
>gi|303238877|ref|ZP_07325408.1| aspartate 1-decarboxylase [*Acetivibrio cellulolyticus* CD2]
>gi|289435249|ref|YP_003465121.1| hypothetical protein Ise_1886 [*Listeria seeligeri* serovar 1/2b str. SLCC3954]
>gi|302555661|ref|ZP_07308003.1| aspartate 1-decarboxylase [*Streptomyces viridochromogenes* DSM 40736]
>gi|297584390|ref|YP_003700170.1| aspartate 1-decarboxylase [*Bacillus selenitireducens* MLS10]
>gi|291532722|emb|CBL05835.1| L-aspartate 1-decarboxylase [*Megamonas hypermegale* ART12/1]
>gi|167041215|gb|ABZ05972.1| putative aspartate decarboxylase [uncultured marine microorganism HF4000_001N02]
>gi|168181292|ref|ZP_02615956.1| aspartate 1-decarboxylase [*Clostridium botulinum* Bf]
>gi|134298040|ref|YP_001111536.1| aspartate 1-decarboxylase [*Desulfotomaculum reducens* MI-1]
>gi|124514996|gb|EAY56507.1| Aspartate 1-decarboxylase [*Leptospirillum rubarum*]
>gi|195953149|ref|YP_002121439.1| aspartate 1-decarboxylase [*Hydrogenobaculum* sp. Y04AAS1]
>gi|229102244|ref|ZP_04232953.1| Aspartate 1-decarboxylase alpha chain [*Bacillus cereus* Rock3-28]
>gi|319955894|ref|YP_004167157.1| l-aspartate 1-decarboxylase [*Nitratifractor salsuginis* DSM 16511]
>gi|227819486|ref|YP_002823457.1| aspartate alpha-decarboxylase [*Sinorhizobium fredii* NGR234]
>gi|134299644|ref|YP_001113140.1| aspartate 1-decarboxylase [*Desulfotomaculum reducens* MI-1]
>gi|78187623|ref|YP_375666.1| aspartate alpha-decarboxylase [*Chlorobium luteolum* DSM 273]
>gi|294632508|ref|ZP_06711068.1| aspartate 1-decarboxylase [*Streptomyces* sp. e14]
>gi|218246666|ref|YP_002372037.1| aspartate 1-decarboxylase [*Cyanothece* sp. PCC 8801]

>gi|153954248|ref|YP_001395013.1| aspartate alpha-decarboxylase [*Clostridium kluyveri* DSM 555]
>gi|240145726|ref|ZP_04744327.1| aspartate 1-decarboxylase [*Roseburia intestinalis* L1-82]
>gi|187777515|ref|ZP_02993988.1| hypothetical protein CLOSPO_01106 [*Clostridium sporogenes* ATCC 15579]
>gi|189345854|ref|YP_001942383.1| aspartate 1-decarboxylase [*Chlorobium limicola* DSM 245]
>gi|225849174|ref|YP_002729338.1| aspartate alpha-decarboxylase [*Sulfurihydrogenibium azorense* Az-Fu1]
>gi|42524914|ref|NP_970294.1| aspartate alpha-decarboxylase [*Bdellovibrio bacteriovorus* HD100]
>gi|296124338|ref|YP_003632116.1| aspartate 1-decarboxylase [*Planctomyces limnophilus* DSM 3776]
>gi|260592486|ref|ZP_05857944.1| aspartate 1-decarboxylase [*Prevotella veroralis* F0319]
>gi|224373697|ref|YP_002608069.1| aspartate alpha-decarboxylase [*Nautilia profundicola* AmH]
>gi|290955740|ref|YP_003486922.1| L-aspartate-alpha-decarboxylase [*Streptomyces scabiei* 87.22]
>gi|169830320|ref|YP_001716302.1| aspartate 1-decarboxylase [*Candidatus Desulforudis audaxviator* MP104C]
>gi|154246282|ref|YP_001417240.1| aspartate alpha-decarboxylase [*Xanthobacter autotrophics* Py2]
>gi|194335559|ref|YP_002017353.1| aspartate 1-decarboxylase [*Pelodictyon phaeoclathratiforme* BU-1]
>gi|315187531|gb|EFU21287.1| L-aspartate 1-decarboxylase [*Spirochaeta thermophila* DSM 6578]
>gi|145220354|ref|YP_001131063.1| aspartate alpha-decarboxylase [*Prosthecochloris vibrioformis* DSM 265]
>gi|206890877|ref|YP_002249664.1| aspartate 1-decarboxylase [*Thermodesulfovibrio yellowstonii* DSM 11347]
>gi|315303837|ref|ZP_07874325.1| aspartate 1-decarboxylase [*Listeria ivanovii* FSL F6-596]
>gi|257065635|ref|YP_003151891.1| aspartate 1-decarboxylase [*Anaerococcus prevotii* DSM 20548]
>gi|299821666|ref|ZP_07053554.1| aspartate 1-decarboxylase [*Listeria grayi* DSM 20601]
>gi|254458768|ref|ZP_05072192.1| aspartate 1-decarboxylase [*Campylobacterales bacterium* GD 1]
>gi|209526587|ref|ZP_03275112.1| aspartate 1-decarboxylase [*Arthrospira maxima* CS-328]
>gi|242310629|ref|ZP_04809784.1| aspartate 1-decarboxylase [*Helicobacter pullorum* MIT 98-5489]
>gi|260888452|ref|ZP_05899715.1| aspartate 1-decarboxylase [*Selenomonas sputigena* ATCC 35185]
>gi|116747816|ref|YP_844503.1| aspartate 1-decarboxylase [*Syntrophobacter fumaroxidans* MPOB]
>gi|149195160|ref|ZP_01872251.1| aspartate alpha-decarboxylase [*Caminibacter mediatlanticus* TB-2]
>gi|237750942|ref|ZP_04581422.1| aspartate alpha-decarboxylase [*Helicobacter bilis* ATCC 43879]
>gi|189499388|ref|YP_001958858.1| aspartate alpha-decarboxylase [*Chlorobium phaeobacteroides* BS1]
>gi|313142475|ref|ZP_07804668.1| aspartate 1-decarboxylase [*Helicobacter canadensis* MIT 98-5491]
>gi|78776535|ref|YP_392850.1| aspartate alpha-decarboxylase [*Sulfurimonas denitrificans* DSM 1251]
>gi|312879261|ref|ZP_07739061.1| L-aspartate 1-decarboxylase [*Aminomonas paucivorans* DSM 12260]
>gi|313683409|ref|YP_004061147.1| l-aspartate 1-decarboxylase [*Sulfuricurvum kujiense* DSM 16994]
>gi|290968108|ref|ZP_06559653.1| aspartate 1-decarboxylase [*Megasphaera genomosp.* type_1 str. 28L]
>gi|94269421|ref|ZP_01291457.1| Aspartate 1-decarboxylase [delta *proteobacterium* MLMS-1]
>gi|34557994|ref|NP_907809.1| aspartate alpha-decarboxylase [*Wolinella succinogenes* DSM 1740]
>gi|83589014|ref|YP_429023.1| aspartate alpha-decarboxylase [*Moorella thermoacetica* ATCC 39073]
>gi|288904380|ref|YP_003429601.1| aspartate 1-decarboxylase [*Streptococcus gallolyticus* UCN34]
>gi|256546079|ref|ZP_05473432.1| aspartate 1-decarboxylase [*Anaerococcus vaginalis* ATCC 51170]
>gi|84687580|ref|ZP_01015455.1| aspartate 1-decarboxylase precursor [*Maritimibacter alkaliphilus* HTCC2654]
>gi|319440712|ref|ZP_07989868.1| aspartate alpha-decarboxylase [*Corynebacterium variabile* DSM 44702]
>gi|152990004|ref|YP_001355726.1| aspartate alpha-decarboxylase [*Nitratiruptor* sp. SB155-2]
>gi|196229549|ref|ZP_03128414.1| aspartate 1-decarboxylase [*Chthoniobacter flavus* Ellin428]
>gi|310778937|ref|YP_003967270.1| L-aspartate 1-decarboxylase [*Ilyobacter polytropus* DSM 2926]
>gi|194333223|ref|YP_002015083.1| aspartate alpha-decarboxylase [*Prosthecochloris aestuarii* DSM 271]
>gi|307720220|ref|YP_003891360.1| L-aspartate 1-decarboxylase [*Sulfurimonas autotrophica* DSM 16294]
>gi|317057177|ref|YP_004105644.1| aspartate 1-decarboxylase [*Ruminococcus albus* 7]
>gi|281358405|ref|ZP_06244887.1| aspartate 1-decarboxylase [*Victivallis vadensis* ATCC BAA-548]
>gi|13474851|ref|NP_106421.1| aspartate alpha-decarboxylase [*Mesorhizobium loti* MAFF303099]
>gi|270308113|ref|YP_003330171.1| aspartate 1-decarboxylase [*Dehalococcoides* sp. VS]
>gi|324963812|gb|ADY54591.1| L-aspartate 1-decarboxylase [*Syntrophobotulus glycolicus* DSM 8271]
>gi|13488064|ref|NP_085658.1| aspartate alpha-decarboxylase [*Mesorhizobium loti* MAFF303099]
>gi|315638262|ref|ZP_07893443.1| aspartate 1-decarboxylase [*Campylobacter upsaliensis* JV21]
>gi|171778858|ref|ZP_02919920.1| hypothetical protein STRINF_00779 [*Streptococcus infantarius* subsp. *infantarius* ATCC BAA-102]
>gi|17231061|ref|NP_487609.1| aspartate alpha-decarboxylase [*Nostoc* sp. PCC 7120]
>gi|317121598|ref|YP_004101601.1| L-aspartate 1-decarboxylase [*Thermaerobacter marianensis* DSM 12885]
>gi|225163545|ref|ZP_03725856.1| Aspartate 1-decarboxylase [*Opitutaceae bacterium* TAV2]
>gi|224437987|ref|ZP_03658926.1| aspartate alpha-decarboxylase [*Helicobacter cinaedi* CCUG 18818]
>gi|237752532|ref|ZP_04583012.1| aspartate alpha-decarboxylase [*Helicobacter winghamensis* ATCC BAA-430]
>gi|157736689|ref|YP_001489372.1| aspartate alpha-decarboxylase [*Arcobacter butzleri* RM4018]
>gi|317152682|ref|YP_004120730.1| aspartate 1-decarboxylase [*Desulfovibrio aespoeensis* Aspo-2]
>gi|298491519|ref|YP_003721696.1| aspartate 1-decarboxylase ['*Nostoc azollae*' 0708]
>gi|268680556|ref|YP_003304987.1| aspartate 1-decarboxylase [*Sulfurospirillum deleyianum* DSM 6946]
>gi|269792079|ref|YP_003316983.1| aspartate 1-decarboxylase [*Thermanaerovibrio acidaminovorans* DSM 6589]
>gi|158335510|ref|YP_001516682.1| aspartate alpha-decarboxylase [*Acaryochloris marina* MBIC11017]
>gi|91204562|emb|CAJ70790.1| strongly similar to aspartate 1-decarboxylase precursor (aspartate alpha-decarboxylase) [*Candidatus Kuenenia stuttgartiensis*]
>gi|288573810|ref|ZP_06392167.1| aspartate 1-decarboxylase [*Dethiosulfovibrio peptidovorans* DSM 11002]

>gi|289432636|ref|YP_003462509.1| aspartate 1-decarboxylase [*Dehalococcoides sp. GT*]
>gi|182677509|ref|YP_001831655.1| aspartate alpha-decarboxylase [*Beijerinckia indica* subsp. *indica* ATCC 9039]
>gi|229004643|ref|ZP_04162381.1| aspartate alpha-decarboxylase [*Bacillus mycoides* Rock1-4]
>gi|119512431|ref|ZP_01631513.1| aspartate 1-decarboxylase precursor [*Nodularia spumigena* CCY9414]
>gi|269839249|ref|YP_003323941.1| aspartate 1-decarboxylase [*Thermobaculum terrenum* ATCC BAA-798]
>gi|186682855|ref|YP_001866051.1| aspartate alpha-decarboxylase [*Nostoc punctiforme* PCC 73102]
>gi|258511926|ref|YP_003185360.1| aspartate 1-decarboxylase [*Alicyclobacillus acidocaldarius* subsp. *acidocaldarius* DSM 446]
>gi|218288596|ref|ZP_03492873.1| aspartate 1-decarboxylase [*Alicyclobacillus acidocaldarius* LAA1]
>gi|282896795|ref|ZP_06304801.1| Aspartate decarboxylase [*Raphidiopsis brookii* D9]
>gi|206896045|ref|YP_002246959.1| aspartate 1-decarboxylase [*Coprothermobacter proteolyticus* DSM 5265]
>gi|320012833|gb|ADW07683.1| aspartate 1-decarboxylase [*Streptomyces flavogriseus* ATCC 33331]
>gi|323700614|ref|ZP_08112526.1| aspartate 1-decarboxylase [*Desulfovibrio sp.* ND132]
>gi|37523797|ref|NP_927174.1| aspartate alpha-decarboxylase [*Gloeobacter violaceus* PCC 7421]
>gi|296272234|ref|YP_003654865.1| aspartate 1-decarboxylase [*Arcobacter nitrofigilis* DSM 7299]
>gi|119872877|ref|YP_930884.1| aspartate 1-decarboxylase [*Pyrobaculum islandicum* DSM 4184]
>gi|226312675|ref|YP_002772569.1| aspartate 1-decarboxylase precursor [*Brevibacillus brevis* NBRC 100599]
>gi|282900379|ref|ZP_06308329.1| Aspartate decarboxylase [*Cylindrospermopsis raciborskii* CS-505]
>gi|307151736|ref|YP_003887120.1| aspartate 1-decarboxylase [*Cyanothece sp.* PCC 7822]
>gi|222100611|ref|YP_002535179.1| Aspartate 1-decarboxylase precursor [*Thermotoga neapolitana* DSM 4359]
>gi|320102432|ref|YP_004178023.1| L-aspartate 1-decarboxylase [*Isosphaera pallida* ATCC 43644]
>gi|322378504|ref|ZP_08052954.1| Aspartate 1-decarboxylase precursor [*Helicobacter suis* HS1]
>gi|217076689|ref|YP_002334405.1| aspartate alpha-decarboxylase [*Thermosipho africanus* TCF52B]
>gi|315497331|ref|YP_004086135.1| aspartate 1-decarboxylase [*Asticcacaulis excentricus* CB 48]
>gi|166366461|ref|YP_001658734.1| aspartate alpha-decarboxylase [*Microcystis aeruginosa* NIES-843]
>gi|220904255|ref|YP_002479567.1| Aspartate 1-decarboxylase [*Desulfovibrio desulfuricans* subsp. *desulfuricans* str. ATCC 27774]
>gi|57339838|gb|AAW49906.1| hypothetical protein FTT1391 [synthetic construct]
>gi|16331671|ref|NP_442399.1| aspartate alpha-decarboxylase [*Synechocystis sp.* PCC 6803]
>gi|303327013|ref|ZP_07357455.1| aspartate 1-decarboxylase [*Desulfovibrio sp.* 3_1_syn3]
>gi|67460926|sp|Q7VJB2.2|PAND_HELHP RecName: Full=Aspartate 1-decarboxylase;

What is claimed is:

1. A recombinant bacterial strain of the genus Zymomonas comprising a heterologous nucleic acid molecule encoding a polypeptide having 2-dehydropantoate reductase activity and a heterologous nucleic acid molecule encoding a polypeptide having aspartate 1-decarboxylase activity wherein said recombinant bacterial strain can produce ethanol in the absence of externally supplied pantothenic acid.

2. A recombinant bacterial strain of claim 1 wherein the polypeptide having 2-dehydropantoate reductase activity is an enzyme belonging to the EC 1.1.1.169 class.

3. A recombinant bacterial strain of claim 2 wherein the polypeptide having 2-dehydropantoate reductase activity has at least ten conserved amino acid positions selected from the group consisting of G at position 7, G at position 9, G at position 12, K at position 72, N at position 98, G at position 99, K at position 176, N at position 180, N at position 184, E at position 210, S at position 244, D or S at position 248, and E at position 256, as compared to the E. coli 2-dehydropantoate reductase of SEQ ID NO:4.

4. A recombinant bacterial strain of claim 1 wherein the polypeptide having aspartate 1-decarboxylase activity is an enzyme belonging to the EC 4.1.1.11 class.

5. A recombinant bacterial strain of claim 4 wherein the polypeptide having aspartate 1-decarboxylase activity has at least eight conserved amino acid positions selected from the group consisting of K at position 9, H at position 11, Y at position 22, G at position 24, S at position 25, G at position 52, R at position 54, T at position 57, Y at position 58, N at position 72, G at position 73, and I at position 86, as compared to the E. coli aspartate 1-decarboxylase of SEQ ID NO:7.

6. A recombinant bacterial strain of claim 4 wherein the polypeptide having aspartate 1-decarboxylase activity has the five conserved amino acid positions K at position 9, Y at position 22, G at position 24, T at position 57, and Y at position 58, as compared to the E. coli aspartate 1-decarboxylase of SEQ ID NO:7.

7. A recombinant bacterial strain of claim 1 wherein the strain grows in media that lacks pantothenic acid.

8. The recombinant bacterial strain of claim 1 wherein the strain comprises genetic modifications which enhance the production of ethanol.

9. A process for producing a Zymomonas strain that synthesizes pantothenic acid comprising:
a) providing a bacterial strain of the genus Zymomonas;
b) introducing a heterologous nucleic acid molecule encoding a polypeptide having 2-dehydropantoate reductase activity; and
c) introducing a heterologous nucleic acid molecule encoding a polypeptide having aspartate 1-decarboxylase activity;

wherein steps b) and c) may be in either order or simultaneous, and wherein 2-dehydropantoate reductase activity and aspartate 1-decarboxylase activity are both expressed in the strain produced by steps (a), (b), and (c).

10. A method for the producing ethanol comprising:
a) providing a recombinant bacterial strain of the genus Zymomonas comprising a heterologous nucleic acid molecule encoding a polypeptide having 2-dehydropantoate reductase activity and a heterologous nucleic acid molecule encoding a polypeptide having aspartate 1-decarboxylase activity; and
b) contacting the strain of (a) with fermentation medium under conditions whereby the strain produces ethanol.

11. A method according to claim 10 wherein the polypeptide having 2-dehydropantoate reductase activity is an enzyme belonging to the EC 1.1.1.169 class.

12. A method according to claim 11 wherein the polypeptide having 2-dehydropantoate reductase activity has at least ten conserved amino acid positions selected from the group consisting of G at position 7, G at position 9, G at position 12, K at position 72, N at position 98, G at position 99, K at position 176, N at position 180, N at position 184, E at position 210, S at position 244, D or S at position 248, and E at position 256, as compared to the E. coli 2-dehydropantoate reductase of SEQ ID NO:4.

13. A method according to claim 10 wherein the polypeptide having aspartate 1-decarboxylase activity is an enzyme belonging to the EC 4.1.1.11 class.

14. A method according to claim 13 wherein the polypeptide having aspartate 1-decarboxylase activity has at least eight conserved amino acid positions selected from the group consisting of K at position 9, H at position 11, Y at position 22, G at position 24, S at position 25, G at position 52, R at position 54, T at position 57, Y at position 58, N at position 72, G at position 73, and I at position 86, as compared to the E. coli aspartate 1-decarboxylase of SEQ ID NO:7.

15. A method according to claim 13 wherein the polypeptide having aspartate 1-decarboxylase activity has the five conserved amino acid positions K at position 9, Y at position 22, G at position 24, T at position 57, and Y at position 58, as compared to the E. coli aspartate 1-decarboxylase of SEQ ID NO:7.

16. A method according to claim 10 wherein prior to step (b) the bacterial strain of (a) is contacted with medium that lacks or has a sub-optimal amount of pantothenic acid wherein a seed culture is produced to inoculate the fermentation medium of (b).

17. A method according to claim 10 or 16 wherein the fermentation medium lacks or has a sub-optimal amount of pantothenic acid.

* * * * *

```
                        SEQUENCE LISTING

<160> NUMBER OF SEQ ID NOS: 19

<210> SEQ ID NO 1
<211> LENGTH: 1620
<212> TYPE: DNA
<213> ORGANISM: artificial sequence
<220> FEATURE:
<223> OTHER INFORMATION: synthetic operon with GI promoter, E. coli panE
      and panD codign regions

<400> SEQUENCE: 1
tcactcatcc atggggccgg ccactagtcg atctgtgctg tttgccacgg tatgcagcac      60
cagcgcgaga ttatgggctc gcacgctcga ctgtcggacg ggggcactgg aacgagaagt     120
caggcgagcc gtcacgccct tgacaatgcc acatcctgag caaataattc aaccactaaa     180
caaatcaacc gcgtttcccg gaggtaacca tgaaaattac cgtattggga tgcggtgcct     240
tagggcaatt atggcttaca gcactttgca aacagggtca tgaagttcag ggctggctgc     300
gcgtaccgca accttattgt agcgtgaatc tggttgagac agatggttcg atatttaacg     360
aatcgctgac cgccaacgat cccgattttc tcgccaccag cgatctgctc ctggtgacgc     420
tgaaagcatg gcaggtttcc gatgccgtca aaagcctcgc gtccacactg cctgtaacta     480
cgccaatact gttaattcac aacggcatgg gcaccatcga agagttgcaa acattcagc     540 agccattact gatgggcacc accacccatg cagcccgccg cgacggcaat gtcattattc     600
atgtggcaaa cggtatcacg catattggcc cggcacggca acaggacggg gattacagtt     660
atctggcgga tattttgcaa accgtgttgc tgacgttgc ctggcataac aatattcgcg     720
ccgagctgtg gcgcaagctg gcagtcaact gcgtgattaa tccactgact gccatctgga     780
attgcccgaa cggtgaatta cgtcatcatc cgcaagaaat tatgcagata tgcgaagaag     840
```

```
tcgcggcggt gatcgaacgc gaagggcatc atacttcagc agaagatttg cgtgattacg    900
tgatgcaggt gattgatgcc acagcggaaa atatctcgtc gatgttgcag gatatccgcg    960
cgctgcgcca cactgaaatc gactatatca atggttttct cttacgccgc gcccgcgcgc   1020
atgggattgc cgtaccggaa acacccgcc tgtttgaaat ggtaaaaaga aaggagagtg   1080
aatatgagcg catcggcact ggtttgcctc gcccctggta gtaagttagg agaataaaca   1140
tgattcgcac gatgctgcag ggcaaactcc accgcgtgaa agtgactcat gcggacctgc   1200
actatgaagg ttcttgcgcc attgaccagg attttcttga cgcagccggt attctcgaaa   1260
acgaagccat tgatatctgg aatgtcacca acggcaagcg tttctccact tatgccatcg   1320
cggcagaacg cggttcgaga attatttctg ttaacggtgc ggcggccac tgcgccagtg   1380 tcggcgatat tgtcatcatc gccagcttcg ttaccatgcc agatgaagaa gctcgcacct   1440
ggcgacccaa cgtcgcctat tttgaaggcg acaatgaaat gaaacgtacc gcgaaagcga   1500
ttccggtaca ggttgcttga gctagcactg tgcagtccgt tggcccggtt atcggtagcg   1560
ataccgggca tttttttaag gaacgatcga tagcggccgc cctgcaggaa ttctcttact   1620

<210> SEQ ID NO 2
<211> LENGTH: 187
<212> TYPE: DNA
<213> ORGANISM: Actinoplanes missouriensis

<400> SEQUENCE: 2
actagtcgat ctgtgctgtt tgccacggta tgcagcacca gcgcgagatt atgggctcgc     60
acgctcgact gtcggacggg ggcactggaa cgagaagtca ggcgagccgt cacgcccttg    120
acaatgccac atcctgagca aataattcaa ccactaaaca aatcaaccgc gtttcccgga    180
ggtaacc                                                             187

<210> SEQ ID NO 3
<211> LENGTH: 912
<212> TYPE: DNA
<213> ORGANISM: Escherichia coli

<400> SEQUENCE: 3
atgaaaatta ccgtattggg atgcggtgcc ttagggcaat tatggcttac agcactttgc     60
aaacagggtc atgaagttca gggctggctg cgcgtaccgc aaccttattg tagcgtgaat    120
ctggttgaga cagatggttc gatatttaac gaatcgctga ccgccaacga tcccgatttt    180
ctcgccacca gcgatctgct cctggtgacg ctgaaagcat ggcaggtttc cgatgccgtc    240
aaaagcctcg cgtccacact gcctgtaact acgccaatac tgttaattca aacggcatg    300 ggcaccatcg aagagttgca aaacattcag cagccattac tgatgggcac caccacccat    360
gcagcccgcc gcgacggcaa tgtcattatt catgtggcaa acggtatcac gcatattggc    420
ccggcacggc aacaggacgg ggattacagt tatctggcgg atattttgca aaccgtgttg    480
cctgacgttg cctggcataa caatattcgc gccgagctgt ggcgcaagct ggcagtcaac    540
tgcgtgatta atccactgac tgccatctgg aattgcccga cggtgaatt acgtcatcat    600 ccgcaagaaa ttatgcagat atgcgaagaa gtcgcggcgg tgatcgaacg cgaagggcat    660
catacttcag cagaagattt gcgtgattac gtgatgcagg tgattgatgc cacagcggaa    720
aatatctcgt cgatgttgca ggatatccgc gcgctgcgcc acactgaaat cgactatatc    780
aatggttttc tcttacgccg cgcccgcgcg catgggattg ccgtaccgga aacacccgc    840
```

```
ctgtttgaaa tggtaaaaag aaaggagagt gaatatgagc gcatcggcac tggtttgcct    900 cgccctggt ag                                                         912
```

<210> SEQ ID NO 4
<211> LENGTH: 303
<212> TYPE: PRT
<213> ORGANISM: Escherichia coli

<400> SEQUENCE: 4

```
Met Lys Ile Thr Val Leu Gly Cys Gly Ala Leu Gly Gln Leu Trp Leu
1               5                   10                  15

Thr Ala Leu Cys Lys Gln Gly His Glu Val Gln Gly Trp Leu Arg Val
            20                  25                  30

Pro Gln Pro Tyr Cys Ser Val Asn Leu Val Glu Thr Asp Gly Ser Ile
        35                  40                  45

Phe Asn Glu Ser Leu Thr Ala Asn Asp Pro Asp Phe Leu Ala Thr Ser
    50                  55                  60

Asp Leu Leu Leu Val Thr Leu Lys Ala Trp Gln Val Ser Asp Ala Val
65                  70                  75                  80

Lys Ser Leu Ala Ser Thr Leu Pro Val Thr Thr Pro Ile Leu Leu Ile
                85                  90                  95

His Asn Gly Met Gly Thr Ile Glu Glu Leu Gln Asn Ile Gln Gln Pro
            100                 105                 110

Leu Leu Met Gly Thr Thr Thr His Ala Ala Arg Arg Asp Gly Asn Val
        115                 120                 125

Ile Ile His Val Ala Asn Gly Ile Thr His Ile Gly Pro Ala Arg Gln
    130                 135                 140

Gln Asp Gly Asp Tyr Ser Tyr Leu Ala Asp Ile Leu Gln Thr Val Leu
145                 150                 155                 160

Pro Asp Val Ala Trp His Asn Asn Ile Arg Ala Glu Leu Trp Arg Lys
                165                 170                 175

Leu Ala Val Asn Cys Val Ile Asn Pro Leu Thr Ala Ile Trp Asn Cys
            180                 185                 190

Pro Asn Gly Glu Leu Arg His His Pro Gln Glu Ile Met Gln Ile Cys
        195                 200                 205

Glu Glu Val Ala Ala Val Ile Glu Arg Glu Gly His His Thr Ser Ala
    210                 215                 220

Glu Asp Leu Arg Asp Tyr Val Met Gln Val Ile Asp Ala Thr Ala Glu
225                 230                 235                 240

Asn Ile Ser Ser Met Leu Gln Asp Ile Arg Ala Leu Arg His Thr Glu
                245                 250                 255

Ile Asp Tyr Ile Asn Gly Phe Leu Leu Arg Arg Ala Arg Ala His Gly
            260                 265                 270

Ile Ala Val Pro Glu Asn Thr Arg Leu Phe Glu Met Val Lys Arg Lys
        275                 280                 285

Glu Ser Glu Tyr Glu Arg Ile Gly Thr Gly Leu Pro Arg Pro Trp
    290                 295                 300
```

<210> SEQ ID NO 5
<211> LENGTH: 18
<212> TYPE: DNA
<213> ORGANISM: Zymomonas mobilis

<400> SEQUENCE: 5

```
taagttagga gaataaac                                                   18
```

<210> SEQ ID NO 6
<211> LENGTH: 381
<212> TYPE: DNA
<213> ORGANISM: Escherichia coli

<400> SEQUENCE: 6

```
atgattcgca cgatgctgca gggcaaactc caccgcgtga agtgactca tgcggacctg      60 cactatgaag gttcttgcgc cattgaccag gattttcttg acgcagccgg tattctcgaa     120
aacgaagcca ttgatatctg gaatgtcacc aacggcaagc gtttctccac ttatgccatc     180
gcggcagaac gcggttcgag aattatttct gttaacggtg cggcggccca ctgcgccagt     240
gtcggcgata ttgtcatcat cgccagcttc gttaccatgc cagatgaaga agctcgcacc     300
tggcgaccca acgtcgccta ttttgaaggc gacaatgaaa tgaaacgtac cgcgaaagcg     360
attccggtac aggttgcttg a                                               381
```

<210> SEQ ID NO 7
<211> LENGTH: 126
<212> TYPE: PRT
<213> ORGANISM: Escherichia coli

<400> SEQUENCE: 7

```
Met Ile Arg Thr Met Leu Gln Gly Lys Leu His Arg Val Lys Val Thr
1               5                   10                  15

His Ala Asp Leu His Tyr Glu Gly Ser Cys Ala Ile Asp Gln Asp Phe
            20                  25                  30

Leu Asp Ala Ala Gly Ile Leu Glu Asn Glu Ala Ile Asp Ile Trp Asn
        35                  40                  45

Val Thr Asn Gly Lys Arg Phe Ser Thr Tyr Ala Ile Ala Ala Glu Arg
    50                  55                  60

Gly Ser Arg Ile Ile Ser Val Asn Gly Ala Ala Ala His Cys Ala Ser
65                  70                  75                  80

Val Gly Asp Ile Val Ile Ile Ala Ser Phe Val Thr Met Pro Asp Glu
                85                  90                  95

Glu Ala Arg Thr Trp Arg Pro Asn Val Ala Tyr Phe Glu Gly Asp Asn
            100                 105                 110

Glu Met Lys Arg Thr Ala Lys Ala Ile Pro Val Gln Val Ala
        115                 120                 125
```

<210> SEQ ID NO 8
<211> LENGTH: 35
<212> TYPE: DNA
<213> ORGANISM: Escherichia coli

<400> SEQUENCE: 8

```
gcccggttat cggtagcgat accgggcatt ttttt                                 35
```

<210> SEQ ID NO 9
<211> LENGTH: 312
<212> TYPE: PRT
<213> ORGANISM: Methylococcus capsulatus

<400> SEQUENCE: 9

```
Met Asn Ile Leu Val Ile Gly Thr Gly Ala Ile Gly Ser Phe Tyr Gly
1               5                   10                  15

Ala Leu Leu Ala Lys Thr Gly His Cys Val Ser Val Val Ser Arg Ser
            20                  25                  30

Asp Tyr Glu Thr Val Lys Ala Lys Gly Ile Arg Ile Arg Ser Ala Thr
        35                  40                  45
```

```
Leu Gly Asp Tyr Thr Phe Arg Pro Ala Ala Val Val Arg Ser Ala Ala
 50                  55                  60

Glu Leu Glu Thr Lys Pro Asp Cys Thr Leu Leu Cys Ile Lys Val Val
 65                  70                  75                  80

Glu Gly Ala Asp Arg Val Gly Leu Leu Arg Asp Ala Val Ala Pro Asp
                 85                  90                  95

Thr Gly Ile Val Leu Ile Ser Asn Gly Ile Asp Ile Glu Pro Glu Val
                100                 105                 110

Ala Ala Ala Phe Pro Asp Asn Glu Val Ile Ser Gly Leu Ala Phe Ile
            115                 120                 125

Gly Val Thr Arg Thr Ala Pro Gly Glu Ile Trp His Gln Ala Tyr Gly
130                 135                 140

Arg Leu Met Leu Gly Asn Tyr Pro Gly Gly Val Ser Glu Arg Val Lys
145                 150                 155                 160

Thr Leu Ala Ala Ala Phe Glu Glu Ala Gly Ile Asp Gly Ile Ala Thr
                165                 170                 175

Glu Asn Ile Thr Thr Ala Arg Trp Gln Lys Cys Val Trp Asn Ala Ala
                180                 185                 190

Phe Asn Pro Leu Ser Val Leu Ser Gly Gly Leu Asp Thr Leu Asp Ile
            195                 200                 205

Leu Ser Thr Gln Glu Gly Phe Val Arg Ala Ile Met Gln Glu Ile Arg
210                 215                 220

Ala Val Ala Ala Ala Asn Gly His Pro Leu Pro Glu Asp Ile Val Glu
225                 230                 235                 240

Lys Asn Val Ala Ser Thr Tyr Lys Met Pro Pro Tyr Lys Thr Ser Met
                245                 250                 255

Leu Val Asp Phe Glu Ala Gly Gln Pro Met Glu Thr Glu Val Ile Leu
            260                 265                 270

Gly Asn Ala Val Arg Ala Gly Arg Arg Thr Arg Val Ala Ile Pro His
            275                 280                 285

Leu Glu Ser Val Tyr Ala Leu Met Lys Leu Leu Glu Leu Arg Thr Ser
290                 295                 300

Lys Ser Leu Trp Gly Asn Pro Pro
305                 310

<210> SEQ ID NO 10
<211> LENGTH: 302
<212> TYPE: PRT
<213> ORGANISM: Geobacter metallireducens

<400> SEQUENCE: 10

Met Arg Ile Ala Ile Val Gly Ala Gly Ala Leu Gly Leu Tyr Tyr Gly
1               5                   10                  15

Ala Leu Leu Gln Arg Ser Gly Glu Asp Val His Phe Leu Leu Arg Arg
                20                  25                  30

Asp Tyr Glu Ala Ile Ala Gly Asn Gly Leu Lys Val Phe Ser Ile Asn
            35                  40                  45

Gly Asp Phe Thr Leu Pro His Val Lys Gly Tyr Arg Ala Pro Glu Glu
 50                  55                  60

Ile Gly Pro Met Asp Leu Val Leu Val Gly Leu Lys Thr Phe Ala Asn
 65                  70                  75                  80

Ser Arg Tyr Glu Glu Leu Ile Arg Pro Leu Val Glu Glu Gly Thr Gln
                 85                  90                  95

Ile Leu Thr Leu Gln Asn Gly Leu Gly Asn Glu Glu Ala Leu Ala Thr
                100                 105                 110
```

```
Leu Phe Gly Ala Glu Arg Ile Ile Gly Gly Val Ala Phe Leu Cys Ser
            115                 120                 125

Asn Arg Gly Glu Pro Gly Glu Val His His Leu Gly Ala Gly Arg Ile
130                 135                 140

Ile Leu Gly Glu Phe Leu Pro Arg Asp Thr Gly Arg Ile Glu Glu Leu
145                 150                 155                 160

Ala Ala Met Phe Arg Gln Ala Gly Val Asp Cys Arg Thr Thr Asp Asp
                165                 170                 175

Leu Lys Arg Ala Arg Trp Glu Lys Leu Val Trp Asn Ile Pro Phe Asn
            180                 185                 190

Gly Leu Cys Ala Leu Leu Gln Gln Pro Val Asn Leu Ile Leu Ala Arg
        195                 200                 205

Asp Val Ser Arg Lys Leu Val Arg Gly Ile Met Leu Glu Val Ile Ala
    210                 215                 220

Gly Ala Asn Ala Gln Gly Leu Ala Thr Phe Ile Ala Asp Gly Tyr Val
225                 230                 235                 240

Asp Asp Met Leu Glu Phe Thr Asp Ala Met Gly Glu Tyr Lys Pro Ser
                245                 250                 255

Met Glu Ile Asp Arg Glu Glu Gly Arg Pro Leu Glu Ile Ala Ala Ile
            260                 265                 270

Phe Arg Thr Pro Leu Ala Tyr Gly Ala Arg Glu Gly Ile Ala Met Pro
        275                 280                 285

Arg Val Glu Met Leu Ala Thr Leu Leu Glu Gln Ala Thr Gly
    290                 295                 300

<210> SEQ ID NO 11
<211> LENGTH: 350
<212> TYPE: PRT
<213> ORGANISM: Schizosaccharomyces pombe

<400> SEQUENCE: 11

Met Asn Asn Thr Ile Tyr Ile Leu Gly Ala Gly Ser Ile Gly Ser Leu
1               5                   10                  15

Leu Ala Tyr Glu Leu Ala Ser Leu Lys Ser Ile Asn Asn Arg Val Ile
            20                  25                  30

Leu Leu Leu Arg Asp Lys Ser Arg Val Asn Ser Phe Lys Asp Lys Asn
        35                  40                  45

Ser Thr Leu Lys Ile Asp Arg Leu Phe Glu Glu Asn Val Pro His Leu
    50                  55                  60

Cys Cys Gln Val Thr Ala Ser Glu Pro Ser Gln Leu Asn Val Gln Ser
65                  70                  75                  80

Ile Glu Asn Met Ile Val Thr Lys Ala Gly Gln Thr Glu Asn Ala
                85                  90                  95

Leu Ser Lys Tyr Leu Pro Tyr Leu Ser Lys Asn Ser Asn Ile Leu Phe
            100                 105                 110

Val Gln Asn Gly Met Gly Ala Val Glu Asn Val Cys Gly Lys Leu Trp
        115                 120                 125

Pro Glu Glu Gln Asn Lys Pro Ser Ile Tyr Gln Gly Val Ile Ser His
    130                 135                 140

Gly Cys Phe Gln Thr Ala Pro Phe His Phe Ser His Ala Gly Leu Gly
145                 150                 155                 160

Asp Leu Lys Ile Ser Lys Val Pro Lys Asn Pro Lys Lys Ile Leu Pro
                165                 170                 175

Asp Glu Ala Ala Glu Thr Pro Cys Glu Met Ile Lys Ser Leu Gly Lys
            180                 185                 190
```

Ser Glu Leu Leu Arg Leu Arg Tyr Met Asn Tyr Pro Glu Leu Leu Val
            195                 200                 205

Asn Gln Cys Glu Lys Leu Val Ile Asn Ala Cys Ile Asn Pro Thr Thr
210                 215                 220

Ala Thr Leu Asp Cys Val Asn Gly Glu Leu Tyr Asn Asp Glu Ser Ala
225                 230                 235                 240

Lys Glu Leu Phe Arg Cys Ile Ile Lys Glu Cys Val Asp Ile Phe Phe
            245                 250                 255

Lys Cys Ile Pro Leu Phe Lys Asn Glu Glu Ala Glu Lys Ile Leu
                260                 265                 270

Asn Val Asn Arg Leu Leu Asp Arg Val Met Phe Val Gly Thr Lys Val
            275                 280                 285

Asn Gly Ala Asn Ser Ser Ser Thr Arg Gln Asp Cys Leu Leu Leu Arg
290                 295                 300

Glu Thr Glu Ile Asp Ala Ile Asn Gly Tyr Val Val Lys Leu Ala Glu
305                 310                 315                 320

Asn Asn Gly Phe Gln Ala Thr Val Asn Lys Thr Met Met Leu Leu Thr
            325                 330                 335

Lys Ser Arg Leu Gly Leu Asn Arg Cys Arg Ala His Ala Arg
            340                 345                 350

<210> SEQ ID NO 12
<211> LENGTH: 379
<212> TYPE: PRT
<213> ORGANISM: Saccharomyces cerevisiae

<400> SEQUENCE: 12

Met Thr Ala Pro His Arg Ser Thr Ile His Ile Leu Gly Leu Gly Ala
1               5                   10                  15

Met Gly Thr Val Leu Ala Val Asp Leu Leu Arg Phe Thr Asn Ala Leu
            20                  25                  30

Val Val Pro Leu Phe Arg Ser Gln Glu Arg Leu Ala Gln Phe Gln Lys
        35                  40                  45

Thr Asn Gly Asn Asn Ile Ser Ile Arg Lys Leu Tyr Leu Glu Gly Ser
    50                  55                  60

Pro Ile Phe Ser Tyr Pro Val Glu Lys Cys Glu Cys Pro Glu Thr Phe
65                  70                  75                  80

Ser Lys Lys Pro Ile Asp Asn Leu Val Val Thr Thr Lys Thr Tyr Gln
                85                  90                  95

Thr Lys Glu Ala Leu Ala Pro Tyr Leu Pro Tyr Ile Asn Lys Asn Thr
            100                 105                 110

Asn Leu Ile Leu Ile Gln Asn Gly Leu Gly Val Leu Glu Leu Leu Arg
        115                 120                 125

Glu Glu Ile Phe Thr Asp Ser Lys Asn Arg Pro His Leu Phe Gln Gly
130                 135                 140

Val Ile Ser His Gly Val Tyr Gln Asp Lys Ala Gly Val Phe Asn His
145                 150                 155                 160

Ala Gly Trp Ala Gly Met Lys Ile Ala Lys Leu Pro Trp Thr Glu Glu
                165                 170                 175

Glu Met Ile Gln Lys Lys Ser Val Glu Asp Asp Ala Ala Asn Asn
            180                 185                 190

Ser Leu Val Lys Leu Leu Thr Glu Pro Lys Phe Ala Lys Glu Phe Gly
        195                 200                 205

Ile Glu His Ser Thr Tyr Gln Glu Met Leu Phe Gly Gln Leu Phe Lys
210                 215                 220

```
Phe Leu Val Asn Ala Cys Met Asn Pro Val Thr Ala Ile Leu Asp Cys
225                 230                 235                 240

Val Asn Gly Glu Met Lys Ala Ser Cys Gly Pro Val Phe Thr Ser Ile
            245                 250                 255

Ile Asp Glu Cys Leu Gln Ile Leu Arg Val Ala Tyr Arg Pro Leu Phe
            260                 265                 270

Gln Tyr His Glu Lys Tyr Ser Gly Asn Glu Glu Tyr Pro Glu Met Asp
            275                 280                 285

Val Asn Ala Val Leu Thr Thr Asp Asn Met Val Ser Glu Val Thr Arg
            290                 295                 300

Ile Gly Cys Asp Ile Asn Ser Arg Asn Ser Ser Met Arg Gln Asp
305                 310                 315                 320

Thr Leu Phe Leu Arg Asp Ile Glu Ile Glu Tyr Ile Asn Gly Tyr Val
                325                 330                 335

Val Lys Leu Ala Asp Asn Leu Asn Leu Asp Pro Asn Cys Cys Lys Val
                340                 345                 350

Asn Lys Thr Ile Gly Glu Leu Ala Thr Met Arg Leu Ala Leu Asn Arg
            355                 360                 365

Ser Arg Ser Ile Asn Gly Asp Trp Arg Lys Asp
            370                 375
```

<210> SEQ ID NO 13
<211> LENGTH: 299
<212> TYPE: PRT
<213> ORGANISM: Ralstonia eutropha

<400> SEQUENCE: 13

```
Met Lys Val Ala Ile Met Gly Ala Gly Ala Val Gly Cys Tyr Tyr Gly
1               5                   10                  15

Gly Met Leu Ala Arg Ala Gly His Glu Val Ile Leu Ile Ala Arg Pro
                20                  25                  30

Gln His Val Gln Ala Ile Glu Ala Thr Gly Leu Arg Leu Glu Thr Gln
            35                  40                  45

Ser Phe Asp Glu Gln Val Lys Val Ser Ala Ser Ser Asp Pro Ser Ala
        50                  55                  60

Val Gln Gly Ala Asp Leu Val Leu Phe Cys Val Lys Ser Thr Asp Thr
65                  70                  75                  80

Gln Ser Ala Ala Leu Ala Met Lys Pro Ala Leu Ala Lys Ser Ala Leu
                85                  90                  95

Val Leu Ser Leu Gln Asn Gly Val Glu Asn Ala Asp Thr Leu Arg Ser
            100                 105                 110

Leu Leu Glu Gln Glu Val Ala Ala Val Val Tyr Val Ala Thr Glu
            115                 120                 125

Met Ala Gly Pro Gly His Val Arg His Gly Arg Gly Glu Leu Val
        130                 135                 140

Ile Glu Pro Thr Ser His Gly Ala Asn Leu Ala Ala Ile Phe Ala Ala
145                 150                 155                 160

Ala Gly Val Pro Val Glu Thr Ser Asp Asn Val Arg Gly Ala Leu Trp
                165                 170                 175

Ala Lys Leu Ile Leu Asn Cys Ala Tyr Asn Ala Leu Ser Ala Ile Thr
            180                 185                 190

Gln Leu Pro Tyr Gly Arg Leu Val Arg Gly Glu Gly Val Glu Ala Val
        195                 200                 205

Met Arg Asp Val Met Glu Glu Cys Phe Ala Val Ala Arg Ala Glu Gly
210                 215                 220
```

```
Val Lys Leu Pro Asp Asp Val Ala Leu Ala Ile Arg Arg Ile Ala Glu
225                 230                 235                 240

Thr Met Pro Gly Gln Ser Ser Ser Thr Ala Gln Asp Leu Ala Arg Gly
                245                 250                 255

Lys Arg Ser Glu Ile Asp His Leu Asn Gly Leu Ile Val Arg Arg Gly
            260                 265                 270

Asp Ala Leu Gly Ile Pro Val Pro Ala Asn Arg Val Leu His Ala Leu
        275                 280                 285

Val Arg Leu Ile Glu Asp Lys Gln Gln His Gly
    290                 295

<210> SEQ ID NO 14
<211> LENGTH: 325
<212> TYPE: PRT
<213> ORGANISM: Ralstonia solanacearum

<400> SEQUENCE: 14

Met Thr Arg Ile Cys Ile Val Gly Ala Gly Ala Val Gly Gly Tyr Leu
1               5                   10                  15

Gly Ala Arg Leu Val Leu Ala Gly Glu Ala Ile Asn Val Leu Ala Arg
            20                  25                  30

Gly Ala Thr Leu Gln Ala Leu Gln Thr Ala Gly Leu Arg Leu Thr Glu
        35                  40                  45

Asp Gly Ala Thr His Thr Leu Pro Val Arg Ala Thr His Asp Ala Ala
    50                  55                  60

Ala Leu Gly Glu Gln Asp Val Val Ile Val Ala Val Lys Ala Pro Ala
65                  70                  75                  80

Leu Glu Ser Val Ala Ala Gly Ile Ala Pro Leu Ile Gly Pro Gly Thr
                85                  90                  95

Arg Val Val Val Ala Met Asn Gly Val Pro Trp Trp Phe Phe Asp Arg
            100                 105                 110

Pro Gly Pro Leu Gln Gly Gln Arg Leu Gln Ala Val Asp Pro His Gly
        115                 120                 125

Arg Ile Ala Gln Ala Ile Pro Thr Arg His Val Leu Gly Gly Val Val
    130                 135                 140

His Leu Thr Cys Ala Thr Val Ser Pro Gly His Ile Arg His Gly Asn
145                 150                 155                 160

Gly Arg Arg Leu Ile Leu Gly Glu Pro Ala Gly Gly Ala Ser Pro Arg
                165                 170                 175

Leu Ala Ser Ile Ala Ala Leu Phe Gly Arg Ala Gly Leu Gln Ala Glu
            180                 185                 190

Cys Ser Glu Ala Ile Gln Arg Asp Ile Trp Phe Lys Leu Trp Gly Asn
        195                 200                 205

Met Thr Met Asn Pro Val Ser Val Leu Thr Gly Ala Thr Cys Asp Arg
    210                 215                 220

Ile Leu Asp Asp Pro Leu Val Ser Ala Phe Cys Leu Ala Val Met Ala
225                 230                 235                 240

Glu Ala Lys Ala Ile Gly Ala Arg Ile Gly Cys Pro Ile Glu Gln Ser
                245                 250                 255

Gly Glu Ala Arg Ser Ala Val Thr Arg Gln Leu Gly Ala Phe Lys Thr
            260                 265                 270

Ser Met Leu Gln Asp Ala Glu Ala Gly Arg Gly Pro Leu Glu Ile Asp
        275                 280                 285

Ala Leu Val Ala Ser Val Arg Glu Ile Gly Leu His Val Gly Val Pro
    290                 295                 300
```

Thr Pro Gln Ile Asp Thr Leu Leu Gly Leu Val Arg Leu His Ala Gln
305                 310                 315                 320

Thr Arg Gly Leu Tyr
            325

<210> SEQ ID NO 15
<211> LENGTH: 312
<212> TYPE: PRT
<213> ORGANISM: Stenotrophomonas maltophilia

<400> SEQUENCE: 15

Met Arg Ile Leu Ile Leu Gly Ala Gly Thr Gly Gly Tyr Phe Gly
1               5                   10                  15

Gly Arg Leu Ala Gln Ala Gly Val Asp Val Thr Phe Leu Val Arg Pro
                20                  25                  30

Ala Arg Ala Ala Gln Leu Asp Arg Asp Gly Leu Val Ile Arg Ser Pro
            35                  40                  45

Leu Gly Asp Ala Ser Phe Pro Val Gln His Val Thr Ala Asp Ala Leu
50                  55                  60

Pro Ala Leu Ala Ala Gln Lys Pro Phe Asp Leu Val Ile Leu Ser Cys
65                  70                  75                  80

Lys Ala Tyr Asp Leu Asp Ser Ser Ile Asp Ala Ile Ala Pro Ala Val
                85                  90                  95

Gly Ala Asn Thr Thr Val Leu Pro Ile Leu Asn Gly Leu His His Tyr
            100                 105                 110

Asn Ala Leu Asp Leu Arg Phe Gly Arg Asp Ala Val Leu Gly Gly Leu
        115                 120                 125

Cys Phe Ile Ser Ala Thr Lys Ala Pro Asp Gly Ala Val Leu His Leu
130                 135                 140

Gly Lys Pro Ala Lys Leu Thr Phe Gly Glu Arg Asp Gly Gly Ala Ile
145                 150                 155                 160

Ser Thr Arg Val Arg Ala Phe Ala Ala Ala Cys Ala Gln Ala Asn Leu
                165                 170                 175

Asp His Leu Ala Ser Glu His Ile Gly Gln Glu Gln Trp Ile Lys Tyr
            180                 185                 190

Thr Phe Leu Thr Ala Leu Ala Ala Thr Cys Leu Leu Arg Ala Asp
        195                 200                 205

Ile Gly Ser Ile Val Ala Thr Asp Asp Gly Glu Ala Ile Val Arg Gly
210                 215                 220

Leu Tyr Asp Glu Cys Leu Ala Val Ala Glu Ala Ala Gly Glu Pro Ile
225                 230                 235                 240

Pro Asp Ala Ala Gln Asp Thr Ala Arg Gly Thr Leu Thr Gln Ala Gly
                245                 250                 255

Ser Ala Leu Lys Ala Ser Met Leu Arg Asp Leu Glu Ala Gly Gln Gln
            260                 265                 270

Val Glu Ala Ala Gln Ile Val Gly Asp Met Leu Ala Arg Ala Arg Lys
        275                 280                 285

Ala Asp Gln Glu Gly Leu Leu Leu Gln Val Ala Tyr Ser Ser Leu Gln
290                 295                 300

Ala Tyr Gln Ala Leu Arg Ala Ala
305                 310

<210> SEQ ID NO 16
<211> LENGTH: 313
<212> TYPE: PRT
<213> ORGANISM: Enterococcus faecalis

<400> SEQUENCE: 16

```
Met Lys Ile Ala Ile Ala Gly Ala Gly Ala Met Gly Ser Arg Leu Gly
1               5                   10                  15

Ile Met Leu His Gln Gly Gly Asn Asp Val Thr Leu Ile Asp Gln Trp
            20                  25                  30

Pro Ala His Ile Glu Ala Ile Arg Lys Asn Gly Leu Ile Ala Asp Phe
        35                  40                  45

Asn Gly Glu Glu Val Val Ala Asn Leu Pro Ile Phe Ser Pro Glu Glu
    50                  55                  60

Ile Asp His Gln Asn Glu Gln Val Asp Leu Ile Ile Ala Leu Thr Lys
65                  70                  75                  80

Ala Gln Gln Leu Asp Ala Met Phe Lys Ala Ile Gln Pro Met Ile Thr
                85                  90                  95

Glu Lys Thr Tyr Val Leu Cys Leu Leu Asn Gly Leu Gly His Glu Asp
            100                 105                 110

Val Leu Glu Lys Tyr Val Pro Lys Glu Asn Ile Leu Val Gly Ile Thr
        115                 120                 125

Met Trp Thr Ala Gly Leu Glu Gly Pro Gly Arg Val Lys Leu Leu Gly
    130                 135                 140

Asp Gly Glu Ile Glu Leu Glu Asn Ile Asp Pro Ser Gly Lys Lys Phe
145                 150                 155                 160

Ala Leu Glu Val Val Asp Val Phe Gln Lys Ala Gly Leu Asn Pro Ser
                165                 170                 175

Tyr Ser Ser Asn Val Arg Tyr Ser Ile Trp Arg Lys Ala Cys Val Asn
            180                 185                 190

Gly Thr Leu Asn Gly Leu Cys Thr Ile Leu Asp Cys Asn Ile Ala Glu
        195                 200                 205

Phe Gly Ala Leu Pro Val Ser Glu Ser Leu Val Lys Thr Leu Ile Ser
    210                 215                 220

Glu Phe Ala Ala Val Ala Glu Lys Glu Ala Ile Tyr Leu Asp Gln Ala
225                 230                 235                 240

Glu Val Tyr Thr His Ile Val Gln Thr Tyr Asp Pro Asn Gly Ile Gly
                245                 250                 255

Leu His Tyr Pro Ser Met Tyr Gln Asp Leu Ile Lys Asn His Arg Leu
            260                 265                 270

Thr Glu Ile Asp Tyr Ile Asn Gly Ala Val Trp Arg Lys Gly Gln Lys
        275                 280                 285

Tyr Asn Val Ala Thr Pro Phe Cys Ala Met Leu Thr Gln Leu Val His
    290                 295                 300

Gly Lys Glu Glu Leu Leu Gly Ala Lys
305                 310
```

<210> SEQ ID NO 17
<211> LENGTH: 298
<212> TYPE: PRT
<213> ORGANISM: Bacillus subtilis

<400> SEQUENCE: 17

```
Met Lys Ile Gly Ile Ile Gly Gly Gly Ser Val Gly Leu Leu Cys Ala
1               5                   10                  15

Tyr Tyr Leu Ser Leu Tyr His Asp Val Thr Val Val Thr Arg Arg Gln
            20                  25                  30

Glu Gln Ala Ala Ala Ile Gln Ser Glu Gly Ile Arg Leu Tyr Lys Gly
        35                  40                  45
```

```
Gly Glu Glu Phe Arg Ala Asp Cys Ser Ala Asp Thr Ser Ile Asn Ser
 50                  55                  60

Asp Phe Asp Leu Leu Val Val Thr Val Lys Gln His Gln Leu Gln Ser
 65                  70                  75                  80

Val Phe Ser Ser Leu Glu Arg Ile Gly Lys Thr Asn Ile Leu Phe Leu
                 85                  90                  95

Gln Asn Gly Met Gly His Ile His Asp Leu Lys Asp Trp His Val Gly
            100                 105                 110

His Ser Ile Tyr Val Gly Ile Val Glu His Gly Ala Val Arg Lys Ser
            115                 120                 125

Asp Thr Ala Val Asp His Thr Gly Leu Gly Ala Ile Lys Trp Ser Ala
130                 135                 140

Phe Asp Asp Ala Glu Pro Asp Arg Leu Asn Ile Leu Phe Gln His Asn
145                 150                 155                 160

His Ser Asp Phe Pro Ile Tyr Tyr Glu Thr Asp Trp Tyr Arg Leu Leu
                165                 170                 175

Thr Gly Lys Leu Ile Val Asn Ala Cys Ile Asn Pro Leu Thr Ala Leu
            180                 185                 190

Leu Gln Val Lys Asn Gly Glu Leu Leu Thr Thr Pro Ala Tyr Leu Ala
            195                 200                 205

Phe Met Lys Leu Val Phe Gln Glu Ala Cys Arg Ile Leu Lys Leu Glu
210                 215                 220

Asn Glu Glu Lys Ala Trp Glu Arg Val Gln Ala Val Cys Gly Gln Thr
225                 230                 235                 240

Lys Glu Asn Arg Ser Ser Met Leu Val Asp Val Ile Gly Gly Arg Gln
                245                 250                 255

Thr Glu Ala Asp Ala Ile Ile Gly Tyr Leu Leu Lys Glu Ala Ser Leu
            260                 265                 270

Gln Gly Leu Asp Ala Val His Leu Glu Phe Leu Tyr Gly Ser Ile Lys
            275                 280                 285

Ala Leu Glu Arg Asn Thr Asn Lys Val Phe
290                 295

<210> SEQ ID NO 18
<211> LENGTH: 125
<212> TYPE: PRT
<213> ORGANISM: artificial sequence
<220> FEATURE:
<223> OTHER INFORMATION: shortened consensus structure for aspartate 1-
      decarboxylase
<220> FEATURE:
<221> NAME/KEY: MISC_FEATURE
<222> LOCATION: (1)..(8)
<223> OTHER INFORMATION: X may be any amino acid
<220> FEATURE:
<221> NAME/KEY: MISC_FEATURE
<222> LOCATION: (10)..(10)
<223> OTHER INFORMATION: X may be any amino acid
<220> FEATURE:
<221> NAME/KEY: MISC_FEATURE
<222> LOCATION: (12)..(21)
<223> OTHER INFORMATION: X may be any amino acid
<220> FEATURE:
<221> NAME/KEY: MISC_FEATURE
<222> LOCATION: (23)..(21)
<223> OTHER INFORMATION: X may be any amino acid
<220> FEATURE:
<221> NAME/KEY: misc_feature
<222> LOCATION: (23)..(23)
<223> OTHER INFORMATION: Xaa can be any naturally occurring amino acid
```

```
<220> FEATURE:
<221> NAME/KEY: MISC_FEATURE
<222> LOCATION: (26)..(51)
<223> OTHER INFORMATION: X may be any amino acid
<220> FEATURE:
<221> NAME/KEY: MISC_FEATURE
<222> LOCATION: (53)..(51)
<223> OTHER INFORMATION: X may be any amino acid
<220> FEATURE:
<221> NAME/KEY: misc_feature
<222> LOCATION: (53)..(53)
<223> OTHER INFORMATION: Xaa can be any naturally occurring amino acid
<220> FEATURE:
<221> NAME/KEY: MISC_FEATURE
<222> LOCATION: (55)..(56)
<223> OTHER INFORMATION: X may be any amino acid
<220> FEATURE:
<221> NAME/KEY: MISC_FEATURE
<222> LOCATION: (59)..(71)
<223> OTHER INFORMATION: X may be any amino acid
<220> FEATURE:
<221> NAME/KEY: MISC_FEATURE
<222> LOCATION: (74)..(85)
<223> OTHER INFORMATION: X may be any amino acid
<220> FEATURE:
<221> NAME/KEY: MISC_FEATURE
<222> LOCATION: (87)..(125)
<223> OTHER INFORMATION: X may be any amino acid

<400> SEQUENCE: 18

Xaa Xaa Xaa Xaa Xaa Xaa Xaa Xaa Lys Xaa His Xaa Xaa Xaa Xaa Xaa
1               5                   10                  15

Xaa Xaa Xaa Xaa Xaa Tyr Xaa Gly Ser Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Gly Xaa Arg Xaa Xaa Thr Tyr Xaa Xaa Xaa Xaa Xaa
    50                  55                  60

Xaa Xaa Xaa Xaa Xaa Xaa Xaa Asn Gly Xaa Xaa Xaa Xaa Xaa Xaa
65              70                  75                  80

Xaa Xaa Xaa Xaa Xaa Ile Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa
        115                 120                 125

<210> SEQ ID NO 19
<211> LENGTH: 270
<212> TYPE: PRT
<213> ORGANISM: artificial sequence
<220> FEATURE:
<223> OTHER INFORMATION: conserved structure sequence for 2-
      dehydropantoate reductase
<220> FEATURE:
<221> NAME/KEY: MISC_FEATURE
<222> LOCATION: (1)..(6)
<223> OTHER INFORMATION: X may be any amino acid
<220> FEATURE:
<221> NAME/KEY: MISC_FEATURE
<222> LOCATION: (8)..(8)
<223> OTHER INFORMATION: X may be any amino acid
<220> FEATURE:
<221> NAME/KEY: MISC_FEATURE
<222> LOCATION: (10)..(11)
<223> OTHER INFORMATION: X may be any amino acid
<220> FEATURE:
<221> NAME/KEY: MISC_FEATURE
<222> LOCATION: (13)..(18)
<223> OTHER INFORMATION: X may be any amino acid
```

```
<220> FEATURE:
<221> NAME/KEY: MISC_FEATURE
<222> LOCATION: (20)..(63)
<223> OTHER INFORMATION: X may be any amino acid
<220> FEATURE:
<221> NAME/KEY: MISC_FEATURE
<222> LOCATION: (65)..(89)
<223> OTHER INFORMATION: X may be any amino acid
<220> FEATURE:
<221> NAME/KEY: MISC_FEATURE
<222> LOCATION: (92)..(162)
<223> OTHER INFORMATION: X may be any amino acid
<220> FEATURE:
<221> NAME/KEY: MISC_FEATURE
<222> LOCATION: (164)..(166)
<223> OTHER INFORMATION: X may be any amino acid
<220> FEATURE:
<221> NAME/KEY: MISC_FEATURE
<222> LOCATION: (168)..(170)
<223> OTHER INFORMATION: X may be any amino acid
<220> FEATURE:
<221> NAME/KEY: MISC_FEATURE
<222> LOCATION: (172)..(196)
<223> OTHER INFORMATION: X may be any amino acid
<220> FEATURE:
<221> NAME/KEY: MISC_FEATURE
<222> LOCATION: (198)..(226)
<223> OTHER INFORMATION: X may be any amino acid
<220> FEATURE:
<221> NAME/KEY: MISC_FEATURE
<222> LOCATION: (228)..(230)
<223> OTHER INFORMATION: X may be any amino acid
<220> FEATURE:
<221> NAME/KEY: MISC_FEATURE
<222> LOCATION: (232)..(238)
<223> OTHER INFORMATION: X may be any amino acid
<220> FEATURE:
<221> NAME/KEY: MISC_FEATURE
<222> LOCATION: (240)..(270)
<223> OTHER INFORMATION: X may be any amino acid

<400> SEQUENCE: 19

Xaa Xaa Xaa Xaa Xaa Gly Xaa Gly Xaa Xaa Gly Xaa Xaa Xaa Xaa
1               5                   10                  15

Xaa Xaa Leu Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Lys
    50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Asn Gly Xaa Xaa Xaa Xaa
                85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Xaa Xaa Xaa Xaa Xaa Xaa
145                 150                 155                 160

Xaa Xaa Lys Xaa Xaa Xaa Asn Xaa Xaa Asn Xaa Xaa Xaa Xaa Xaa
                165                 170                 175

Xaa Xaa Xaa Xaa Xaa Xaa Xaa Xaa Xaa Xaa Xaa Xaa Xaa Xaa Xaa
            180                 185                 190
```

```
Xaa Xaa Xaa Xaa Glu Xaa Xaa Xaa Xaa Xaa Xaa Xaa Xaa Xaa Xaa
        195             200             205

Xaa Xaa Xaa Xaa Xaa Xaa Xaa Xaa Xaa Xaa Xaa Xaa Xaa Xaa Xaa
    210             215             220

Xaa Xaa Ser Xaa Xaa Xaa Asp Xaa Xaa Xaa Xaa Xaa Xaa Glu Xaa
225             230             235             240

Xaa Xaa Xaa Xaa Xaa Xaa Xaa Xaa Xaa Xaa Xaa Xaa Xaa Xaa Xaa
            245             250             255

Xaa Xaa Xaa Xaa Xaa Xaa Xaa Xaa Xaa Xaa Xaa Xaa
            260             265             270
```